United States Patent [19]

Heinemann et al.

[11] Patent Number: 5,202,257
[45] Date of Patent: Apr. 13, 1993

[54] ISOLATED NUCLEIC ACIDS ENCODING GLUTAMATE RECEPTOR PROTEIN

[75] Inventors: Stephen F. Heinemann, La Jolla; James R. Boulter, San Diego; Michael Hollmann, Del Mar; Bernhard Bettler, Solana Beach; Jan E. Jensen, San Diego, all of Calif.

[73] Assignee: The Salk Institute for Biological Studies, La Jolla, Calif.

[21] Appl. No.: 718,575

[22] Filed: Jun. 21, 1991

Related U.S. Application Data

[63] Continuation of Ser. No. 6,153, Sep. 13, 1984, which is a continuation-in-part of Ser. No. 428,116, Oct. 27, 1989.

[51] Int. Cl.$^5$ .................. C12N 15/12; C12N 15/63
[52] U.S. Cl. .................. 435/252.3; 435/69.1; 435/320.1; 536/24.3; 536/23.1
[58] Field of Search ............. 435/252.3, 69.1, 320.1; 536/26, 27

[56] References Cited

PUBLICATIONS

Nature 328:836–838, Oct. 29, 1987, Masu et al. CDNA cloning of bovine substance-K receptor through oocyte expression system.
Nature 310:318–321, Jul. 26, 1984, Houamed et al. Expression of functional GABA, glycine and glutamate receptors in *Xenopus* oocytes injected with rat brain mRNA.
Nucl. Acids Res. 13:4739–4749, Jul. 1985, Hauptmann et al. A novel class of human type I interferons.
Stevens, A finger on brain receptors, Nature vol. 342:620–621 (1989).
Hollmann et al., Cloning by functional expression of a member of the glutamate receptor family, Nature vol. 342:643–648 (1989).
Wada et al, Sequence and expression of a frog brain complementary DNA encoding a kainate-binding protein, Nature vol. 342:684–689 (1989).
Gregor et al., Molecular structure of the chick cerebellar kainate-binding subunit of a putative glutamate receptor, Nature vol. 342:689–692 (1989).
Keinanen et al., A Family of AMPA-Selective Glutamate Receptors, Science vol. 249:556–560 (1990).
Boulter et al., Molecular Cloning and Functional Expression of Glutamate Receptor Subunit Genes, Science vol. 249:1033–1037 (1990).
Bettler et al., Cloning of a Novel Glutamate Receptor Subunit, GluR5: Expression in the Nervous System during Development, Neuron vol. 5:583–595 (1990).
Masu et al., "Sequence and expression of a metabotropic glutamate receptor", Nature vol. 349:760–765 (1991).

*Primary Examiner*—Robert J. Hill, Jr.
*Assistant Examiner*—John D. Ulm
*Attorney, Agent, or Firm*—Pretty, Schroeder, Brueggemann & Clark

[57] ABSTRACT

The present invention discloses novel DNAs that encode proteins having electrophysiological and pharmacological properties characteristic of glutamate receptors. The glutamate receptors are exemplified by proteins encoded by representative cDNA clones GluR1, GluR2, GluR3, GluR4, GluR5, GluR6 and GluR7, fragments thereof, and functional combinations of these glutamate receptor proteins and/or fragments. DNA sequences from the cDNA clones for GluR1, GluR2, GluR3, GluR5 and GluR5 are especially useful as probes, thus enabling those skilled in the art to identify, without undue experimentation, other members of the L-glutamate receptor family.

14 Claims, 17 Drawing Sheets

```
GluR-K1    ..C F I T P S - F P V D T S N Q...
nAChR-α1   ..C E I I V T H F P F D E Q N C...
nAChR-α2   ..C S I D V T F F P F D Q Q N C...
nAChR-α3   ..C K I D V T Y F P F D Y Q N C...
nAChR-α4   ..C S I D V T F F P F D Q Q N C...
nAChR-β1   ..C S I Q V T Y F P F D W Q N C...
nAChR-β2   ..C K I E V K H F P F D Q Q N C...
nAChR-β3   ..C T M D V T F F P F D R Q N C...
nAChR-β4   ..C K I E V K H F P F D Q Q N C...
nAChR-γ    ..C P I A V T Y F P F D W Q N C...
nAChR-δ    ..C P I S V T Y F P F D W Q N C...
GABA-α     ..C P M H L E D F P M D A H A C...
GABA-β     ..C M M D L R R Y P L D E Q N C...
GlyR 48k   ..C P M D L K N F P M D V Q T C...
```

FIG. IA

```
GluR-K1    ..Y E I W M - C I V F A Y I G V S V V L F L V S R F S P...
nAChR-α1   ..G E K M T L S I - S V L L S L T V F L L V I V E L I P...
nAChR-α2   ..G E K I T L C I - S V L L S L T V F L L L I T E I I P...
nAChR-α3   ..G E K V T L C I - S V L L S L T V F L L V I T E T I P...
nAChR-α4   ..G E K V T L C I - S V L L S L T V F L L L I T E I I P...
nAChR-β1   ..G E K M G L S I - F A L L T L T V F L L L L A D K V P...
nAChR-β2   ..G E K M T L C I - S V L L A L T V F L L L I S K I V P...
nAChR-β3   ..G E K L S L S T - S V L V S L T V F L L V I E E I I P...
nAChR-β4   ..G E K M T L C I - S V L L A L T F F L L L I S K I V P...
nAChR-γ    ..G Q K C T V A T - N V L L A Q T V F L F L V A K K V P...
nAChR-δ    ..G E K T S V A I - S V L L A Q S V F L L L I S K R L P...
GABA-α     ..N R E S V P A R - T V F G V T T V L T M T T L S I S A...
GABA-β     ..N Y D A S A A R V - A L G I T T V L T M T T I S T H L...
GlyR 48k   ..N M D A A P A R V - G L G I T T V L T M T T Q S S G S...
```

Block 1:
```
GluR1                                          
GluR2  MQKIMHISVLLSPVLWGLIFG   ANFPNNIQIGGLFPNQQSQ
GluR3  MGQSVLRAVFFLVLGLLGHSHG  VSSNSIQIGGLFPRGADQ
GluR4  MRIICRQIVLLFSGFSGTRHG   GFPNTISIGGLFMRNTVQ
GluR5  MERSTVLIQPGLWTRDTSWTLLYFLCYILP QTSPQVLRIGGIFETVENEP
              |_____SIGNAL PEPTIDE_____|        AFPSSVQIGGLFIRNTDQ
```

Block 2:
```
GluR1  QFSXGVYAIFGFYERRTVNMLTSFCGALHVCFITPSFPVDTSNQFVLQLRP
GluR2  QFSRGVYAIFGFYDKKSVNTITSFCGTLHVSFITPSFPTDGTHPFVIQMRP
GluR3  QFSRGVYAIFGFYDQMSMNTLLTSFCGALHTSFVTPSFPTDADVQFVIQMRP
GluR4  QYSRGVFAIFGLYDKRSVHTLLTSFCMRLHISLITPSFPTEGESQFVLQLRP
GluR5  QLALGVAALFGPSHSSSSVSAVQSICNALEVPHIQTRWKHPSVDSRDLFYIN
```

Block 3:
```
GluR1  QVTA        VNILTTTEEGYRMLFQDLEKKKERLVVVDCESERLNAILGQIV
GluR2  QVTAINVGNI   NNDKKDETYRSLFQDLELKKERRVILDCERDKVNDIVDQVI
GluR3  QVTARSVGNI   KDVQEFRRIIEEMDRRQEKKFYVIFDCEVERINTILEQVV
GluR4  HVSAICVENF    NDSYRQLLEELDRRQEKKFYVIFDCEIERLQNILEQIV
GluR5  KIKIRQLPPAN  KDAKPLLKEMKKSKEFYVIFDCSHETAAEILKQIL
```

Block 4:
```
GluR1  MQQWRTSDSRDHTRVDWKRPKYTSALTYDGVKVMAEAFQSLRRQRIDISRR
GluR2  IEHWSTLEEKEYPGAHTATIKYTSALTYDAVQVMTEAFRNLRKQRIEISRR
GluR3  IQRWVRLDEREFPEAKNAPLKYTSALTHDAILVIAEAFRYLRRQRVDVSRR
GluR4  MDRWKKLDQREYPGSET PPKYTSALTYDGVLVMAETFRSLRRQKIDISRR
GluR5  IEKWSMERLQAPPRPETGLLDGMMTTEAALMYDAVYMVAIASH RASQ
```

```
GluR1  LHVIEMKHDGI                    RKIGYWN   EDDKFVPAATDAQAGGD
GluR2  INIMELKTNGP                    RKIGYWS   EVDKMVVTLTELPSGND
GluR3  IDVYEMKVSGS                    RKAGYWN   EYERFVPFSDQQISND
GluR4  MDVFELKSTGP                    RKVGYWN   DMDKLVLIQDMPTLGND
GluR5  LDIISLKEEGTEKASGEVSKHLYKVWKKIGIWN         SNSGLNMTDGNRDRSNNI

GluR1  EHAAFRFALSQLTE       PPKLLPQIDIVNISDTFEMTYRFCS
GluR2  EYSAFRVGMVQFSTSE     FRLTPHIDNLEVANSFAVTNAFCS
GluR3  EHSAFRFAVQLYNTNQNTTEKPFHLNYHVDHLDSSNSFSVTNAFCS
GluR4  EYTAFRLAIFLHNTSPNASEAPFNLVPHVDNIETANSFAVTNAFCS
GluR5  VNVEELAFKFAVTSINRNR  TLMPNTTLTYDIQRINLFDSFEASRRACD

GluR1  ELQE        ALISIIDHYKWQTFVYIYDADRGLSVLQRVLDTAAAEKNW
GluR2  DLKG        ALLSLLIEYYQWDKFAYLYDSDRGLSTLQAVLDSAAEKKW
GluR3  ALKG        AILSLLSYYKWEKFVYLYDTERGFSVLQAIMEAAVQNNW
GluR4  SLRG        ALLSLLDHYEWNCFVFLYDTDRGYSILQAIMEKAGQNGW
GluR5  LYPDYAAISRAVLDLVLYYNWKTVTVVYEDSTGLIRLQELIKAPSRYNI

GluR1  KLEKNGIGYHYILANLGFMDIDLNKFKESGRNVTGFQLVNYTDTIPARI
GluR2  TIGKHVKGYHYIIANLGFTDGDLLKIQFGGANVSGFQIVDYDDSLVSKF
GluR3  ILGKHSRGYHYMLANLGFTDILLERVMHGGANITGFQIVNNENPMVQQF
GluR4  SVGKHVKGYHYIIANLGFKDISLERFIHGGANVTGFQLVDFNTPMVTKL
GluR5  FMGMMTEYYHYFFTTLDLFALDLELYRYSGVNMTGFRLLNIDNPHVSSI
```

FIG.2A-2

```
GluR1  G N A G D C L A N P A V P W G Q G I D I Q R A L Q Q V R F E G L T G N V Q F N E K G R R T N Y T
GluR2  G N A G D C L A N P A V P W G Q G V E I E R A L K Q V Q V Q G L S G N I K F D Q N G K R I N Y T
GluR3  G S A G D C L A N P A V P W S Q G I D I E R A L K M V Q V Q G M T G N I Q F D T Y G K R T N Y T
GluR4  G N A G D C L A N P A A P W G Q G I D M E R T L K Q V R I Q G L T G N V Q F D H Y G R R V N Y T
GluR5  L T V S S L Q C H R H K P W R L G P R F M N L I K E A R W D G L T G R I T F N K T D G L R K D F D

GluR1  N S S V Q N R T Y I V T T I L E D P Y V M L K N A N Q F E G N D R Y E G Y C V E L A A E I A K H
GluR2  T S G L E N K T V V V T T I L E S P Y V M M K K N H E M L E G N E R Y E G Y C V D L A A E I A K H
GluR3  S S S E N R T V V V T T I L E S P Y V M Y K K N H E Q L E G N E R Y E G Y C V D L A A E I A K H
GluR4  T A A I E N R T V V V T T I M E S P Y V M Y K K N H E M F E G N D K Y E G Y C V D L A Y E I A K H
GluR5  T D S L A N R T L I V T T I L E E P F V M F R K S D K P L Y G N D R F E G Y C L D L L K E L S N I

GluR1  V G Y S Y R L E I V S D G K Y G A R D P D T K A W N G M V G E L V Y G R A D V A V A P L T I T L V R E
GluR2  C G F K Y K L T I V G D G K Y G A R D A D T K I W N G M V G E L V Y G K A D I A V A P L T I T L V R E
GluR3  V R I K Y K L S I V G D G K Y G A R D P E T K I W N G M V G E L V Y G K A D I A V A P L T I T L V R E
GluR4  I G I K Y K I A I V P D G K Y G A R D A D T K I W N G M V G E L V Y G K A E I A V A P L T I T L V R E
GluR5  L G F L Y D V K L V P D G K Y G A Q N D K G E W N G M V K E L I D H R A D L A V A P L T I T Y V R E

├── MSR I ──┤

GluR1  V S V L F L V S R F S P Y E W H S E E F E E G R D Q T T S D W S N E F G I F N S L W F S L G A F
GluR2  V S V L F L V S R F S P Y E W H T E E F E D G R E T Q S S E S T N E F G I F N S L W F S L G A F
GluR3  V S V L F L V S R F S P Y E W H L E D N E E P R D P Q S P P D P P N E F G I F N S L W F S L G A F
GluR4  V S V L F L V S R F S P Y E W H T E E P E D G K E G P S D Q P P N E F G I F N S L W F S L G A F
GluR5  V S C V L F V I A R F T P Y G W Y N P H P C N P D S D V V E N N F T L L N S F W F G V G A L
```

```
GluR1  T T E E G M I R V R K S K G K Y A Y L L E S T M N E Y I E Q R K P C D T M K V G G N L D S K G Y G
GluR2  T T A E G V A R V R K S K G K Y A Y L L E S T M N E Y I E Q R K P C D T M K V G G N L D S K G Y G
GluR3  T T A D G V A R V R K S K G K F A F L L E S T M N E Y I E Q R K P C D T M K V G G N L D S K G Y G
GluR4  T T A E G V A R V R K S K G K F A F L L E S T M N E Y I E Q R K P C D T M K V G G N L D S K G Y G
GluR5  N S D E G I Q R V   L T T D Y A L L M E S T S I E Y V T Q R N   C N L T Q I G G L I D S K G Y G

GluR1  S A L S N V A G V F Y I L I G G L G L A M L V A L I E F C Y K S R S E S K R M K G F C L I P Q
GluR2  S A L S N V A G V F Y I L V G G L G L A M L V A L I E F C Y K S R A E A K R M K V A K N P Q N
GluR3  S A L S N V A G V F Y I L V G G L G L A M M V A L I E F C Y K S R A E S K R M K L T K N T Q N
GluR4  S A L S N V A G V F Y I L I G G L G L A M L V A L I E F C Y K S R A E A K R M K L T F S E A I
GluR5  S V L G V E N I G G I F I V L A A G L V L S V F V A I G E F L Y K S R K N N D V E Q C L S F N A I
                              └─── MSR IV ───┘
```

FIG.2A-5

R1  MPYIFAFFCTGFLGAVVG
R2  MQKIMHISVLLSPVLWGLIFG
R3  MGQSVLRAVFFLVLGLLGHSHG
R4  MRIICRQIVLLFSGFSGTRHG
R5  MERSTVLIQPGLWTRDTSWTLLYFLCYILP
R6  MKIISPVLSNLVFSRSIKVLLCLLWIGYSQG
R7  GAVAGSLGRIRSLVWEYWAGFLVCAFWIPDSRG

FIG.2B

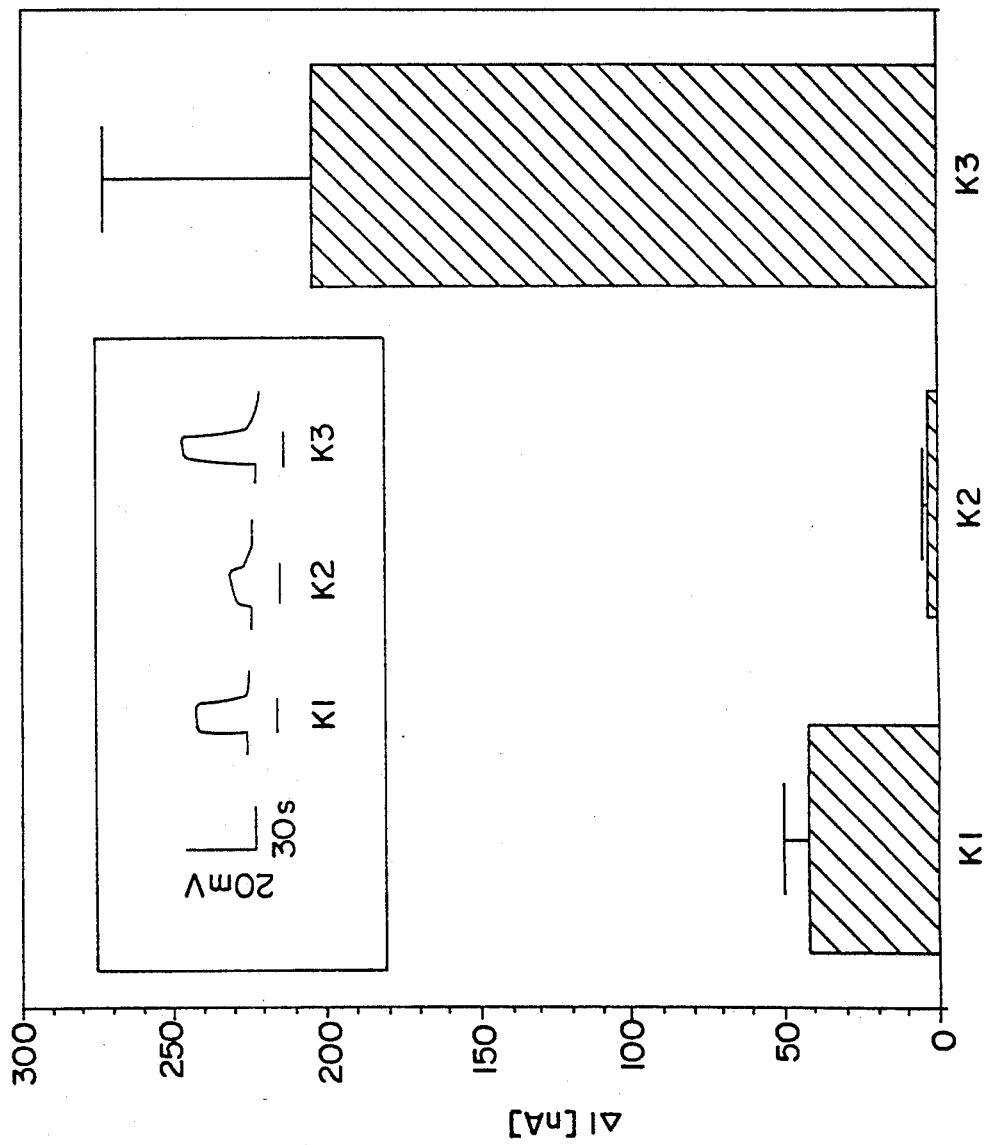

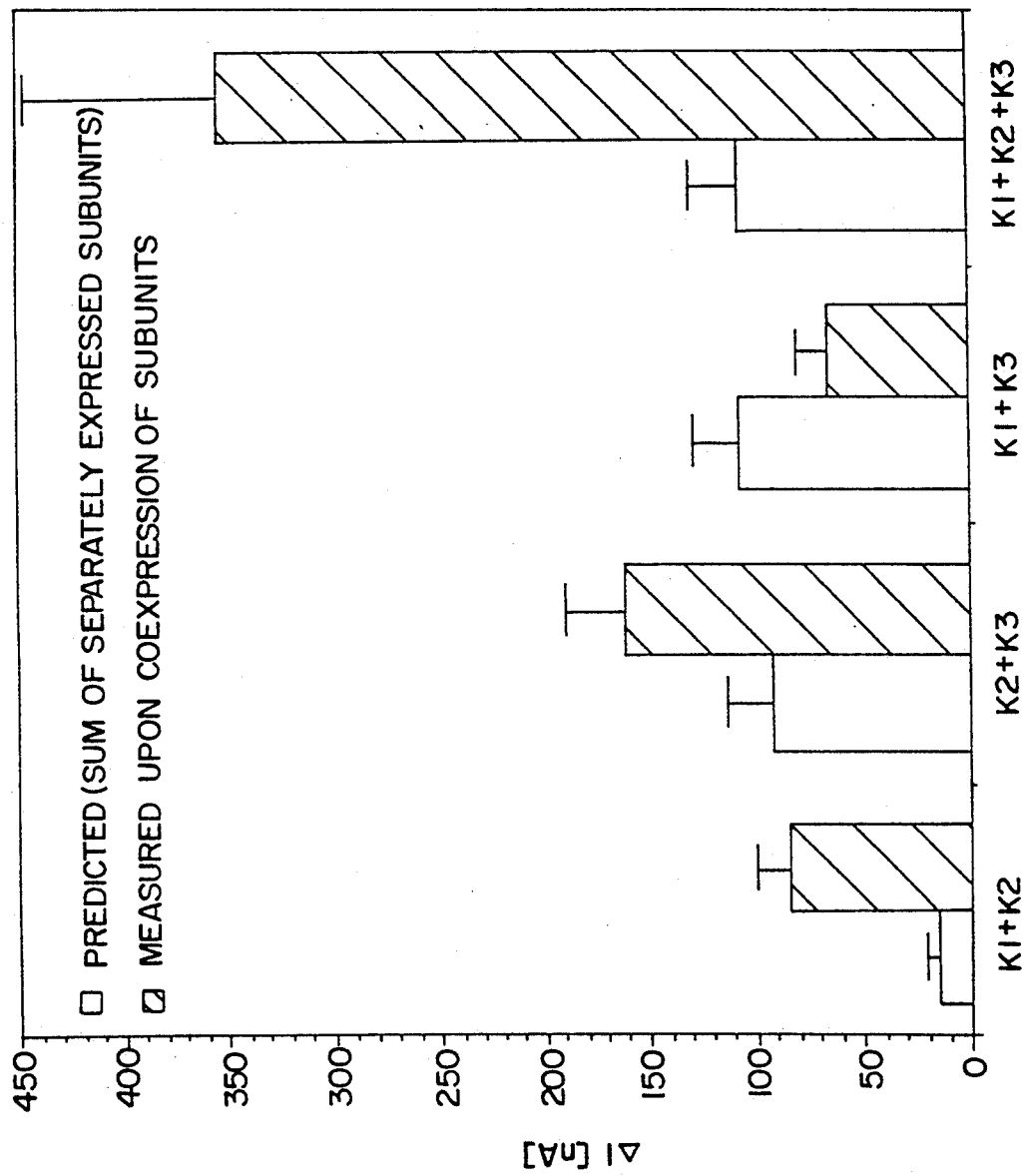

ISOLATED NUCLEIC ACIDS ENCODING GLUTAMATE RECEPTOR PROTEIN

ACKNOWLEDGEMENT

This invention was made with Government support under Grant Numbers NS 11549 and NS 28709.01, awarded by the National Institutes of Health. The Government has certain rights in this invention.

PRIOR APPLICATIONS

This is a continuing application of PCT application No. U.S. 90/06153, filed Oct. 25, 1990, which is, in turn, a continuation-in-part application of U.S. Ser. No. 428,116, filed Oct. 27, 1989, abandoned, the entire contents of which are hereby incorporated by reference herein.

FIELD OF THE INVENTION

The present invention relates to a family of novel DNAs and receptor proteins encoded thereby that comprise the glutamate neurotransmitter system. The invention also relates to methods for making such glutamate receptors and for using the receptor proteins in assays designed to identify and characterize compounds which affect the function of such receptors, e.g., glutamate agonists and antagonists.

BACKGROUND OF THE INVENTION

The amino acid L-glutamate is a major excitatory neurotransmitter in the mammalian central nervous system. Anatomical, biochemical and electrophysiological analyses suggest that glutamatergic systems are involved in a broad array of neuronal processes, including fast excitatory synaptic transmission, regulation of neurotransmitter releases, long-term potentiation, learning and memory, developmental synaptic plasticity, hypoxic-ischemic damage and neuronal cell death, epileptiform seizures, as well as the pathogenesis of several neurodegenerative disorders. See generally, Monaghan et al., Ann. Rev. Pharmacol. Toxicol. 29:365-402 (1980). This extensive repertoire of functions, especially those related to learning, neurotoxicity and neuropathology, has stimulated recent attempts to describe and define the mechanisms through which glutamate exerts its effects.

Currently, glutamate receptor classification schemes are based on pharmacological criteria which serve to define five receptor subtypes or classes: those activated by N-methyl-D-aspartic acid (NMDA), kainic acid (KA), α-amino-3-hydroxy-5-methyl-isoxazole-4-propionic acid (AMPA, formally called the quisqualic acid or QUIS receptor), 2-amino-4-phosphonobutyric acid (AP4 or APB), and 1-amino-cyclopentyl-1,3-dicarboxylic acid (ACPD). The effects of glutamate are mediated primarily through interactions with cation-selective, ionotropic receptors [Foster and Fagg, Brain Res. 7:103-164 (1984); Strange, Biochem. J. 249:309-318 (1988)]. An exception is the ACPD receptor subtype which has the properties of a metabotropic receptor. This class of glutamate receptors alters synaptic physiology via GTP-binding proteins and the second messengers diacylglycerol and inositol 1,4,5-triphosphate [Gundersen et al., Proc. R. Soc. London Ser. 221:127 (1984); Sladeczek et al., Nature 317:717 (1985); Nicoletti et al., J. Neurosci. 6:1905 (1986); Sugiyama et al., Nature 325:531 (1987)].

The electrophysiological and pharmacological properties of the glutamate receptors have been extensively studied and are now well established. See, for example, Foster and Fagg, Brain Res. Rev. 7:103 (1984); Cotman et al., Trends Neurosci. 10:263 (1987); Mayer and Westbrook, Prog. Neurobiol. 28:197 (1987); Watkins and Olvermann, Trends Neurosci. 10:265 (1987): and Blair et al., Science 242:577 (1988). This is in contrast to their biochemical characteristics and structure at the molecular level, which, until the teaching of the present invention, remained largely unknown.

SUMMARY OF THE INVENTION

The present invention discloses a family of novel glutamate receptor proteins and DNAs that encode them. The glutamate receptors of the invention have electrophysiological and pharmacological properties characteristic of glutamate receptors of the central and peripheral nervous system. The glutamate receptors of the present invention are exemplified by cation-selective ion channel-type proteins encoded by cDNA clones, GluR1, GluR2, GluR3, GluR4, GluR5, GluR6 and GluR7. In addition to being useful for the production of glutamate receptor proteins, these cDNAs are also useful as probes, thus enabling those skilled in the art, without undue experimentation, to identify and isolate additional proteins in the glutamate receptor family.

The novel functional glutamate receptors of the present invention can be assembled from a plurality of either individual GluR subunit proteins (homomeric) or from combinations of subunit proteins (heteromeric). GluR1, GluR2, GluR3, GluR4, GluR5, GluR6 and GluR7 are examples of presently preferred subunit proteins for forming homomeric receptors, while the combinations of GluR1, GluR2, GluR3, GluR4, GluR5, GluR6 and GluR7 are examples of presently preferred subunit proteins for forming heteromeric receptors.

In addition to disclosing novel glutamate receptor proteins, the present invention also comprises methods for using such receptors to identify and characterize compounds which affect the function of such receptors, e.g., agonists, antagonists, and modulators of glutamate receptor function. The invention also comprises methods for determining whether unknown protein(s) are functional as glutamate receptors.

BRIEF DESCRIPTION OF THE FIGURES

FIG. 1 (a and b) comprises two sequence homology analyses. FIG. 1a compares the extracellular region located between amino acid residues 89 and 106 of GluR1 with the "Cys-Cys-loop" region found in all other ligand-gated ion channels, showing sequence homology. FIG. 1b compares the putative TMD II region of GluR1 with hypothetical TMD II regions of other ligand-gated ion channels, suggesting protein sequence conservation.

FIG. 2A is a drawing which shows the alignment of deduced amino acid sequences for the GluR1, GluR2, GluR3, GluR4 and GluR5 (GluR5-1) subunits of the glutamate receptor gene family.

FIG. 2B is a drawing which shows the alignment of deduced amino acid signal sequences for the GluR1, GluR2, GluR3, GluR4, GluR5 (GluR5-1), GluR6 and GluR7 subunits of the glutamate receptor gene family.

Figure 6A:
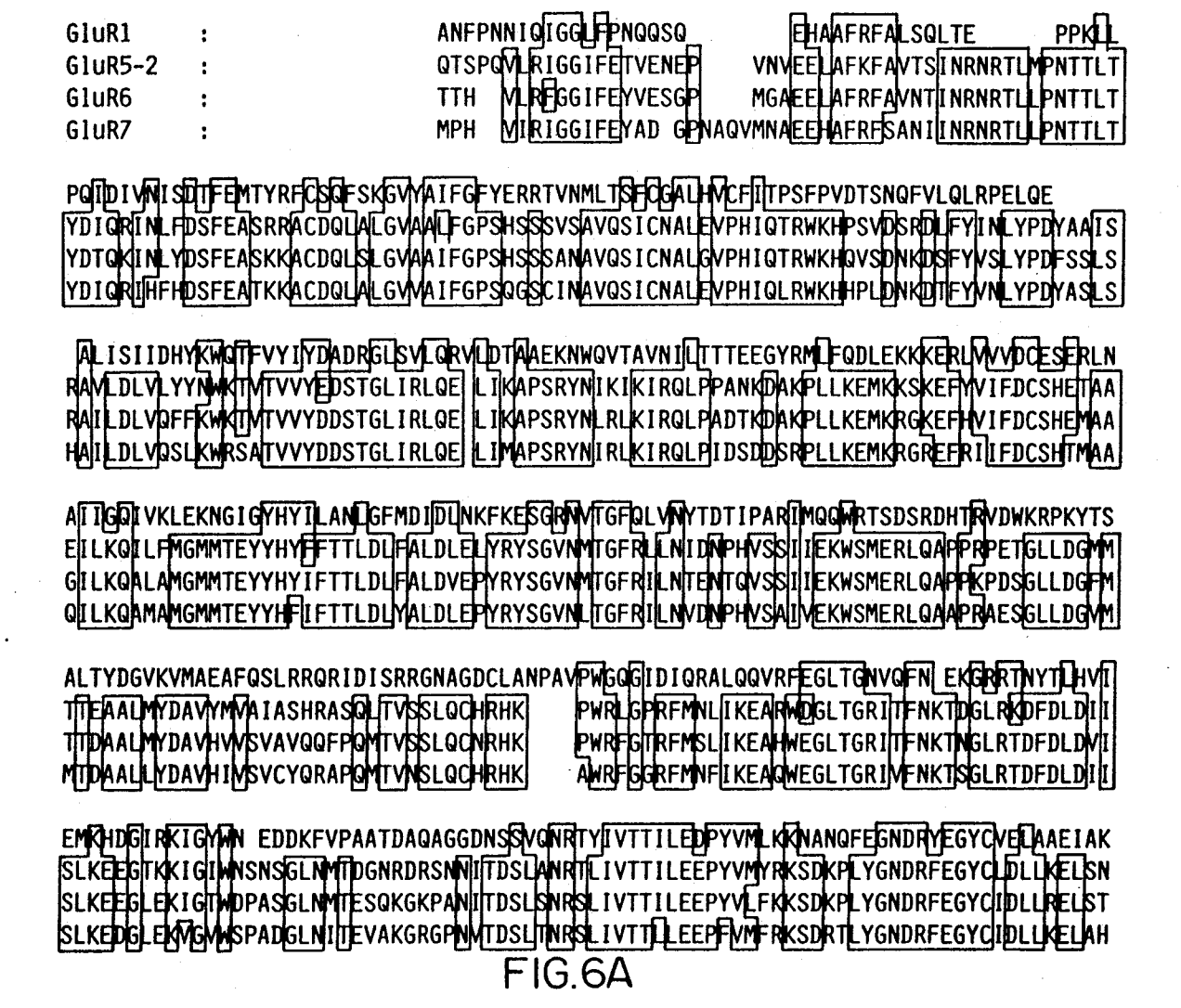
Figure 6B:
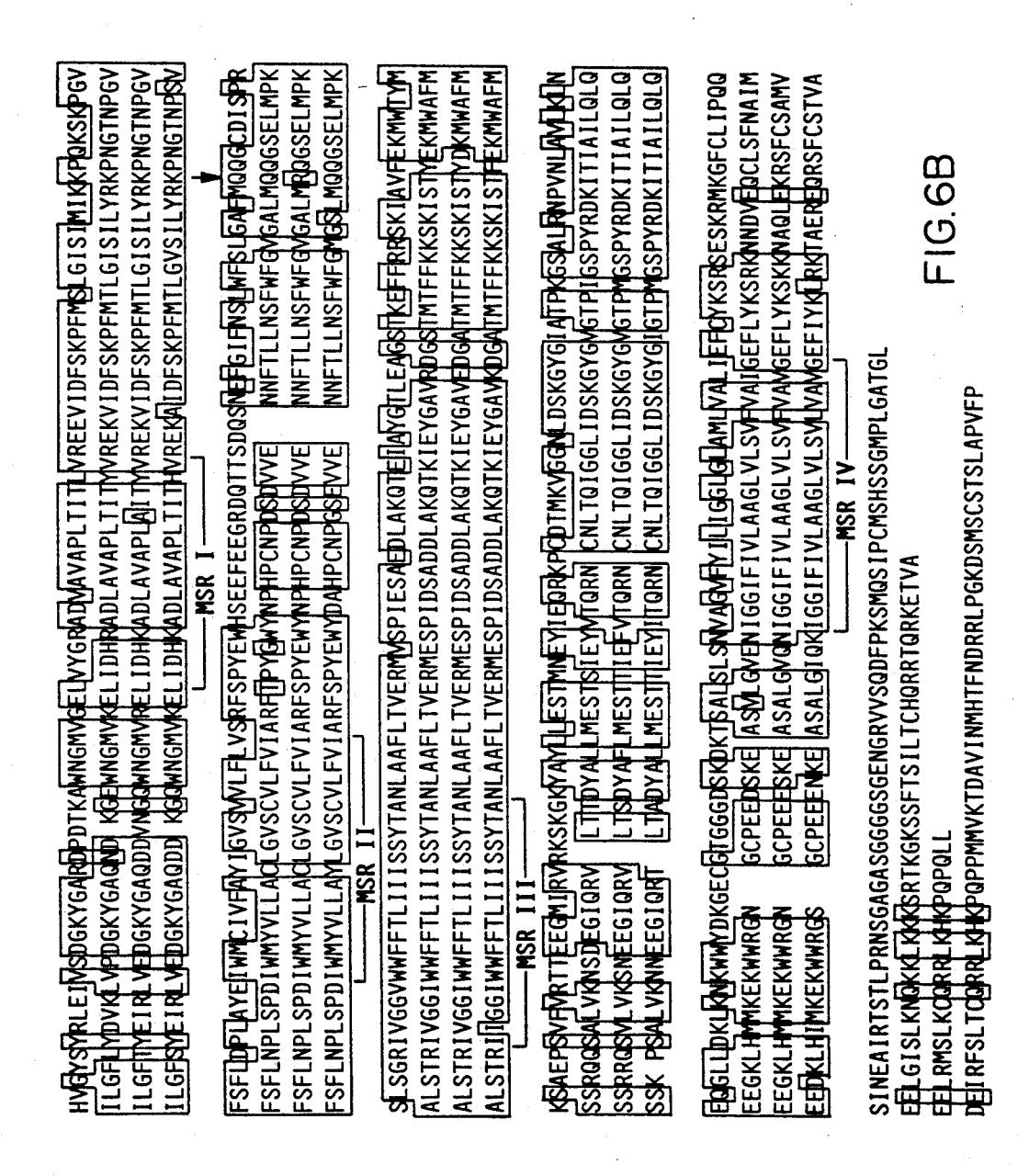

FIG. 6 presents an alignment of the deduced amino acid sequences of the rat glutamate receptor subunits GluR1, GluR5 and GluR6. The GluR5 clone GluR5-1 (without a 15 amino acid insert) is used for the alignment [see Bettler et al., Neuron 5: 583–595 (1990)]. Positions with amino acids identical between at least two proteins are enclosed and shaded. The predicted signal peptide and membrane spanning regions (MSR) are indicated [see Devereux et al., Nucl. Acids Res. 12: 387–395 (1984)]. Numbers indicate positions in the mature subunits.

Figure 3B:
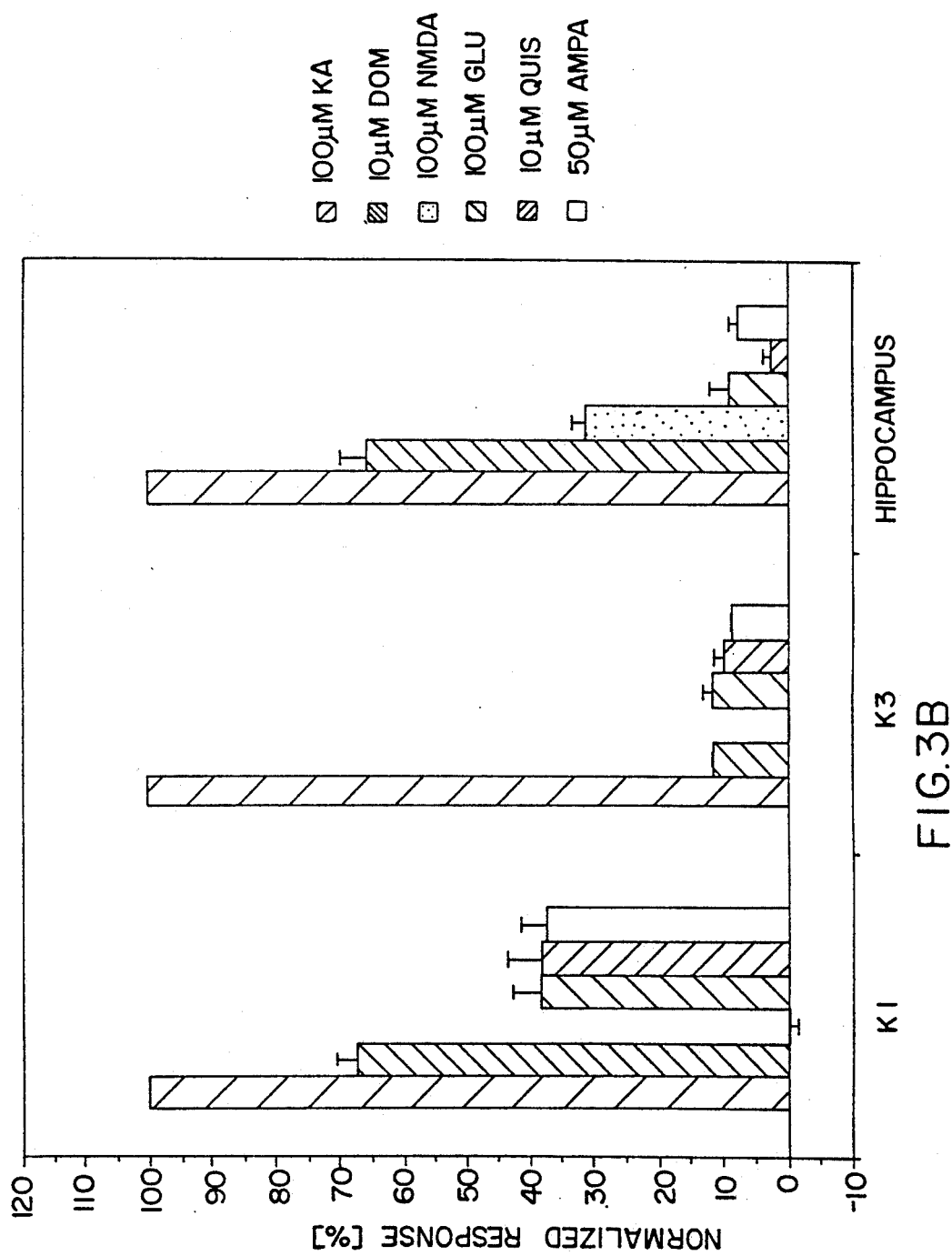
FIG. 3 (A and B) is comprised of two graphs which compare current responses measured in Xenopus oocytes injected with individual GluR1, GluR2 and GluR3 subunit RNAs (FIG. 3A) or rat brain hippocampus poly(A)+ RNA (FIG. 3B).

The amino acids appearing herein may be identified according to the following three-letter or one-letter abbreviations:

| Amino Acid | 3 Letter Abbreviation | 1 Letter Abbreviation |
| --- | --- | --- |
| L-Alanine | Ala | A |
| L-Arginine | Arg | R |
| L-Asparagine | Asn | N |
| L-Aspartic Acid | Asp | D |
| L-Cysteine | Cys | C |
| L-Glutamine | Gln | Q |
| L-Glutamic Acid | Glu | E |
| L-Glycine | Gly | G |
| L-Histidine | His | H |
| L-Isoleucine | Ile | I |
| L-Leucine | Leu | L |
| L-Lysine | Lys | K |
| L-methionine | Met | M |
| L-Phenylalanine | Phe | F |
| L-Proline | Pro | P |
| L-Serine | Ser | S |
| L-Threonine | Thr | T |
| L-Tryptophan | Trp | W |
| L-Tyrosine | Tyr | Y |
| L-Valine | Val | V |

The nucleotides appearing herein have the usual single-letter designations (A, G, T, C or U) routinely used in the art.

DETAILED DESCRIPTION OF THE INVENTION

The present invention discloses a family of glutamate receptors, novel DNAs that encode these receptors, and various applications thereof.

As used herein, glutamate receptors refer to neurotransmitter receptor proteins that are activated by L-glutamate and related compounds. These receptor proteins are classified on the basis of their "pharmacology". Currently there are five classes of receptors, i.e., receptors activated by (1) N-methyl-D-aspartate (NMDA), which is a ligand (agonist) for the NMDA glutamate receptor subtype; (2) kainic acid (KA), which is a ligand (agonist) for the kainate glutamate receptor subtype; (3) α-amino-3-hydroxy-5-methylisoxazole- 4-propionic acid (AMPA), which is a ligand (agonist) for the AMPA glutamate receptor subtype, formerly called the quisqualic acid or QUIS receptor, wherein QUIS means quisqualic acid or quisqualate, which is a ligand (agonist) for the pharmacologically defined receptor subtype previously referred to as the QUIS (quisqualate) receptor; (4) 2-amino-4-phosphonobutyric acid (AP4 or APB), which is a ligand (agonist) for the APB glutamate receptor subtype; the acronym AP4 is also used to refer to this receptor subtype; and (5) 1-aminocyclopentyl-1,3-dicarboxylic acid (ACPD), which is a ligand (agonist) for the ACPD glutamate receptor subtype.

The effects of glutamate on the first four subtypes described above are mediated primarily through interactions with cation-selective, ionotropic receptors. The ACPD receptor subtype, however, is an exception in that it has the properties of a metabotropic receptor. Metabotropic receptors alter synaptic physiology via GTP-binding proteins and second messengers (i.e., diacylglycerol and inositol 1,4,5-triphosphate).

In one aspect, the present invention comprises substantially pure proteins, or functional fragments thereof, having electrophysiological and pharmacological properties characteristic of at least one ionotropic glutamate receptor subtype selected from the N-methyl-D-aspartate (NMDA) subtype, the α-amino-3-hydroxy-5-methylisoxazole-4-propionic acid (AMPA) subtype, kainate (KA) subtype or the 2-amino-4-phosphonobutyrate (APB) subtype.

When used herein as a modifier of glutamate receptor protein(s) of the present invention, the phrase "having electrophysiological and pharmacological properties characteristic of a glutamate receptor" means that the neuronal signal(s) generated by receptor protein in responce to glutamate or glutamate-like ligands will be comparable to those of known glutamate receptors.

The term "functional", when used herein as a modifier of glutamate receptor protein(s) of the present invention (or fragments thereof), means that binding of glutamate (or glutamate-like) ligand to receptor protein(s) causes membrane "ion channels" to open. This allows ions to move across the membrane, which in turn depolarizes the cell and generates a neuronal signal. Stated another way, "functional" means that a neuronal signal is generated as a consequence of ligand binding to receptor protein(s).

As used herein, the words "protein", "peptide" and "polypeptide" are considered to be equivalent terms and are used interchangeably.

Also contemplated by the present invention are homomeric and heteromeric (or multimeric) combinations of the above-described receptor subtypes.

As used herein, homomeric means receptors comprised of a plurality of only one type of subunit protein, e.g., homodimers, homotrimers, etc.

As used herein, heteromeric or multimeric means receptors comprised of more than one type of subunit protein.

In another aspect, the invention comprises antibodies generated against the above-described receptor proteins. Such antibodies can be used to modulate the ion channel activity of glutamate receptors, by contacting such receptors with an effective amount of such antibody.

In yet another aspect, the invention comprises substantially pure DNA encoding proteins or functional fragments thereof, as described hereinabove.

Use of the phrase "substantially pure" in the present specification and claims as a modifier of DNA, RNA, polypeptides or proteins means that the DNA, RNA, polypeptides or proteins so designated have been separated from their in vivo cellular environment. As a result of this separation and purification, the substantially pure DNAs, RNAs, polypeptides and proteins are useful in ways that the non-separated, impure DNAs, RNAs, polypeptides or proteins are not.

In still another aspect, the invention comprises cells transformed with DNAs of the invention.

In another aspect, the invention comprises substantially pure sense or antisense mRNA transcribed from the above-described DNAs, wherein the DNAs encode substantially pure functional proteins that have electrophysiological and pharmacological properties characteristic of a glutamate receptor.

In still another aspect, the invention comprises Xenopus oocytes to which mRNA of the invention has been introduced, e.g., by injection.

Still further, the invention comprises novel glutamate receptors made by expression of DNAs of the invention, or translation of the corresponding mRNAs. Such novel receptors include the individual GluR1, GluR2, GluR3, GluR4, GluR5, GluR6 and GluR7 receptors, fragments thereof, plus functional combinations of the receptors or fragments.

Still further, the invention comprises DNA, RNA and proteins that are functionally equivalent to the DNAs, RNAs and proteins of the present invention. Such functionally equivalent DNAs, RNAs and proteins will function in substantially the same manner as the DNAs, RNAs and proteins of the invention.

Presently preferred proteins of the invention, or functional fragments thereof, or functional combinations of these proteins and/or fragments, are proteins or functional fragments or functional combinations thereof which have electrophysiological and pharmacological properties characteristic of KA and/or AMPA glutamate receptor subtypes.

The invention proteins, or functional fragments thereof, or functional combinations of the proteins and/or the fragments, can be characterized as being encoded by DNA having at least about 40% nucleic acid homology with at least one member of the group consisting of GluR1 DNA (see, for example, Sequence ID No. 1), GluR2 DNA (see, for example, Sequence ID No. 3), GluR3 DNA (see, for example, Sequence ID No. 5), GluR4 DNA (see, for example, Sequence ID No. 7), GluR5 DNA (see, for example, Sequence ID No. 9), GluR6 DNA (see, for example Sequence ID No. 11) and GluR7 DNA (see, for example, Sequence ID No. 13), as well as substantially pure functional proteins having substantial sequence homology with the substantially pure functional proteins of the invention.

The phrase "substantial sequence homology", as used in the present specification and claims, means that the DNA, RNA or amino acid sequences which have slight and non-consequential sequence variations from the actual sequences disclosed and claimed herein are considered to be equivalent to the sequences of the present invention, and as such are within the scope of the appended claims. In this regard, "slight and non-consequential sequence variations" mean that "homologous" sequences (i.e., the sequences that have substantial sequence homology with the DNA, RNA, or proteins disclosed and claimed herein) will be functionally equivalent to the sequences disclosed and claimed in the present invention. Functionally equivalent sequences will function in substantially the same manner to produce substantially the same compositions as the nucleic acid and amino acid compositions disclosed and claimed herein.

Alternatively, the invention proteins, or functional fragments thereof, or functional combinations of the proteins and/or the fragments can be characterized as receptors which have at least about 40% overall amino acid homology with at least one member of the group consisting of GluR1 (see, for example, Sequence ID No. 2), GluR2 (see, for example, Sequence ID No. 4), GluR3 (see, for example, Sequence ID No. 6), GluR4 (see, for example, Sequence ID No. 8), GluR5 (see, for example, Sequence ID No. 10), GluR6 (see, for example, Sequence ID No. 12) and GluR7 (see, for example, Sequence ID No. 14), as well as substantially pure functional proteins having substantial sequence homology with the substantially pure functional proteins of the invention.

Presently preferred receptor proteins of the invention, or functional fragments thereof, or functional combinations of such proteins and/or fragments are characterized as receptors having at least about 50% amino acid homology in the C-terminal domain thereof with the C-terminal domain of at least one member of the group consisting of GluR1 (see, for example, Sequence ID No. 2), GluR2 (see, for example, Sequence ID No. 4), GluR3 (see, for example, Sequence ID No. 6), GluR4 (see, for example, Sequence ID No. 8), GluR5 (see, for example, Sequence ID No. 10), GluR6 (see, for example, Sequence ID No. 12) and GluR7 (see, for example, Sequence ID No. 14), as well as substantially pure functional proteins having substantial sequence homology with the substantially pure functional proteins of the invention.

Exemplary receptors of the invention comprise substantially pure proteins selected from GluR1, GluR2, GluR3, GluR4, GluR5, GluR6 and GluR7, and combinations thereof wherein said combinations are functional as glutamate receptor(s).

As used herein, GluR1 refers to a cDNA clone which encodes a single glutamate receptor subunit protein of the same name having a $M_r$ (of the non-glycosylated receptor) of approximately 99.8 kilodaltons (kD). GluR1 was the first glutamate receptor subunit encoding cDNA to be isolated; it was previously referred to as GluR-K1. GluR-K1 has been renamed glutamate receptor subunit gene 1 or, more simply, GluR1. Additional glutamate receptor subunits or subunit related genes are called GluR2, GluR3, GluR4, GluR5, GluR6, GluR7 and so forth. GluR1 cDNA was deposited with the American Type Culture Collection on Oct. 19, 1989; and has been accorded ATCC Accession No. 68134.

As used herein GluR2 refers to a cDNA clone which encodes a single glutamate receptor subunit protein of the same name having a $M_r$ (of the non-glycosylated receptor) of approximately 96.4 kD. GluR2 cDNA was deposited with the American Type Culture Collection on Oct. 19, 1989; and has been accorded ATCC Accession No. 68132.

As used herein, GluR3 refers to a cDNA clone which encodes a single glutamate receptor subunit protein of the same name having a $M_r$ (of the non-glycosylated receptor) of approximately 98.0 kD. GluR3 cDNA was deposited with the American Type Culture Collection on Oct. 19, 1989; and has been accorded ATCC Accession No. 68133.

As used herein, GluR4 refers to a cDNA clone which encodes a single protein of the same name having a $M_r$ (of the non-glycosylated receptor) of approximately 98.5 kD. GluR4 cDNA was deposited with the American Type Culture Collection on Aug. 2, 1990; and has been accorded ATCC Accession No. 68375.

As used herein, GluR5 refers to a GluR5 cDNA clone which encodes a single protein of the same name having a $M_r$ (of the non-glycosylated receptor) of approximately 100 kD. GluR5 cDNA (as GluR5-1) was deposited with the American Type Culture Collection on Aug. 2, 1990; and has been accorded ATCC Accession No. 68374. There are two length variants of GluR5 cDNA, referred to herein as GluR5-1 and GluR5-2. Translation of the GluR5 cDNAs predicts a single long open reading frame of 920 amino acids. The difference between GluR5-1 and GluR5-2 DNA derives from an insertion of 45 nucleotides (15 amino acids) in the GluR5-1 DNA which does not interrupt this reading frame. The 15 amino acid insertion in the GluR5-1 receptor protein is unique among the receptor proteins disclosed herein; thus the shorter GluR5-2 variant is the counterpart of the GluR1, GluR2, GluR3, GluR4, GluR6 and GluR7 subunits.

As used herein, GluR6 refers to a cDNA clone which encodes a single protein of the same name having a $M_r$ (of the non-glycosylated receptor) of approximately 100 kD.

As used herein, GluR7 refers to a cDNA clone which encodes a single protein of the same name having a $M_r$ (of the non-glycosylated receptor) of approximately 100 kD.

As used herein, GluR1, GluR2, GluR3, GluR4, GluR5, GluR6 and GluR7 are each used interchangeably to refer to genes, cDNA clones and the glutamate receptor proteins they encode.

Presently preferred receptors of the invention comprise substantially pure proteins having $M_r$s (of the non-glycosylated receptor) of about 99.8 kD (GluR1), 96.4 kD (GluR2), 98.0 kD (GluR3), 98.5 kD (GluR4), 100 kD (GluR5), 100 kD (GluR6), and 100 kD (GluR7), as well as channels which possess the electrophysiological and pharmacological properties characteristic of glutamate receptors of the KA and/or AMPA subtypes.

In accordance with yet another embodiment of the present invention, there are provided antibodies generated against the above-described receptor proteins. Such antibodies can be employed for diagnostic applications, therapeutic applications, and the like. Preferably, for therapeutic applications, the antibodies employed will be monoclonal antibodies.

The above-described antibodies can be prepared employing standard techniques, as are well known to those of skill in the art, using the invention receptor proteins as antigens for antibody production.

In accordance with still another embodiment of the present invention, there are provided methods for modulating the ion channel activity of receptor(s) of the invention by contacting said receptor(s) with an effective amount of the above-described antibodies.

The antibodies of the invention can be administered to a subject employing standard methods, such as, for example, by intraperitoneal, intramuscular, intravenous, or subcutaneous injection, implant or transdermal modes of administration, and the like. One of skill in the art can readily determine dose forms, treatment regiments, etc, depending on the mode of administration employed.

The invention DNA can be characterized as comprising substantially pure DNA having at least about 50% overall nucleic acid homology with at least one member of the group consisting of GluR1 DNA, GluR2 DNA, GluR3 DNA, GluR4 DNA, GluR5 DNA, GluR6 DNA and GluR7 DNA.

Alternatively, the invention DNA comprises substantially pure DNA encoding proteins having at least about 40% overall amino acid homology with at least one member of the group consisting of GluR1 (see, for example, Sequence ID No. 2), GluR2 (See, for example, Sequence ID No. 4), GluR3 (see, for example, Sequence ID No. 6) GluR4 (see, for example, Sequence ID No. 8), GluR5 (see, for example, Sequence ID No. 10), GluR6 (see, for example, Sequence ID No. 12), and GluR7 (see, for example, Sequence ID No. 14).

Presently preferred DNA are substantially pure DNA encoding substantially pure proteins having $M_r$s (of the non-glycosylated receptor) of about 99.8 kD (GluR1), 96.4 kD (GluR2), 98.0 kD (GluR3), 98.5 kD (GluR4), 100 kD (GluR5), 100 kD (GluR6), and 100 kD (GluR7), as well as combinations thereof that form ion channels which possess the electrophysiological and pharmacological properties characteristic of a glutamate receptor of the KA and/or AMPA subtypes.

Especially preferred DNA sequences of the invention comprise substantially pure DNA selected from GluR1 DNA (see, for example, Sequence ID No. 1), GluR2 DNA (see, for example, Sequence ID No. 3), GluR3 DNA (see, for example, Sequence ID No. 5), GluR4 DNA (see, for example, Sequence ID No. 7), GluR5 DNA (see, for example, Sequence ID No. 9), GluR6 DNA (see, for example, Sequence ID No. 11) and GluR7 DNA (see, for example, Sequence ID No. 13).

Also contemplated by the present invention are substantially pure DNA that are functionally equivalent to any of the substantially pure DNAs of the invention, wherein functionally equivalent means that the substantially pure DNA will encode proteins, or functional fragments thereof, which will form ion channel(s) in response to ligands for glutamate receptors.

Representative clones of the above-described DNA sequences have been deposited with the American Type Culture Collection. The representative cDNA clones include: GluR1 (ATCC No. 68134), GluR2 (ATCC No. 68132), GluR3 (ATCC No. 68133), GluR4 (ATCC No. 68375), and GluR5 (ATCC No. 65374).

Either the full length cDNA clones or fragments thereof can be used as probes, preferably labeled with suitable label means for ready detection. When fragments are used as probes, preferably the DNAs will be from the carboxyl encoding portion of the DNA, and most preferably will include ion channel encoding portions of the DNA. These probes can be used, for example, for the identification and isolation of additional members of the glutamate receptor family.

In another aspect, the invention comprises functional peptide fragments, and functional combinations thereof, encoded by the DNAs of the invention. Such functional peptide fragments can be produced by those skilled in the art, without undue experimentation, by eliminating some or all of the amino acids in the sequence not essential for the peptide to function as a glutamate receptor. A determination of the amino acids that are essential for glutamate receptor function is made, for example, by systematic digestion of the DNAs encoding the peptides and/or by the introduction of deletions into the DNAs. The modified (e.g., deleted or digested) DNAs are expressed, for example, by transcribing the DNA and then introducing the resulting mRNA into Xenopus oocytes, where translation of the mRNAs will occur. Functional analysis of the proteins thus expressed in the oocytes is accomplished by exposing the oocytes to ligands known to bind to and functionally activate glutamate receptors, and then monitoring the oocytes to see if the expressed fragments form ion channel(s). If ion channel(s) are detected, the fragments are functional as glutamate receptors.

In addition to DNA, RNA and protein compositions of matter, several novel methods are contemplated by the present invention. The first is a method for identifying DNA that is homologous to DNA known to encode glutamate receptor protein(s). This method comprises contacting an "unknown" or test sample of DNA with a glutamate receptor DNA probe (e.g., GluR1, GluR2, GluR3, GluR4, GluR5, GluR6, GluR7, etc.) under suitable hybridization conditions, and then identifying "unknown" or test DNA which hybridizes with the glutamate probe DNA as glutamate receptor homologous DNA.

Such screening is initially carried out under low-stringency conditions, which comprise a temperature of about 37° C. or less, a formamide concentration of less than about 50%, and a moderate to low salt (SSC) concentration; or, alternatively, a temperature of about 50° C. or less, and a moderate to high salt (SSPE) concentration. Presently preferred conditions for such screening comprise a temperature of about 37° C., a formamide concentration of about 20%, and a salt concentration of about 5× standard saline citrate (SSC; 20× SSC contains 3M sodium chloride, 0.3M sodium citrate, pH 7.0); or a temperature of about 50° C., and a salt concentration of about 2× SSPE (1× SSPE contains 180 mM NaCl, 9 mM $Na_2HPO_4$, 0.9 mM $NaH_2PO_4$ and 1 mM EDTA, pH 7.4). Such conditions will allow the identification of sequences which have a substantial degree of similarity with the probe sequence, without requiring perfect homology for the identification of a stable hybrid. The phrase "substantial similarity" refers to sequences which share at least 50% overall sequence identity. Preferably, hybridization conditions will be selected which allow the identification of sequences having at least 70% sequence identity with the probe, while discriminating against sequences which have a lower level of sequence identity with respect to the probe.

After low stringency hybridization has been used to identify several clones having a substantial degree of similarity with the probe sequence, this subset of clones is then subjected to high stringency hybridization, so as to identify those clones having particularly high level of homology with respect to the probe sequences. High stringency conditions comprise a temperature of about 42° C. or less, a formamide concentration of less than about 20%, and a low salt (SSC) concentration; or, alternatively, a temperature of about 65° C. or less, and a low salt (SSPE) concentration. Presently preferred conditions for such screening comprise a temperature of about 42° C., a formamide concentration of about 20%, and a salt concentration of about 2× SSC; or a temperature of about 65° C., and a salt concentration of about 0.2× SSPE.

Another method of the invention is directed to identifying functional glutamate receptors (i.e., glutamate receptors that form ion channels). This method comprises contacting glutamate receptor proteins, preferably in an oocyte expression system, with at least one ligand known to activate such receptors, measuring ion channel response to the ligand(s), and identifying as functional glutamate receptor(s) those proteins which exhibit an ion channel response as a consequence of the contact.

In accordance with a further embodiment of the present invention, there is provided a binding assay employing receptors of the invention, whereby a large number of compounds can be rapidly screened to determine which compounds, if any, are capable of binding to glutamate receptors. Subsequently, more detailed assays can be carried out with those compounds found to bind, to further determine whether such compounds act as modulators, agonists or antagonists of invention receptors.

Another application of the binding assay of the invention is the assay of test samples (e.g., biological fluids) for the presence or absence of receptors of the present invention. Thus, for example, serum from a patient displaying symptoms related to glutamate pathway dysfunction can be assayed to determine if the observed symptoms are perhaps caused by over- or under-production of such receptor(s).

The binding assays contemplated by the present invention can be carried out in a variety of ways, as can readily be identified by one of skill in the art. For example, competitive binding assays can be employed, as well as radioimmunoassays, ELISA, ERMA, and the like.

Yet another method of the invention involves determining whether a substance is a functional ligand for glutamate receptor protein (i.e., a modulator, an agonist or an antagonist of glutamate receptor(s)). According to this method, proteins known to function as glutamate receptors are contacted with an "unknown" or test substance (in the further presence of a known glutamate agonist, when antagonist activity is being tested), the ion channel activity of the known glutamate receptor is monitored subsequent to the contact with the "unknown" or test substance, and those substances which increase or decrease the ion channel response of the known glutamate receptor(s) are identified as functional ligands (i.e., modulators, agonists or antagonists) for receptor proteins.

As yet another application of the invention sequences, genetic screening can be carried out using the nucleotide sequences of the invention as probes. Thus, patients having neuropathological conditions suspected of involving alteration/modification of any one or more of the glutamate receptors can be screened with appropriate probes to determine if any abnormalities exist with respect to any of the endogenous glutamate receptors. Similarly, patients having a family history of disease states related to glutamate receptor dysfunction can be screened to determine if they are also predisposed to such disease states.

Turning now to some of the specific DNAs of the invention, cDNA clone GluR1 was isolated from a rat forebrain cDNA library by screening for expression of kainate-gated ion channels in Xenopus oocytes. An insert from clone GluR1 was used as a probe to screen cDNA brain libraries (first under low-stringency hybridization conditions and then under higher stringency conditions) in order to find cDNA clones that encode other members of the glutamate receptor family. Use of the GluR1 probe cDNA led to the identification and isolation of the GluR2 and GluR3 clones. A probe from GluR2 was used to identify and isolate clones GluR4 and GluR5, and GluR5 was used to isolate clones for GluR6 and GluR7.

cDNA clone GluR1 encodes a functional glutamate receptor subunit which consists of a single protein having a $M_r$ (of the non-glycosylated receptor) of about 99.8 kD, before any post-translational modifications. This protein forms an ion channel which possesses the electrophysiological and pharmacological properties of KA and AMPA receptors.

The proteins encoded by the GluR1, GluR2, GluR3, GluR4, GluR5, GluR6 and GluR7 genes exhibit considerable inter-subunit amino acid sequence identity, as summarized in Table 1.

GluR6 forms homomeric ion channels which are responsive to KA, but not to AMPA.

The GluR5 protein in Xenopus oocytes forms a homomeric ion channel which is weakly responsive to glutamate but not to N-methyl-D-aspartate, kainate, quisqualate and 2-amino-4-phosphonobutyrate. The fact that oocytes expressing GluR5 are responsive to L-glutamate but not to KA, quisqualate or AMPA indicates that this protein can participate in the formation of receptors with a different pharmacological profile than the KA/AMPA subunits.

During embryonic and postnatal development the GluR5 gene is expressed in subsets of neuronal cells in the central nervous system (CNS) and the peripheral nervous system (PNS). The spatial and temporal expression pattern of the GluR5 gene is largely overlapping with the KA/AMPA subunit GluR4. However, in adult brains, the GluR5 gene is expressed in a pattern distinct from those of the KA/AMPA subunit genes, consistent with GluR5 being a subtype of glutamate receptors different from the KA/AMPA receptors.

DEPOSITS cDNA clones encoding representative glutamate receptor protein subunits of the present invention have been deposited with the American Type Culture Collection, Rockville, Md., U.S.A. (ATCC). The deposits

TABLE 1

The Percent Amino Acid Sequence Indentity Among Pairwise Combination of Members of the Glutamate Receptor Subunit Gene Family

| | GluR1 | GluR2 | GluR3 | GluR4 | GluR5 | GluR6 | GluR7 |
|---|---|---|---|---|---|---|---|
| A. N-terminal domain | | | | | | | |
| GluR1 | 100 | 58 | 57 | 55 | 34 | 33 | 33 |
| GluR2 | | 100 | 62 | 62 | 33 | 33 | 33 |
| GluR3 | | | 100 | 64 | 34 | 34 | 32 |
| GluR4 | | | | 100 | 32 | 31 | 31 |
| GluR5 | | | | | 100 | 75 | 70 |
| GluR6 | | | | | | 100 | 77 |
| GluR7 | | | | | | | 100 |
| B. C-terminal domain | | | | | | | |
| GluR1 | 100 | 86 | 84 | 84 | 49 | 51 | 48 |
| GluR2 | | 100 | 89 | 88 | 49 | 51 | 50 |
| GluR3 | | | 100 | 87 | 51 | 54 | 50 |
| GluR4 | | | | 100 | 51 | 52 | 48 |
| GluR5 | | | | | 100 | 89 | 79 |
| GluR6 | | | | | | 100 | 87 |
| GluR7 | | | | | | | 100 |
| C. Overall amino acid sequence identity | | | | | | | |
| GluR1 | 100 | 70 | 69 | 68 | 40 | 41 | 39 |
| GluR2 | | 100 | 73 | 72 | 40 | 41 | 40 |
| GluR3 | | | 100 | 73 | 41 | 42 | 40 |
| GluR4 | | | | 100 | 41 | 40 | 39 |
| GluR5 | | | | | 100 | 80 | 78 |
| GluR6 | | | | | | 100 | 79 |
| GluR7 | | | | | | | 100 |

The sequences were compared using sequence analysis software from the University of Wisconsin Genetics Computer Group [Devereux et al., Nucl. Acids Res. 12:387 (1984)]. The percent sequence identity between paired sequences was calculated by dividing the number of aligned positions with identical amino acids by the total number of aligned positions in the shortest of the sequences examined and multiplying the quotient by 100.

These proteins have been found to form distinct homomeric and heteromeric KA/AMPA-sensitive ion channels in Xenopus oocytes. For example, single protein subunits of glutamate receptors, GluR1, GluR2, GluR3, GluR4 and GluR5 are sufficient to form homomeric functional receptor ion-channel complexes activated by KA, AMPA, and QUIS but not by NMDA and APB. While GluR2 subunits can form functional homomeric complexes, this subunit more efficiently assembles receptor-ion channel complexes in heteromeric combination with GluR1 or GluR3 subunits.

have been made under the terms of the Budapest Treaty on the International Recognition of Deposits of Microorganisms for Purposes of Patent Procedure and the Regulations promulgated under this Treaty. Samples of the cloned DNA sequences are and will be available to industrial property offices and other persons legally entitled to receive them under the terms of the Treaty and Regulations and otherwise in compliance with the patent laws and regulations of the United States of America and all other nations or international organizations in which this application, or an application claiming priority of this application, is filed or in which any patent granted on any such application is granted.

Without further elaboration, one of ordinary skill in the art can, using the preceding description, and the following Examples, utilize the present invention to its fullest extent. The material disclosed in the examples is disclosed for illustrative purposes and therefore should not be construed as being limiting in any way of the appended claims.

EXAMPLES

As used herein, bp means base pairs. Kbp means kilobase pairs, or 1000 base pairs.

As used herein, all temperatures are given in degrees Centigrade unless indicated otherwise.

EXAMPLE I

Production of Brain cDNA Libraries

Poly(A)+ RNA from various regions of the brain, e.g., mammalian brain, or a suitable cell line, e.g., the NCB-20 cell line, is purified by the guanidine thiocyanate-CsCl method [Chirgwin et al., Biochem 18:5294 (1979)]. The purified RNA is used as a template to prepare double strand cDNA. A poly-dT primer linked to a XhoI restriction site is used as a primer to prime the Moloney reverse transcriptase for the synthesis of the first strand using 5-methyl dCTP instead of cCTP as a precursor. RNaseH and DNA polymerase I are added to complete the second strand. The cDNA is blunt-ended with T4 DNA polymerase which increases the chance of making a full-length cDNA. EcoRI adapters are ligated to the blunt-end and the ends are kinased. The cDNA is then digested with the restriction enzyme, XhoI. This enzyme only cleaves the unmethylated XhoI restriction site attached to the dT-primer at the 3' end of the mRNA. The resulting double stranded cDNA has a XhoI restriction site at the 3' end of the mRNA and an EcoRI site at the 5' end. This cDNA is then placed into an appropriate vector, such as λZAP vector, which is part of the λZAP-cDNA cloning system from Stratagene. When the λZAP vector is used, the cDNA is placed into the vector so that the 5' end of the mRNA is near the lacZ promoter. The λZAP vector has a T3 RNA polymerase promoter at one end of the cDNA insert and a T7 RNA polymerase promoter at the other end which makes it possible to synthesize either sense or antisense RNA for further experiments, including expression in oocytes.

EXAMPLE II

Low and High Stringency Hybridization cDNA libraries are preferably made with the λZAP-cDNA system described in Example I. A hybridization probe is preferably made from DNA obtained from GluR1, GluR2, GluR3, GluR4, GluR5, GluR6 or GluR7 clones or another suitable clone or source. The DNA is labeled by the random prime method, preferably using the Amersham Multiprime DNA labeling kit (Amersham Corporation, Chicago, Ill.). Preferably, low stringency hybridization conditions are used, at least at first. A suitable hybridization solution is as follows:
1 M NaCl, 50 mM Tris [pH 8.0],
0.5% SDS, 0.1% sodium pyrophosphate,
100 mg/ml denatured herring sperm DNA, 0.1% [w/v] each of Ficoll, polyvinylpyrrolidone and bovine serum albumin.

For low stringency screening, a temperature of 50° C. is preferable, and library filters are washed in 2× SSPE (wherein 1× SSPE is 180 mM NaCl, 9 mM Na$_2$HPO$_4$, 0.9 mM NaH$_2$PO$_4$ and 1 mM EDTA, pH 7.4) at room temperature and exposed to Kodak XAR-5 film at −70° C.

Under these low-stringency hybridization conditions, about one in two thousand brain cDNA clones show some hybridization to the probe made from the glutamate receptor cDNA insert.

For high stringency screening, the temperature is adjusted to 65° C. and the filters are washed at this temperature in 0.2× SSPE containing 0.5% sodium dodecyl sulfate. Filters are exposed to Kodak XAR-5 film with Cronex Quanta II/III intensifying screens at −70° C. for 18–48 hours.

EXAMPLE III

Analysis of Clones Identified by Hybridization

At least two different approaches can be used to analyze clones that are identified by low-stringency hybridization screening. One approach is to pick positive λZAP clones and pool them into mixtures of about 100 clones. mRNA is made in vitro from these pools of λZAP clones and the mRNA is injected into oocytes in order to test the ability of the mRNA to direct synthesis of functional glutamate receptors. If a positive clone is found, the individual λZAP cDNA clone is isolated by subdividing the pool until the functional clone is isolated. (See Example V, below, for a discussion of how this approach was used to isolate the GluR1 clone.)

A second approach that can be used to evaluate positive clones is to analyze each insert individually. Although this is tedious, the "individual clone" approach has the advantage that initially it does not require functional expression. When the "individual clone" approach is used, each clone is plaque purified and the cDNA insert is analyzed individually. This is facilitated by the fact that, at least in the λZAP cDNA system, the cDNA is cloned into a cassette flanked by the bacteriophage f1 origin of replication. The cDNA is contained within a pBluescript plasmid which can be rescued from the λZAP bacteriophage by helper infection. Once this is done, the cDNA is in the small pBluescript plasmid (which is much easier to work with than the much larger λ-bacteriophage). Sense or antisense RNA is made from the cDNA insert in the pBluescript plasmid using either the T3 (sense) or T7 (anti-sense) promoter.

cDNA inserts can also be analyzed by mapping with restriction enzymes. For example, the cDNA inserts are cut with frequent cutting restriction enzymes, and the resulting fragments size fractionated on a gel. Subsequently, the fragments are transferred to a filter for Southern blot analysis. The filters are hybridized with a probe made from DNA encoding known glutamate receptor subunits, e.g., GluR1, GluR2, GluR3, GluR5, GluR5, GluR6 or GluR7. The hybridizing fragments from each clone are subcloned into the single-stranded vector M13 (mp18 or mp19), and the fragments sequenced. DNA sequencing is performed using standard techniques, such as the dideoxynucleotide chain termination method of Sanger et al. Proc. Natl. Acad. Sci. USA 74:5463 (1977), or an automatic sequencer such as one manufactured by Applied Biosystems. The sequence is preferably analyzed by computer using software such as the programs developed by Intelligenetics, Staden and the University of Wisconsin.

mRNA made from full-length or nearly full-length clones are expressed in the oocyte system and the functional properties of the new receptors are characterized. If a clone is not functional when expressed by itself, it is tested in the presence of mRNA made from other candidate clones.

EXAMPLE IV

Expression Cloning and Assay in Xenopus Oocytes

This assay is an adaptation of the assay of Masu et al., Nature 329:836 (1987). It depends upon the fact that when foreign mRNA is injected into Xenopus oocytes, the mRNA is translated into functional protein.

Either a λZAP cDNA preparation, or a plasmid containing the cDNA to be tested, are cut downstream from the cDNA insert with a restriction enzyme. The post-restriction digest is digested with Proteinase K and then extracted with two phenol: chloroform (1:1) extractions. The resulting DNA fragments are then ethanol precipitated. The precipitated fragments are mixed with either T3 RNA polymerase (to make sense strand), or T7 RNA polymerase (to make anti-sense strand), plus rATP, rCTP, rGTP, rUTP, and RNase inhibitor. Simultaneously, the RNA transcripts are capped with a sodium diguanosine triphosphate [G(5')ppp(5')G] cap. The water used for the above procedures is treated with diethylpyrocarbonate to inactivate RNases.

The in vitro synthesized mRNA transcripts are injected into Xenopus oocytes. 50 nl of an RNA solution, 0.2–0.6 mg/ml, is injected into the stage V oocytes. The injected oocytes are incubated at 16° C. in Barth's medium for 2–7 days before they are analyzed for the presence of functional receptors.

Voltage recordings are made by penetrating the oocyte with a micro-electrode filled with 3M KCl and connected to the bridge circuit of an appropriate voltage clamp unit, e.g., the Dagan 8500 voltage clamp unit. Voltage recordings are preferably obtained with two electrodes, a voltage electrode filled with 3M KCl and a current electrode filled with 0.25 M CsCl, 0.25 M CsF and 50 mM EGTA (ethylene glycol tetraacetic acid). Example VI provides a discussion of results of recordings from oocytes injected with RNA from GluR1 cDNA encoding a KA/AMPA glutamate receptor.

Oocytes employed herein are obtained from ovarian tissue from anesthetized adult female Xenopus. The ovarian tissue is treated with collagenase, 2 mg/ml, for two hours and then the ovarian epithelium and follicular cells are dissected away.

EXAMPLE V

Expression Cloning of the GluR1 Receptor

Xenopus oocytes were injected with poly(A)+ RNA isolated from rat forebrain. 2–10 days later, the oocytes were tested electrophysiologically for their ability to respond to selective agonists for glutamate receptor subtypes. Both glutamate and quisqualate induce membrane depolarizations. These responses display a biphasic pattern composed of a fast acting, smooth (presumably ligand-gated ion channel) response, and a longer lasting, fluctuating, (probably second-messenger mediated) response. NMDA and KA elicited smooth responses with fast onsets, while APB gave no response.

A directional cDNA library (λZAPII RTB1; complexity: $8 \times 10^5$ elements), consisting of 18 independent sublibraries of 44,000 clones each, was constructed from this poly(A)+ RNA using the bacteriophage expression vector λZAPII. A pool of in vitro transcripts, comprised of transcripts made separately from all 18 amplified sublibraries, was injected into oocytes. Small depolarizations (1–3 mV) were seen in voltage recordings from oocytes challenged with 100 µM kainate 10 days after injection. No responses to NMDA or quisqualate were detected. Neither uninjected oocytes nor water-injected oocytes showed any responses to glutamate receptor agonists. Subsequently, pools of 44,000 clones (=the single sublibraries), 4,000, 400 and 40 clones were tested. In each of these tests at least one pool responded to KA.

The following criteria were used throughout the screening procedure to assure that the very small responses observed initially were not recording artifacts: (a) responses in a given oocyte were reproducible, (b) responses were fast (within one second of agonist application), (c) responses were readily reversible upon superfusion of the oocyte with control Ringer solution, (d) 10 µM domoate gave a response similar to the one elicited by 100 µM kainate.

The pools yielding the largest responses at each stage were selected for further subdivision. The clones in the final positive pool of 40 clones were analyzed for their insert size, and the 12 clones with the largest inserts (all >2 kb) were tested individually for their ability to direct the synthesis of a functional kainate receptor. Only one clone, carrying a 3.0 kb insert, was found to elicit kainate responses and was named λZAPII-GluR1.

EXAMPLE VI

Electrophysiological and Pharmacological Characterization of the GluR1 Clone

The plasmid pGluR1 was subsequently rescued from bacteriophage λZAPII-GluR1. Upon transcription and translation in vitro, the translation product of sense RNA (but not antisense RNA) induced kainate responses when injected into oocytes. The GluR1 translation product from as little as 10 pg of GluR1 sense transcript gave detectable responses to 100 µM KA under voltage-clamp conditions ($-70$ mV holding potential).

In order to rule out the possibility that GluR1 codes for a transcription factor, oocytes injected with pGluR1 in vitro transcripts were kept in medium supplemented with 50 µg/ml actinomycin D to inhibit endogenous transcription. These oocytes exhibited the same responses to kainate as those kept in control medium. Therefore, injection-induced transcription from the oocyte genome does not contribute to the observed responses.

L-glutamate evoked much smaller responses than did KA, and even at 1 mM elicited only 50% of the depolarization seen with 30 µM KA. This is consistent with the observation that glutamate is only a weak agonist for the KA receptor subtype [Monaghan et al., Nature 306:176 (1983)]. Other glutamate receptor agonists such as NMDA, quisqualate and L-aspartate evoked no responses when applied at 150 µM, 10 µM, and 100 µM, respectively. Unrelated neurotransmitter receptor agonists such as glycine, γ-aminobutyric acid (GABA$_A$), serotonin and nicotine also failed to evoke responses, even when tested at concentrations as high as 1 mM. Glycine did not potentiate the KA response. Dose-response curves for KA and domoate were recorded and EC$_{50}$ values of 39 μM and 1.8 μM, respectively, were derived. The average reversal potential was 10 mV, as extrapolated from current responses to 10 μM kainate obtained at a series of holding potentials between 0 and −130 mV. Responses to KA did not desensitize, even after prolonged (up to 10 minutes) superfusion with high concentrations (100 μM) of agonist.

Similarly, the pharmacological profile of GluR1, as revealed by the inhibiting properties of various known glutamate receptor antagonists (see Table 2), is consistent with previous reports for KA receptors in systems where total poly(A)+ RNA was used as a source of kainate receptor message [Hirono et al., Neurosci. Res. 6:106 (1988); Lerma et al., Proc. Natl. Acad. Sci. USA 86:2083 (1989)].

As used herein, the term antagonist refers to a substance that interferes with receptor function. Antagonists are of two types: competitive and non-competitive. A competitive antagonist (also known as a competitive blocker) competes with an agonist for overlapping binding sites. A non-competitive antagonist or blocker inactivates the functioning of the receptor by binding to a site on the receptor other than the agonist binding site.

TABLE 2

Pharmacology of the Glutamate Receptor Encoded by GluR1: Properties of various Glutamate Receptor Antagonists as Measured in Oocytes Injected With GluR1 in vitro RNA[a]

| Compound Tested[b] | Compound Alone (%)[c] | Compound Plus Kainate (%)[d] |
|---|---|---|
| kainate (agonist control) | 100.0 | 100.0 |
| Kynurenic acid | 3.4 ± 0.2 | 9.6 ± 1.3 |
| γ-DGG | −0.1 ± 0.5 | 30.8 ± 1.1 |
| GAMS | 1.0 ± 0.6 | 30.7 ± 1.1 |
| GDEE | 24.8 ± 5.7 | 97.8 ± 6.6 |
| PDA | 2.5 ± 0.7 | 31.3 ± 2.0 |
| APV | 3.1 ± 1.4 | 73.7 ± 3.2 |
| CPP | 9.1 ± 0.7 | 78.8 ± 0.9 |

[a]Oocytes had been injected with 1.25 ng of GluR1 in vitro sense RNA 3 days prior to the recording. The oocytes were voltage-clamped at −70 mV, and the test compounds (all at 1 Mm, except kainate, which was 30 μM) applied by rapid superfusion, with 5 minute intervals between drugs. Peak currents were recorded; each number represents the average of 3 recordings from 3 different oocytes, ± SEM. The 100% current response corresponds to 40-200 nA, depending on the oocyte.
[b]Abbreviations for the compounds used refer to:
γ-DGG means γ-D-glutamylglycine;
GAMS means γ-D-glutamylamino-methyl-sulphonate;
GDEE means glutamate diethyl-ester;
PDA means 2,3-cis-piperidine dicarboxylic acid;
APV means 2-amino-5-phospho-novaleric acid;
CPP means 3-(2-carboxypiperazin-4-yl)propyl-1-phosphate.
[c]% of the response evoked by 30 μM kainate immediately before drug application.
[d]% of the response seen with 30 μM kainate alone immediately before application of drug/kainate mixture Of all the compounds tested (each at 1 mM), the broad specificity glutamate receptor antagonist kynurenic acid clearly was the most potent inhibitor of the kainate-evoked depolarizations in oocytes injected with GluR1 RNA synthesized in vitro. To a lesser extent, γ-DGG, reported to preferentially block KA and NMDA receptors but not quisqualate receptors [Davies and Watkins, Brain Res. 206:173 (1981)], inhibited kainate responses, as did GAMS, which reportedly prefers KA and AMPA receptors [Fagg, Trends Neurosci. 8:207 (1985)]. Similarly, PDA, which is known to block all subtypes of glutamate receptors [Foster and Fagg, Brain Res. Rev. 7:103 (1984)], blocked the GluR1 response. GDEE, which is thought to preferentially inhibit AMPA-type glutamate receptors [Foster and Fagg, supra], did not block the response significantly, but instead displayed weak agonist properties. The NMDA receptor antagonists APV and CPP, as well as NMDA itself, slightly inhibited the KA responses, thus acting as weak antagonists. They did not show any agonist properties.

Taken together, the electrophysiological properties observed in oocytes injected with GluR1 transcript, as well as the observed pharmacological properties, indicate that GluR1 represents a functional KA receptor indistinguishable from the one observed in oocytes injected with total poly(A)+ RNA. Thus, the single protein subunit encoded by GluR1 is sufficient to form an active receptor-ion channel complex.

EXAMPLE VII

Sequencing and Primary Structure of GluR1

The cDNA insert of the plasmid pGluR1 was subcloned into M13mp19 and sequenced (see Sequence ID No. 1). An open reading frame of 2721 bp was found within the total length of 2992 bp. The predicted protein consists of 889 amino acids, with a calculated $M_r$(of the non-glycosylated form of the receptor subunit) of about 99.8 kD. The deduced protein sequence contains a putative signal peptide of 18 amino acids at its N-terminus, with a predicted cleavage site that conforms to empirical rules [von Heijne, Nucl. Acids Res. 14:4683 (1986)]. The N-terminus of the protein therefore is expected to be located extracellularly. Nucleotides 198 to 251 encode the putative signal peptide, and bases 1 through 197 represent a 5'-untranslated region. At the 3'-terminus of the clone, 71 nucleotides of untranslated sequence were found.

The deduced amino acid sequence for GluR1 is shown in Sequence ID No. 1, along with the nucleotide sequence. The numbering for the amino acid sequence starts with the first residue of the precursor protein, with the first residue of the mature protein being residue 19 (following cleavage of the putative signal sequence). Possible extracellular N-glycosylation sites are present at amino acid residues 63, 249, 257, 363, 401, and 406. The region between amino acids 107–131 bears some resemblance to the ligand-gated ion channel signature postulated by some workers [Grenningloh et al., Nature 330:25 (1987); Barnard et al., TINS 10:502 (1987)]. Sequence comparisons with other sequenced ligand-gated ion channels, the nicotinic acetylcholine receptors, GABA$_A$ receptors and glycine receptors, reveals little overall homology.

The insert cDNA of the bacteriophage clone λZAPII-GluR-K1 was cut out with EcoRI/XhoI, blunt-ended and subcloned into the SmaI-site of the bacteriophage vector M13mp19 [Messing et al., Proc. Natl. Acad Sci. USA 74:3642 (1977)], yielding clones with both orientations of the cDNA. Overlapping deleted subclones were constructed for each strand orientation using the Cyclone ™ kit from United States Biochemical Corporation (Cleveland, Ohio). Single-stranded sequencing by the dideoxynucleotide chain-termination method [Sanger et al., Proc. Natl. Acad. Sci. USA 74:5463 (1977)], was carried out with all 45 subclones, and additionally, 10 oligonucleotide primers were synthesized to facilitate sequencing across areas where compressions or gaps were encountered in the sequences derived from the deletion subclones. Complete sequences for both strands were thus obtained. IntelliGenetics software packages (IntelliGenetics version 5.0, and PC/Gene ™ (IntelliGenetics, Inc., Mountain View, Calif.) were used for analyzing sequences.

All ligand-gated ion channel subunits sequenced prior to the present invention have a conserved extracellular region characterized by 2 cysteine residues spaced 14 amino acids apart from each other, with conserved proline and aspartate residues located 8 and 10 amino acids, respectively, downstream from the first of these two cysteines [Barnard et al., Trends Neurosci. 10:502 (1987)]. This hypothetical signature for neurotransmitter receptor-channel complexes is poorly conserved in the protein encoded by GluR1. The proline and aspartate residues are present, but the first cysteine residue is located only 7 residues upstream from the proline residue, and the second cysteine residue is absent.

A hydropathy plot analysis of GluR1 revealed several regions which are candidates for transmembrane domains (TMDs). The region between amino acids 481 and 827 was notable because its hydropathy profile resembled that seen in the other ligand-gated ion channels: three closely spaced putative TMDs which are separated by ~175 amino acid residues from a fourth putative TMD which is located close to the C-terminus of the protein. Within this region, the following four transmembrane regions are assigned in GluR1: TMD I, located between amino acid residues 481 and 498, TMD II between residues 538 and 556, TMD III between residues 613 and 631, and TMD IV between residues 805 and 825.

FIG. 1a presents a comparison of the extracellular region located between amino acid residues 107 and 124 of GluR1 With the "cys-cys-loop" region found in all other ligand-gated ion channels, showing sequence homology. Sequences of neuronal nicotinic acetylcholine receptor (nAChR) subunits $\alpha 1, \beta 1, \gamma, \delta$ are from mouse muscle [Heinemann et al., Molecular Neurobiology: Recombinant DNA Approaches (ed. Heinemann, S. & Patrick, J.) 45-96 (Plenum Press, New York, 1987)], those of nAChR subunits $\alpha 2, \alpha 3, \alpha 4, \beta 2, \beta 3$, and $\beta 4$ are from rat brain [Deneris et al., J. Biol. Chem. 264:6268 (1989); Duvoisin et al., Neuron 3:487 (1989)]. $GABA_A$ subunits $\alpha$ and $\beta$ are from calf brain [Barnard et al., Trends Neurosci 10:502 (1987)]. GlyR 48k is the $M_r=48$ kDa subunit of the glycine receptor from rat brain [Grenningloh et al., Nature 328:215-220 (1987)]. Boxed amino acid residues are found at identical positions in GluR1 as well as in at least one of the other receptor sequences. One gap has been introduced arbitrarily.

FIG. 1b presents a comparison of the putative TMD II region of GluR1 with hypothetical TMD II regions of other ligand-gated ion channels [Barnard et al., Trends Neurosci. 10:502 (1987); Deneris et al., J. Biol. Chem. 264:6268 (1989); Duvoisin et al., Neuron 3:487 (1989); Grenningloh et al., Nature 328: 215 (1987); Heinemann et al., in: Molecular Neurobiology; Recombinant DNA Approaches (ed. Heinemann, S. & Patrick J.) 45-96 (Plenum Press, New York, (1987)]; suggesting protein sequence conservation.

EXAMPLE VIII

Isolation and Characterization of GluR2 and GluR3 cDNA clones encoding the GluR2 and GluR3 genes were isolated from an adult rat forebrain library using a low-stringency hybridization screening protocol (see Example II) and a radiolabeled fragment of the GluR1 cDNA as probe. Sequence ID Nos. 3 and 5 show the nucleotide and derived amino acid sequences of clones λRB14 (GluR2) and λRB312 (GluR3), respectively. The calculated molecular weights for the mature, nonglycosylated forms of GluR2 and GluR3 are 96,400 daltons (862 amino acids) and 98,000 daltons (866 amino acids), respectively. Potential N-linked glycosylation sites occur in the GluR2 protein at Asn-239, Asn-359, Asn-381, Asn-406, and Asn-851 and in the GluR3 protein at Asn-37, Asn-243, Asn-363, Asn-374, and Asn-394. Like GluR1, the hydrophobicity profile for both GluR2 and GluR3 reveals five strongly hydrophobic regions: one such domain is located at the amino terminus of each protein and has characteristics of a signal peptide, while four additional hydrophobic regions presumably form membrane-spanning regions (MSR I-IV) and are located in the carboxy-terminal domain of each polypeptide.

Figure 2A-4:
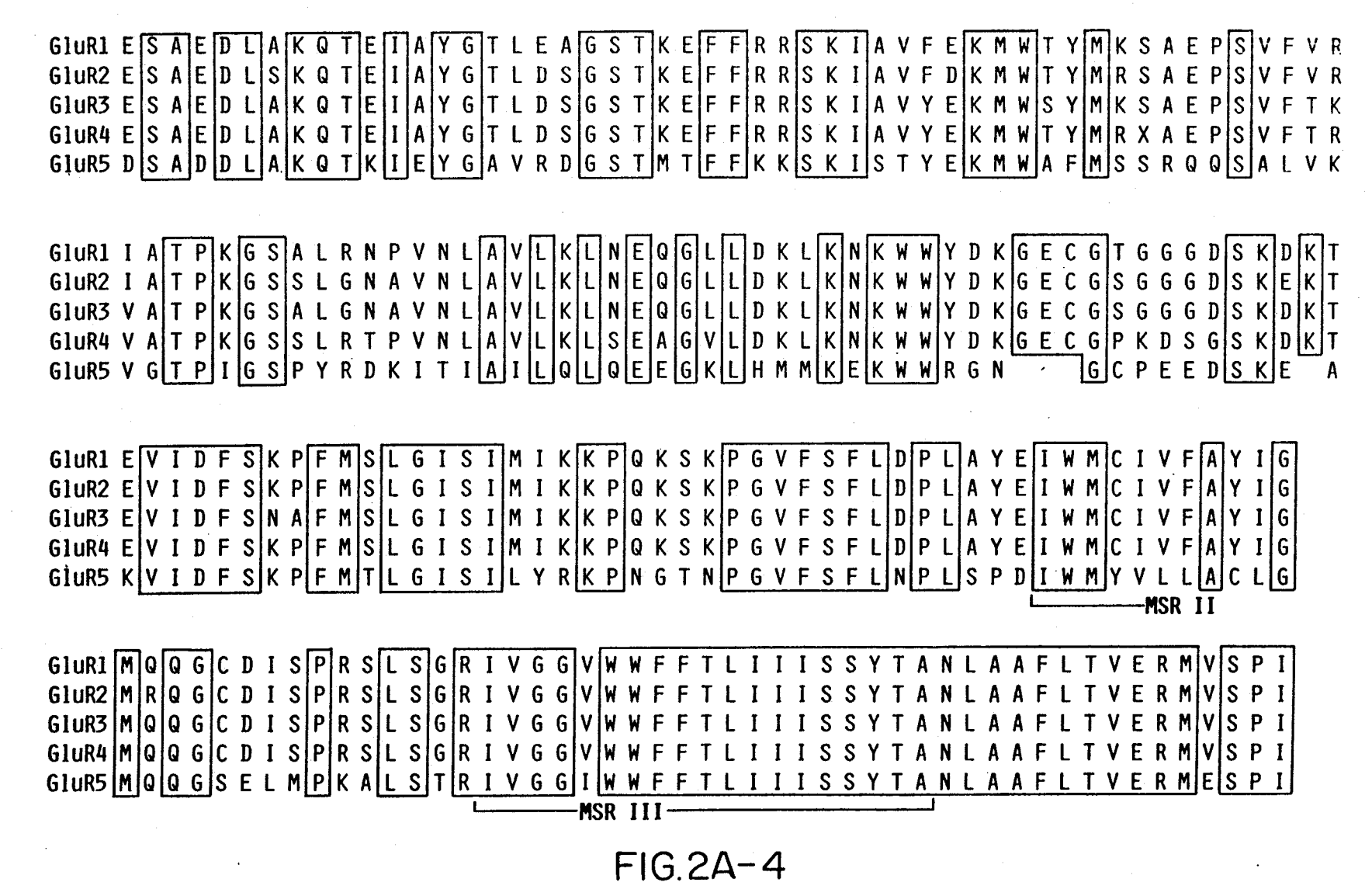

FIG. 2A is an alignment of the deduced amino acid sequences for the proteins encoded by the GluR1, GluR2, GluR3, GluR4 and GluR5 genes. In the figure, identical residues in all compared sequences are boxed, with spaces introduced as appropriate to maximize homology. Predicted signal peptides and four proposed membrane spanning regions (MSR I-IV) are indicated. The hatched line denotes the insertion of 15 amino acid residues found in the GluR5-1, but not in the GluR5-2 protein. As the aligned sequences demonstrate, there is significant sequence identity between GluR1 and both GluR2 (70%) and GluR3 (69%) as well as between GluR2 and GluR3 (74%; see also Table 1). The sequence identity is most pronounced in the carboxy-terminal half of each protein.

FIG. 2B is a comparison of the deduced amino acid sequences for the signal peptides encoded by the GluR1, GluR2, GluR3, GluR4, GluR5, GluR6 and GluR7 genes.

EXAMPLE IX

Electrophysiological Comparison: GluR1, GluR2 and GluR3

Based on the strong sequence similarity between the proteins encoded by GluR1, GluR2 and GluR3, the following experiments were conducted to determine if the GluR2 and GluR3 proteins might function as homomeric, kainate-sensitive ion channels in Xenopus oocytes (as is the case with GluR1). Thus, oocytes were injected with in vitro synthesized RNA transcripts derived from individual cDNA clones. FIG. 3 presents a comparison of current responses measured in Xenopus oocytes injected with individual GluR1, GluR2 and GluR3 subunit RNAs or rat brain hippocampus poly(A)+ RNA. FIG. 3A shows responses of oocytes to 100 mM KA measured 3 days after injection of individual GluR1 (2 ng), GluR2 (10 ng) or GluR3 (2 ng) RNA. The insert shows examples of voltage recording traces obtained from such oocytes except that the GluR2 response was obtained 5 days after injection of 25 ng RNA. The figure further shows that both GluR2 and GluR3 injected oocytes depolarize in response to batch application of 100 μM KA.

The amplitudes of the KA responses were not equivalent for the three glutamate receptor subunits: with equal amounts of injected RNA (2 ng), responses in GluR3 RNA-injected oocytes were invariably larger than GluR1 responses. KA-invoked depolarizations in GluR2-injected oocytes were the weakest and could only be detected in oocytes injected with much larger amounts of RNA (10 to 25 ng).

The data in FIG. 3B represent the responses of oocytes to the indicated agonists measured 3 days after injection with GluR1 (2 ng) or GluR3 (2 ng) RNA or adult rat brain hippocampus poly(A)+ RNA (~50 ng). All values are normalized to the response obtained with 100 mM KA and are presented as the mean ±S.E.M. with n≧3 for all measurements. All oocytes were voltage-clamped to −70 mV and recordings were performed as described by Hollmann et al., Nature 342:643 (1989). The data show that, in addition to KA, oocytes injected with GluR1 or GluR3 RNA also respond to QUIS (10 μM), AMPA (50 μM), and glutamate (GLU, 100 μM). No detectable responses were obtained with NMDA (30 μM plus 10 μM glycine) or APB (50 μM). Responses obtained from oocytes injected with GluR2 RNA were too small for reproducible quantitation and were, therefore, excluded from the analysis. For GluR1-injected oocytes, the responses to AMPA and QUIS were typically 35-40% of the maximal KA response, while for GluR3-injected oocytes they were about 10% of the KA response. Relative to KA, the response of GluR1 to domoic acid (DOM, 10 μM) is about 6-fold greater than that seen for GluR3. Taken together these data demonstrate that receptors assembled from GluR1 or GluR3 subunits are pharmacologically distinct. Furthermore, the observation that homomeric GluR1 and GluR3 receptors respond to both QUIS and AMPA, albeit with reduced efficiencies, provides direct evidence that KA, QUIS and AMPA can bind to the same glutamate receptor polypeptide.

FIG. 3B also shows that the pharmacological profile of oocytes injected with individual GluR1 or GluR3 subunit RNA is significantly different than that seen in oocytes injected with rat brain hippocampus poly(A)+ RNA. This suggests that the response seen in oocytes injected with hippocampus RNA is mediated by heteromeric glutamate receptors assembled from various combinations of GluR1, GluR2 and GluR3 subunit polypeptides. This suggestion is supported by the fact that all three GluR subunit genes are actively transcribed in the hippocampus.

EXAMPLE X

Pharmacological Comparison of GluR1, GluR2 and GluR3

This example addresses the question of whether glutamate receptors assembled from mixtures of proteins encoded by the GluR1, GluR2 and GluR3 subunit genes have pharmacological properties significantly different from each other or from those observed for single subunit receptors. FIG. 4 presents a comparison of current responses measured in Xenopus oocytes injected with combinations of GluR1, GluR2 and GluR3 RNAs.

Figure 4B:
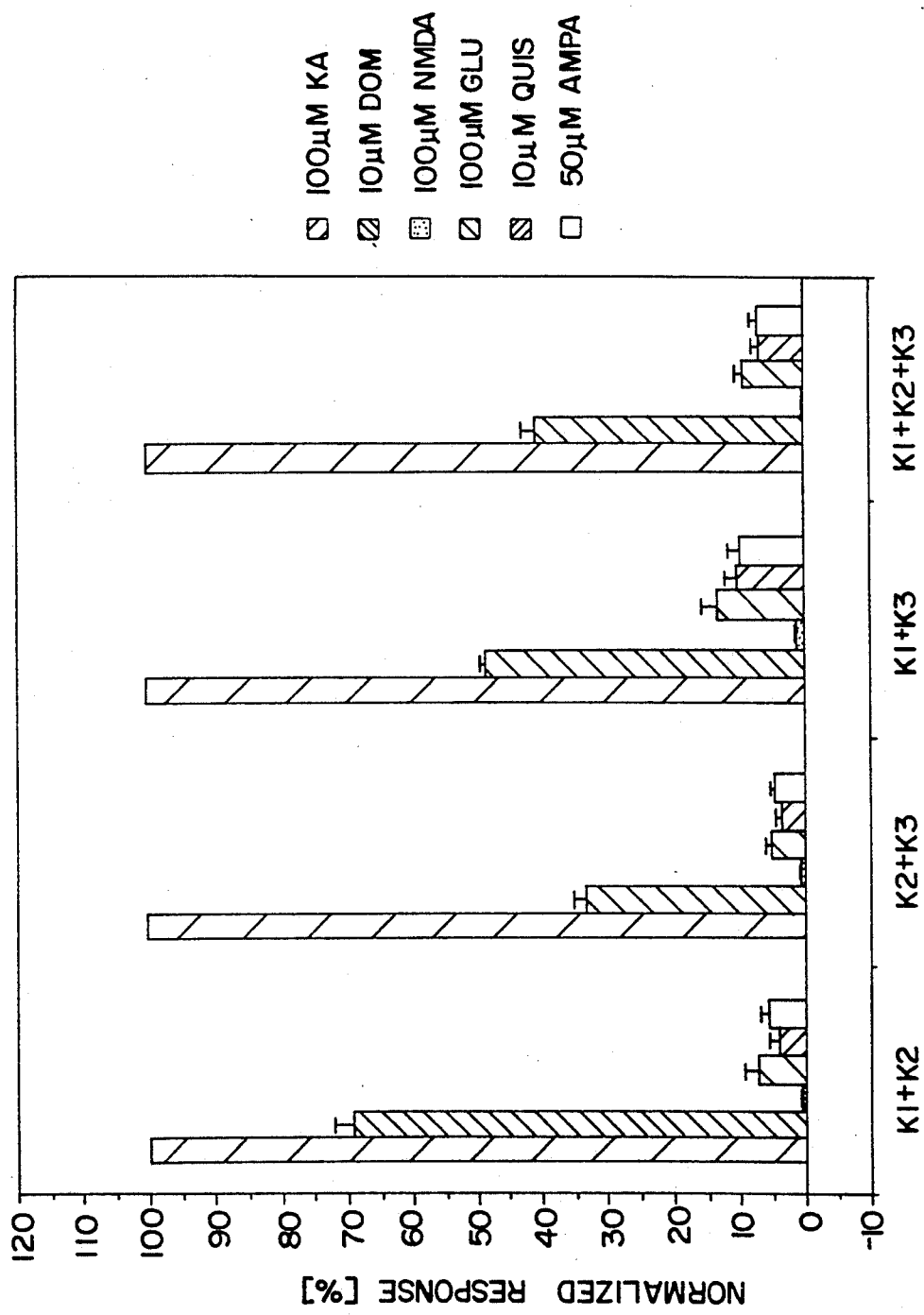
FIG. 4 (A and B) is comprised of two graphs which compare current responses measured in Xenopus oocytes injected with combinations of GluR1, GluR2 and GluR3 RNAs.

A comparison of the data in FIG. 3B and 4B suggests that, for the agonists tested, there are few substantial differences in the pharmacology. FIG. 4B summarizes the responses of oocytes to the indicated agonists measured 3 days after injection of 2 ng RNA for each of the indicated GluR subunits or 50 ng rat brain hippocampus poly(A)+ RNA. Values have been normalized to the response obtained with 100 mM KA and are presented as the mean ±S.E.M. with n≧3 for all measurements. All oocytes were clamped to −70 mV and recordings performed as described by Hollmann et al. [Nature 341:643 (1989)]. Responses to QUIS, AMPA and GLU are, relative to GluR1, significantly reduced in the oocytes expressing the subunit combinations. Except for the NMDA response, the overall agonist profiles for oocytes injected with GluR subunit combinations are more similar to oocytes containing hippocampus poly(A)+ RNA than to those injected with either GluR1 or GluR3 subunit RNA alone.

EXAMPLE XI

Comparison of KA-Activated Currents Recorded from GluR1, GluR2 and GluR3

FIG. 4A presents the responses of oocytes to 100 mM KA measured 3 days after injection of 2 ng RNA for each of the indicated GluR subunit combinations. The open columns represent the sum of the responses measured in oocytes expressing the individual GluR subunit RNAs, while the stippled columns show the measured amplitudes after expression of combinations of the GluR subunit RNAs in individual oocytes. The figure compares KA-activated currents recorded from oocytes injected with mixtures of GluR1, GluR2 and GluR3 subunit (stippled columns) with the summed currents measured for the individual subunits (blank columns).

The principle finding is a significant potentiation of KA-evoked currents in oocytes coexpressing glutamate receptor subunits. For example, co-expression of GluR1 plus GluR2 yields an approximately 4-fold increase over the summed responses for singly-injected oocytes; or co-expression of GluR2 plus GluR3 subunits yields an approximately 2-fold increase. Injection of all three subunit RNAs results in an average 2.5 fold-increase in KA-evoked currents.

These results indicate that, in oocytes, individual glutamate receptor subunit polypeptides do not behave in a simple independent fashion. Instead, the various subunits apparently interact with each other, by the generation of heteromeric glutamate receptors with properties which are distinct from the receptors comprised of solitary glutamate receptor subunits.

EXAMPLE XII

Current-Voltage Relationships for KA-Evoked Responses

This example examines the current-voltage (I/V) relationships for KA-evoked responses measured in oocytes injected with individual GluR subunits, combinations thereof, or hippocampus poly(A)+ RNA.

Figure 5A:
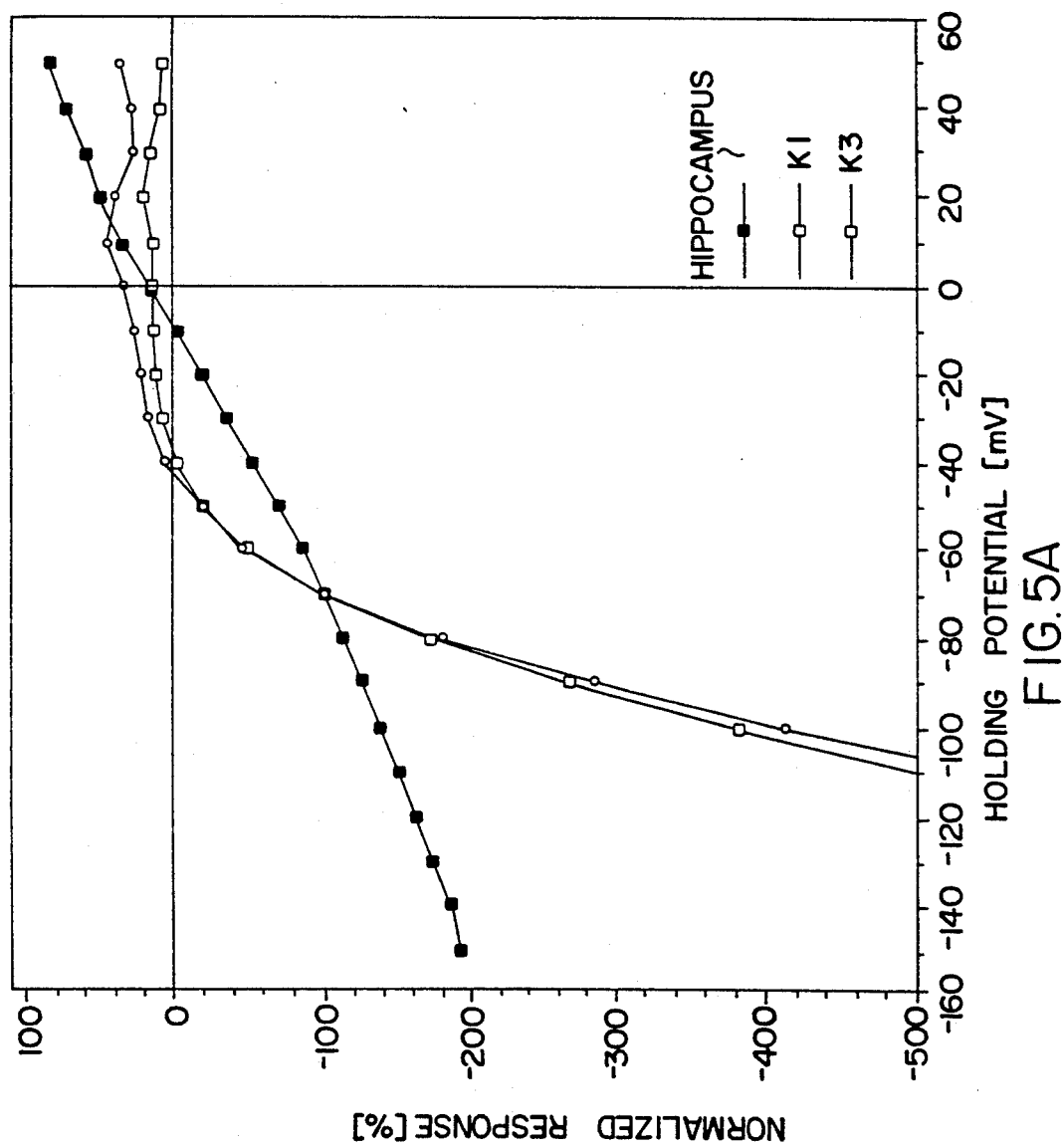
FIGS. 5 a to c are three graphs which illustrate the dependence of the current responses to 100 mM KA upon the membrane potential.

The I/V data are illustrated in FIG. 5 where the dependence of current response to exposure to 100 mM KA upon the membrane potential is shown. Data obtained from oocytes injected with individual glutamate receptor subunit RNAs are shown in panel A, data obtained from oocytes injected with combinations of subunits are shown in panels B and C, and for purposes of comparison, data obtained from oocytes expressing hippocampus poly(A)+ RNA are also shown in panel A, where data obtained from oocytes injected with rat brain hippocampus poly(A)+ RNA (50 ng) are indicated by a Solid Square ■, oocytes injected with GluR1 RNA are indicated by an Open Square (□) or oocytes injected with GluR3 RNA are indicated by an Open Circle (O); (B) oocytes injected with GluR1 plus GluR2 RNAs are indicated by a Solid Square ■ or oocytes injected with GluR1 plus GluR3 RNAs are indicated by an Open Square (□); and (C) oocytes injected with GluR2 plus GluR3 RNAs are indicated by a Solid Square ■ or oocytes injected with all three GluR subunit RNAs are indicated by an Open Square (□). Recordings were made from oocytes 3 days after injection of 2 ng RNA for each GluR subunit. Voltages were stepped by 10 mV between −150 mV and +50 mV; all values are normalized to the response measured at −70 mV.

The KA responses measured in oocytes injected with brain poly(A)+ RNA show an approximately linear I/V relationship with a reversal potential of about −10 mV. This result is in marked contrast to the I/V curves obtained for oocytes injected with single GluR1 or GluR3 subunit RNA. The GluR1 and GluR3 I/V curves show strong inward rectification and reversal potentials near −40 mV. From these data it is clear that the KA-sensitive receptors present in oocytes injected with hippocampus RNA are different from those assembled by oocytes injected with GluR1 or GluR3 subunit RNAs.

Figure 5B:
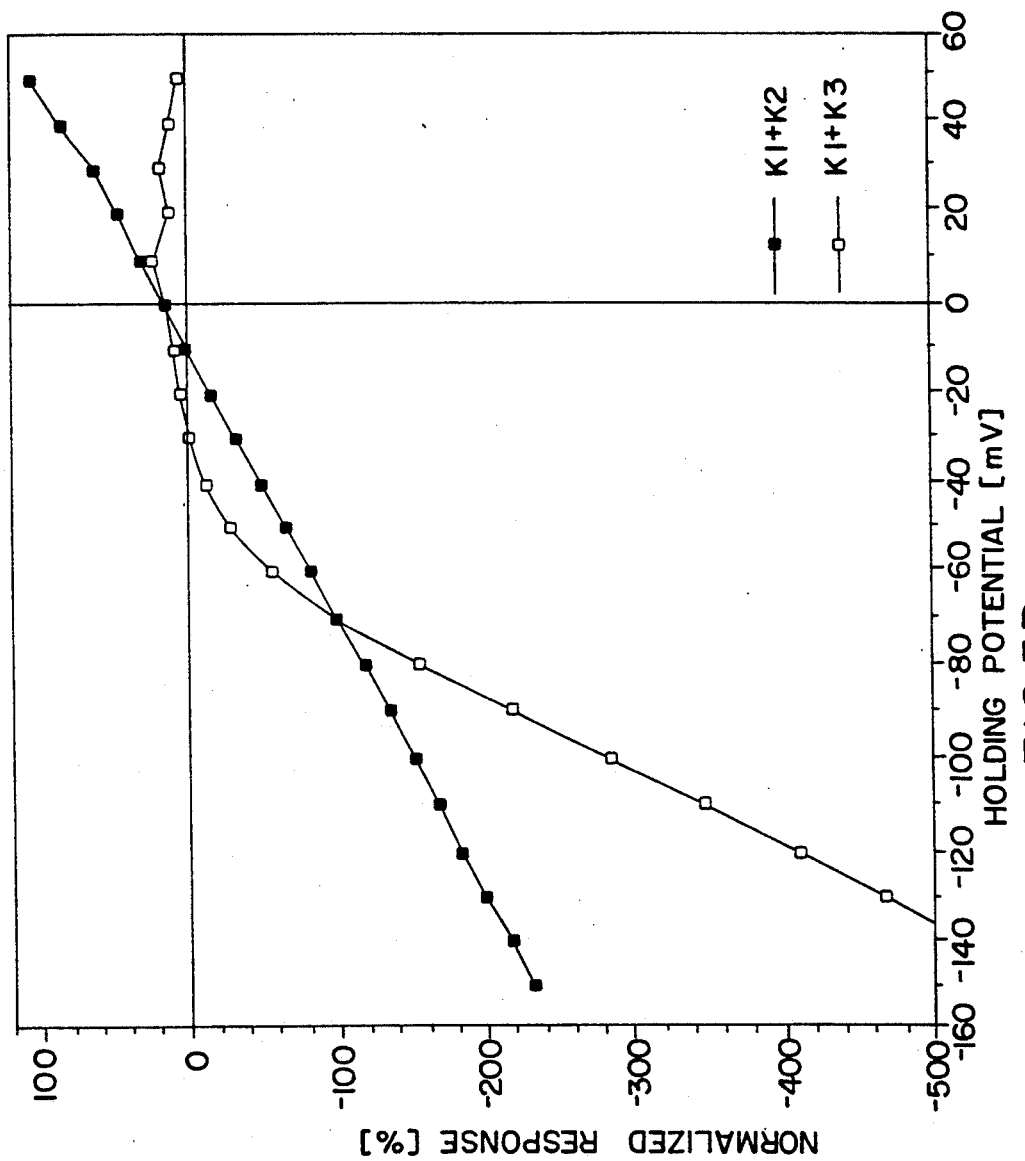

In FIG. 5B the I/V curve for the GluR1 plus GluR2 combination is noticeably different from that observed for the GluR1 subunit alone. Oocytes injected with this pair of RNAs show a nearly linear I/V plot and have a reversal potential of approximately −10 mV. This plot is strikingly similar to that seen with hippocampus RNA-injected oocytes (panel A). In contrast, the I/V curve for the GluR1 plus GluR3 combination is only marginally different from those measured in oocytes expressing the individual subunits.

Figure 5C:
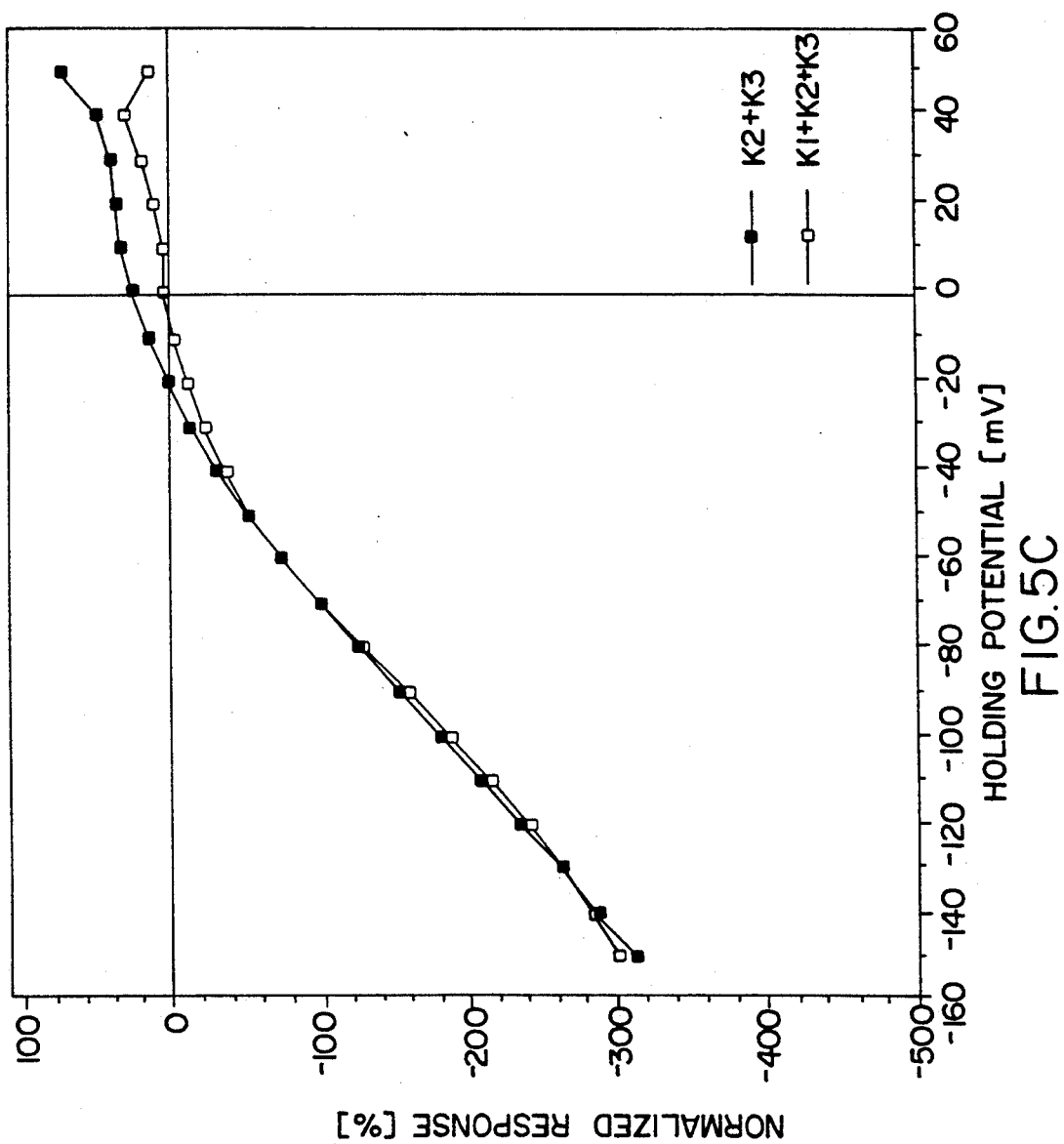

FIG. 5C shows some inward rectification in the I/V curve for the GluR2 plus GluR3 subunit combination, as well as a reversal potential somewhat more negative (−20 mV) than those determined for GluR1 plus GluR2 or hippocampus RNA I/V plots (−10 mV). When all three glutamate receptor subunit RNAs are combined in a single oocyte, the resulting I/V curve approximates that seen for the GluR1 plus GluR2 combination in both reversal potential and slope; however, the responses with the three subunits show a pronounced inward rectification not observed with GluR1 plus GluR2.

EXAMPLE XIII

Distribution of GluR1, GluR2 and GluR3 mRNA in the Mammalian Central Nervous System The distribution of GluR1, GluR2 and GluR3 RNAs in the adult rat brain was examined to test the hypothesis that proteins encoded by the GluR1, GluR2 and GluR3 genes assemble to form heteromeric glutamate receptors in vivo. This hypothesis would be rendered highly unlikely by a showing that the individual subunit genes are transcribed in different neuroanatomical loci. The distribution of the variou subunit RNAs was examined using radiolabeled anti-sense RNA probes and in situ hybridization histochemistry essentially as described by Deneris et al. [J. Biol. Chem. 264:6268 (1989)]. The hybridization patterns obtained with the GluR1, GluR2 and GluR3 probes were nearly identical, with the strongest hybridization seen in the CA1-CA3 regions of the hippocampus and the dentate gyrus. High-resolution analysis of these areas suggests that the hybridization signal originates in the pyramidal cell layer of regions CA1-CA3 and the granule cell layer of the dentate gyrus. Somewhat weaker hybridization of all three probes was seen in the piriform cortex, caudate-putamen, amygdala, and hypothalamus. Low levels of hybridization were detected in the thalamus, with little or no signal observed in fiber tracts. While differential hybridization was seen in the medial habenula and neocortex, the overall patterns of expression for the GluR1, GluR2 and GluR3 subunit genes showed substantial concordance.

EXAMPLE XIV

Isolation of cDNAs for GluR4 and GluR5

GluR4

Using a fragment of the GluR2 cDNA (nucleotides 1793-2240) as a probe in a low stringency hybridization protocol (as per Example II), several GluR4 and GluR5 clones were isolated from a rat forebrain library (as described in Example VIII). Sequence analysis demonstrated that none of the cDNA clones contained an entire open reading frame. Northern blots with mRNA from different adult rat brain tissues indicated that the GluR4 and GluR5 transcripts were most abundant in the cerebellum. Consequently, the partial GluR4 and GluR5 cDNA clones were used as probes under high stringency screening conditions to isolate cDNAs encoding large open reading frames from an adult rat cerebellum cDNA library constructed in the vector λZAP.

Of the cDNA clones thus isolated, two GluR4-related clones (λCER112 and λCER121B) encoded only portions of the GluR4 gene but possessed sufficient overlap to engineer a full-length, expressible construct in the pBS SK (+) vector (Stratagene Cloning Systems, La Jolla, Calif.). The nucleotide sequence of this GluR4 construct, designated pK45, was determined and is presented in Sequence ID No. 7, along with the deduced amino acid sequence therefor.

The GluR4 mRNA was detected on Northern blots of cerebellum RNA as a 4.6 kb species. The smaller size mRNA may represent splice variants.

GluR5

Among the 29 GluR5-related cDNAs isolated from the cerebellum library, three clones, specified λRB12, λRB15 and λRB20, were identified which encode an identical large open reading frame. The sequence of cDNA clone λRB20 (GluR5-1) is shown in Sequence ID No. 9. Cleavage of the assumed signal peptide is predicted to occur between amino acid positions 30 and 31 [von Heijne, Nucl. Acids Res 14:4683 (1986)]. This cleavage site is after a proline residue, which is atypical. The signal peptide is encoded by a fragment of about 30 amino acids. Potential sites of N-linked glycosylation are found at Asn-68, Asn-74, Asn-276, Asn-379, Asn-428, Asn-439, Asn-620 and Asn-766.

λRB15 and λRB12 are shorter than λRB20 at the 5′ end. The λRB20 cDNA consists of a 5′ untranslated region of 187 bp, a continuous open reading frame of 2760 bp, and a 3′ untranslated region of 303 bp. The 5′ untranslated region ends with the sequence AA-GATGG, which is characteristic of a translational start site.

Three additional cDNA clones originally isolated from the forebrain library were also examined. The sequences of these cDNAs are identical to λRB20 in the predicted translation initiation site region. Sequence analysis revealed that two variants of the GluR5 cDNA are represented in the forebrain and the cerebellum libraries. This heterogeneity derives from the insertion of 45 nucleotides (found in λRB20 and 17 of the 29 GluR5-related cDNA clones isolated). The insertion of 45 nucleotides, as found in λRB20, but not in 12 of the 29 cDNA clones isolated, occurs between nucleotides 1388 and 1434. This insertion does not interrupt the open reading frame. Furthermore, consensus splice donor and acceptor sites are absent [Breathnach and Chambon, Ann. Rev. Biochem. 50:349-383 (1981)], which suggests that the insertion does not arise from an unspliced intron and is, most likely, the result of an alternative splice event. Nucleotide sequence analysis indicates that the two GluR5 variants are otherwise identical.

No cDNA clone was found for the shorter splice variant encoding the entire open reading frame. Therefore a clone (λRBΔ20) was constructed that is missing the 45 nucleotide insertion found in λRB20 (GluR5-1) but is otherwise identical to that clone. The shorter splice variant clone (λRBΔ20) is referred to as GluR5-2. Both λRB20 and λRBΔ20 were used in Xenopus oocyte expression experiments (see Example XVI) and the variant proteins encoded were named GluR5-1 and GluR5-2, respectively.

Northern blot analysis of cerebellum RNA indicated that the major GluR5 mRNA has a size of 6 kilobases.

EXAMPLE XV

Structural Features of GluR5 cDNA and Protein

Translation of the cDNA nucleotide sequence for GluR5-1 predicts a single long open reading frame of 920 amino acid residues (see Sequence ID No. 9). The GluR5 sequence has overall amino acid sequence identity with each of the KA/AMPA subunits (see FIG. 2, and Table 1). The 15 amino acid insertion in GluR5-1 is unique among the proteins listed, thus the shorter GluR5-2 variant is the counterpart to the KA/AMPA subunits characterized. Table 1 shows that GluR5 is thus far the most dissimilar glutamate receptor subunit identified; and the comparison of GluR5 with the KA/AMPA subunits highlights the most conserved sequence elements (FIG. 2). Within other ligand-gated ion channel families (i.e., the neuronal nicotinic acetylcholine receptors (nAChR), the $GABA_A$ receptors and the glycine receptors), the N-terminal extracellular domain is most conserved while the C-terminal sequences diverge between the membrane-spanning regions (MSR) III and IV. In the glutamate receptor subunit gene family, in contrast, the regions N-terminal of the proposed MSR I [Hollmann et al., Nature 342:643 (1989)], have only 17% identity and are less similar than the regions C-terminal of MSR I which have 45% identity. The 'Cys-Cys loop', a signature for ligand-gated neurotransmitter receptor channel complexes [Barnard et al., Trends Neurosci. 10:502 (1987)] is not conserved in the glutamate receptor subunit family (FIG. 2). The C-terminal half of glutamate receptor subunits is thought to be involved in channel formation and contain the membrane spanning regions (MSR I-IV; FIG. 2). The presumed MSR III is the most conserved continuous sequence, with only one conservative amino acid exchange (Val to Ile) in the GluR5 protein (FIG. 2). As mentioned above, in other ligand-gated channel families the segment between MSR III and IV is divergent in length and sequence. In the glutamate receptor subunit family the similarity in this postulated segment is high (48%) and only GluR5 exhibits a sequence length variation. The KA/AMPA receptors and the GluR5 protein are generally divergent C-terminal of the proposed MSR IV.

The hydrophobicity plot for GluR5 is similar to those of the KA/AMPA receptors, suggesting a conserved secondary structure in the proposed ion channel forming portion of the protein. However, the N-terminal half of the GluR5 hydrophobicity plot is unusual. In this region, GluR5, as compared to the KA/AMPA subunits, is more hydrophobic and contains several segments that could span the membrane. Based on algorithms that search for membrane-associated helices, four [Rao and Argos, Biochim. Biophys. Acta 869:197-214 (1986)] or seven [Eisenberg et al., J. Mol. Biol. 179:125-142 (1984)] putative transmembrane regions can be assigned to GluR5.

A comparison of the C-terminal regions of all five glutamate receptor subunits with the frog [Gregor et al., Nature 342:689 (1989)] and chicken [Wada et al., Nature 342:684 (1989)] KA binding proteins demonstrates a similar extent of sequence conservation (35-40% amino acid identity). A FASTA search [Pearson and Lipman, Proc. Natl. Acad. Sci. USA 85:2444 (1988)] of the GenBank, EMBL and SWISS-PROT databases with the GluR5 sequence uncovered no significant similarities to other proteins.

EXAMPLE XVI

Electrophysiological Properties of GluR5 mRNA Injected Oocytes Exposed to L-Glutamate In vitro synthesized GluR5-1 and GluR5-2 cRNAs were individually expressed in Xenopus oocytes. With either cRNA, the glutamate receptor agonists KA (100 MM), AMPA (50 μM), quisqualate (10 μM), APB (100 μM) and NMDA (100 μM, applied with 10 μM glycine) did not elicit membrane depolarizations in cRNA injected oocytes. However, weak membrane depolarizations induced by L-glutamate (100 μM) were recorded in oocytes injected with GluR5-1 cRNA (maximal depolarization 3.5 mV) and GluR5-2 cRNA (maximal depolarization 4.5 mV). Significantly stronger membrane depolarizations were not found in response to L-glutamate in oocytes co-injected with GluR5-1 and GluR5-2 cRNA as compared to oocytes injected with GluR5-2 cRNA alone. For any particular oocyte injected with GluR5-1 or GluR5-2 cRNA, the depolarizations were reproducible, showed fast onset, and were slowly (within 5 minutes) reversed when agonist superfusion was switched to buffer superfusion. Neither uninjected oocytes nor water-injected oocytes showed a response to the glutamate receptor agonists tested. Responses to L-glutamate were recorded in 7 (out of 7) oocytes for GluR5-1 (membrane depolarization 2.29±0.26 mV S.E.M.) and 29 (out of 33) oocytes for GluR5-2 (2.27±0.19 mV S.E.M).

EXAMPLE XVII

Distribution of GluR4 and GluR5 mRNA In the Developing Central and Peripheral Nervous Systems For the developmental study of GluR4 and GluR5 gene expression, sections of mice from embryonic day 10 (E10) through post natal day 21 (P21) were analyzed using in situ hybridization and histochemistry.

In the entire central nervous system (CNS), a diffuse expression of the GluR4 and GluR5 genes was detected at E10. These first hybridization signals originate from postmitotic neurons. This is best demonstrated in the myelencephalon at E12. The ependymal layer is facing the neural canal and contains dividing neuroblasts. No hybridization was detectable in these cells. The postmitotic cells are located in the exterior part of the neural tube and express both genes.

Later in development, transcripts for GluR5 and, to a lesser extent, GluR4 were particularly pronounced in areas where neurons differentiate and assemble into nuclei. These temporal changes in the hybridization pattern were best observed for GluR5 (in the primary sensory nuclei of the medulla oblongata and the nuclei of the pons which hybridized more intensely than surrounding structures at E14). GluR5 gene expression was particularly intense in several discrete brain nuclei, whereas GluR4 gene expression was detectable over the entire rostral and caudal parts of the brain.

During postnatal development, the spatial distribution of GluR4 gene transcripts did not change but usually smaller amounts of mRNA were detectable than at late embryonic stages. In contrast, GluR5 gene expression appeared to become more restricted spatially during development, and transcript levels were downregulated. Extreme changes in the temporal GluR5 hybridization pattern were apparent in the cerebellar cortex. Until P12, high GluR5 transcript levels were detected in the granular and Purkinje cell layer. Later, the intensity of hybridization signals in the granular cell layer was reduced relative to the Purkinje cell layer and starting at P14, only a faint hybridization signal was detected in the granular cell layer.

In general, those regions of the brain that exhibited a dense labeling during embryonic development also had detectable transcript levels in adults. In P21 animals, the highest GluR4 transcript levels were observed in the cell layers of the olfactory bulb, the hippocampus, the cerebellum and the retina. In the retina, strong hybridization was found in the ganglion cell layer and in the amacrine cells of the inner nuclear layer. No expression was detected in Muller cells. For GluR5, the strongest hybridization signals at P21 were found in the olfactory bulb, the amygdala, the colliculi and some hypothalamic nuclei.

In the developing peripheral nervous system (PNS), the hybridization assays showed that the GluR4 and GluR5 genes are expressed to varying degrees in the cranial ganglia (e.g., trigeminal ganglion, acoustic ganglia), dorsal root ganglia and the mural ganglia of the intestinal organs. Comparable to the CNS, transcripts in the PNS are detected by E10 for GluR4 and by E11 for GluR5. During development, hybridization signals for GluR4 continuously increase until early postnatal stages and then persist with similar intensity in adults. Hybridization signals for GluR5 increase up to E16 and remain with comparable intensity in later developmental stages. In postnatal animals, the dorsal root ganglia (GluR5) and the mural Ganglia of the intestinal organs (GluR4 and GluR5) exhibit higher levels of hybridization than the CNS. High resolution autoradiography in the dorsal root ganglia demonstrates hybridization of the GluR5 probe over neuronal cells whereas satellite cells are unlabeled.

EXAMPLE XVIII

Distribution of GluR4 and GluR5 mRNA in the Adult Mammalian (Rat) Brain

The distribution of the GluR4 and GluR5 mRNA transcripts in the adult CNS was studied by in situ hybridization. In the forebrain region, high levels of GluR4 transcripts were detected in the CA1 and the dentate gyrus of the hippocampus, in the medial habenula and particularly in the reticular thalamic nucleus. The hippocampus showed only weak expression of the GluR5 gene and no transcripts were detected in the medial habenula. The GluR5 hybridization signal was intense in the cingulate and piriform cortex, several hypothalamic nuclei, the amygdala and the lateral septum. In the cerebellum, the hybridization patterns for GluR4 and GluR5 probes were overlapping but distinct. Both probes were detected at high levels in the Purkinje cell layer. In the granular cell layer the GluR4 probe produced strong labeling, while GluR5 probe labeling was weak.

EXAMPLE XIX

Isolation of GluR6 and GluR7 cDNA clones encoding the GluR6 and GluR7 genes were isolated from an adult rat forebrain library using a low-stringency hybridization screening protocol (see Example II) and a radiolabeled fragment of about 1.2 kbp (nucleotides 705-2048) of the GluR5 cDNA as a probe. The selected clones were identified by restriction digest map and sequencing.

An adult rat cerebellum cDNA library constructed in λZAP was screened under low-stringency hybridization conditions with the above-described GluR5 cDNA fragment [Bettler et al., Neuron 5: 583-595 (1990)]. A 3 kb fragment from a cDNA clone encoding part of the GluR6 open reading frame was used to rescreen the library under high-stringency hybridization conditions. Two clones, RC11 and RC27, possessed sufficient overlap to engineer a cDNA clone encoding the entire open reading frame of the GluR6 protein.

A 4559 base pair cDNA encoding a protein of 884 amino acid residues was engineered from RC11 and RC27. The protein encoded by this cDNA is referred to as GluR6. Sequence ID No. 11 shows the nucleotide and deduced amino acid sequence of the GluR6 clone. The similarity between the hydropathy profile of the GluR6 subunit and those of the GluR1-GluR5 subunits suggests a similar membrane spanning topology.

Another adult rat cerebellum cDNA library was constructed in λZAP and screened under low-stringency hybridization conditions with the above-described GluR5 cDNA fragment. A 2 kb fragment from a cDNA clone encoding part of the GluR7 open reading frame was used to rescreen the library under high-stringency hybridization conditions. Two clones, RP52 and RPC44, possessed sufficient overlap to engineer a cDNA clone encoding the entire open reading frame of the mature GluR7 protein.

A 3344 base pair cDNA encoding a protein of 921 amino acid residues was engineered from RP52 and RPC44. The protein encoded by this cDNA is referred to as GluR7. Sequence ID No. 13 shows the nucleotide and deduced amino acid sequence for the GluR7 clone.

The physiological and pharmacological properties of the homomeric GluR6 ion channel were studied in Xenopus oocytes injected with in vitro transcribed RNA. In oocytes held at −100 mV, application of kainate and glutamate evoked inward currents that desensitized in continued presence of agonist. Full recovery from desensitization caused by application of 100 $\mu$M kainate for 30 seconds required approximately 15 minutes. Quisqualate activated only small inward currents; however, quisqualate application attenuated a subsequent kainate evoked current. AMPA (100 $\mu$M) did not evoke any detectable current, nor did it antagonize a kainate-evoked current when AMPA and kainate were applied together. The AMPA solution used in the experiment did evoke responses in oocytes injected with either hippocampal mRNA or GluR1 RNA (which are both known to respond to AMPA).

Exposure of the injected oocyte to 10 μM concanavalin A (Con A) for 5 minutes efficiently decreases desensitization [see Meyer & Vyklicky, Proc. Natl. Acad. Sci. USA 86: 1411-1415 (1989)] and allows agonist-activated currents mediated by the GluR6 receptor to be more easily studied. Con A treatment increased current elicited by kainate and glutamate by 75 to 150-fold compared to the peak current for equimolar concentrations before the treatment. After Con A treatment, the maximal current induced by glutamate (relative to kainate) was 0.56±0.03 and for quisqualate 0.38±0.03. Con A treated oocytes injected with GluR6 RNA responded to kainate, but did not respond to application of 100 μM aspartate, 100 μM NMDA in the presence of 3 μM glycine, or 10-1000 μM AMPA. Furthermore, coapplication of AMPA (100 μM) had no effect on the kainate-evoked (1 μM) responses on Con A treated oocytes. It thus appears that AMPA acts as an agonist on only a subset of the kainate/quisqualate sensitive ionotropic receptors.

Figure 7A:
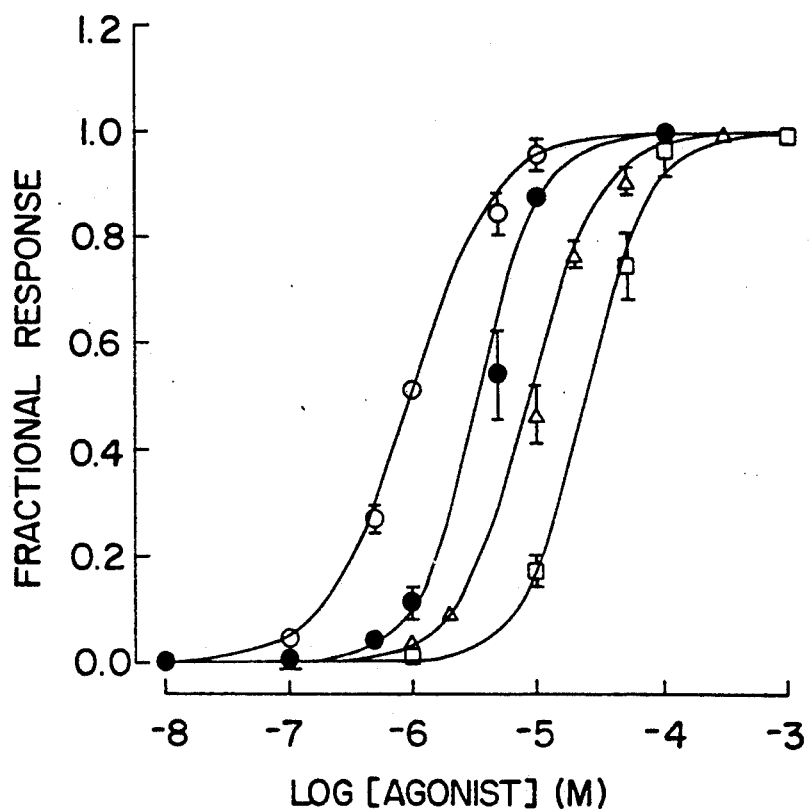
FIG. 7a presents dose response curves obtained on GluR6 injected oocytes.

The dose response curves for activation of the GluR6 receptor were obtained after Con A treatment. Data are summarized in Table 3, and in FIG. 7a, which presents dose-response curves obtained on GluR6 injected oocytes after Con A treatment for kainate (O), glutamate (□), quisqualate (Δ) and kainate in the presence of 10 μM 6-nitro-7-cyano-quinoxaline-2,3-dione (CNQX) ●. All points represent an average of 3-6 independent measurements. Error bars indicate S.E.M.

TABLE 3

$EC_{50}$ and the Maximal Agonist-evoked Current Relative to the Maximal Kainate-evoked Current for Homomeric GluR6 Receptor After Con A Treatment

| Agonist | $EC_{50}$ (μM) | Relative maximal current (± S.E.M. |
|---|---|---|
| Kainate | 1.0 (0.8-1.3) | 1.00 |
| Quisqualate | 11 (10-13) | 0.38 ± .03 |
| Glutamate | 31 (29-34) | 0.56 ± .03 |

The mean of $EC_{50}$ are based on measurements of 3-6 oocytes. The numbers in parentheses indicate 95% confidence intervals. Relative maximum current = maximum agonist-evoked current/maximum kainate-evoked current.

The $EC_{50}$ for kainate (1 μM) is about 35-fold lower than the $EC_{50}$ observed for the homomeric GluR1 ($EC_{50}=35$ μM) receptor [see Hollmann et al., Nature 242: 643-648 (1989); Dawson et al., Mol. Pharmacol. 38: 779-784 (1990)]. The $EC_{50}$ for the GluR6 receptor is 75-fold higher for quisqualate and 10-fold higher for glutamate when compared to the same agonist on the GluR1 receptor. Thus the order of agonist potency for the homomeric GluR6 receptor is:

kainate>quisqualate>L-glutamate.

The order of agonist potency set forth above is similar to the order of binding affinities measured for quisqualate and glutamate as competitive displacers of kainate on kainate binding sites in isolated brain membranes [see Foster and Fagg, Brain Res. Rev. 7: 103-164 (1984)]. This property is clearly distinct from the GluR1 and GluR3 receptors where the relative apparent affinities are:

quisqualate>AMPA>glutamate>kainate.

[See Nakanishi et al., Neuron 5: 569-581 (1990); Boulter et al., Science 249: 1033-1037 (1990); and Foster and Fagg, supra].Therefore, based on agonist potencies ($EC_{50}$), GluR6 can be considered a kainate receptor within the glutamate receptor family.

CNQX acts as a competitive antagonist of non-NMDA receptors in rat brain neurons [see Verdoorn et al., Mol. Pharmacol. 35: 360-368 (1989)]. CNQX blocked both quisqualate and kainate-evoked responses in oocytes injected with GluR6 RNA. The inhibitory effect of 10 μM CNQX was eliminated at high kainate concentrations, consistent with its competitive mode of action. 10 μM CNQX resulted in a 3.5-fold parallel shift of the kainate dose-response curve compared to the curve obtained in absence of CNQX (see FIG. 7a). Considering the competitive action of CNQX at 10 μM, the $K_i$ for CNQX was calculated to be 4 μM. Thus, CNQX is a less potent blocker of kainate responses at GluR6 receptors than at GluR1 receptors ($K_i=0.519$ μM) [see Dawson et al, supra] and kainate receptors derived from forebrain mRNA ($K_i=0.295$ μM) [see Verdoorn et al., supra] expressed in oocytes.

Figure 7B:
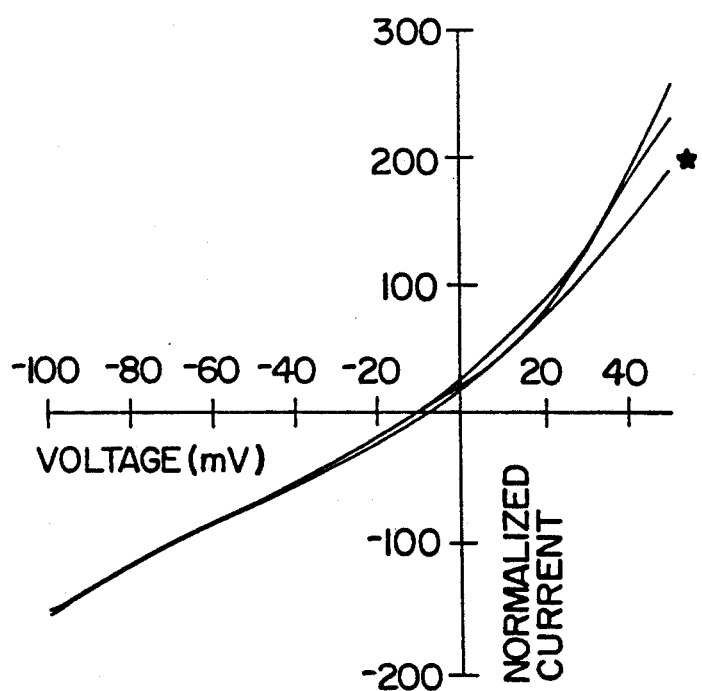
FIG. 7b presents the current-voltage relationship of the homomeric GluR6 receptor evoked by 10 μM kainate before and after Con A treatment. The asterisk indicates the I/V relationship obtained on Con A treated oocytes in a modified frog Ringer solution in which the NaCl was substituted with an equimolar concentration of sodium methanesulfonate. The currents were normalized to the individual currents measured at −70 mV (30 nA and 2.3 μa in Ringer solution before and after Con A treatment, respectively, and 330 nA in the modified Ringer solution).

The current-voltage relationship (I/V) for kainate and glutamate-evoked responses in the presence of Con A and for kainate in the absence of Con A was examined. No qualitative differences were found between Con A-treated and untreated oocytes (see FIG. 7b). The I/V relationships were assessed from 2 s voltage ramps from −100 mV to 50 mV in the presence and absence of agonist. Data were collected and analyzed using the pClamp program set. The I/V relationship exhibited a reversal potential of −10±3 mV and an outward rectification. To analyze whether the outward rectification was an intrinsic property of the channel (or perhaps an activation of endogenous chloride channels activated by a $Ca^{++}$ flux [see Miledi & Parker, J. Physiol. 357: 173-183 (1984)] through the GluR6 ion channel), the kainate-evoked I/V relationship was recorded in a buffer where 95% of the $Cl^-$ ions were substituted by an equimolar amount of methanesulfonate (which is known to shift the chloride reversal potential in a positive direction [see Verdoorn & Dingledine, Mol. Pharmacol. 34: 298-307 (1988)]). No significant change in the reversal potential was observed. Thus, if there is a $Ca^{++}$ flux in Ringer solution, it is not sufficient to activate a $Cl^-$ current. The substitution of $Cl^-$ with methanesulfonate reduced the current 8-fold; this may have been caused by either inhibition of agonist binding or a direct methanesulfonate block of the channel. The latter effect might be potentiated at positive holding potentials.

The expression pattern of the GluR6 gene was studied by in situ hybridization using brain sections from adult mice. The highest levels of GluR6 transcripts were observed in the olfactory lobe, piriform cortex, dentate gyrus, hippocampus, and in the granular cell layer of the cerebellum. In the hippocampus a gradient in hybridization intensities was observed from rostral to caudal areas, with increased intensity in the CA3 region as compared to the CA1 region. The high level of transcripts in the pyramidal cell layer of CA3 and the granule cell layer of the dentate gyrus correlates with the previously observed high level of [³H]kainate binding in the stratum lucidum and the commissural/associational terminal field of the dentate gyrus, respectively [see Foster and Fagg, supra: and Monaghan & Cotman, Brain Res. 252: 91-100 (1982)]. Less intense hybridization signals were observed in the caudate putamen, the zona incerta of the thalamus, the inner and outer layers of cortex, several brain stem nuclei as well as the ganglion cell layer of the retina. In general, areas expressing high level of transcripts correlate well with areas expressing high affinity kainate binding sites.

The properties observed herein for the homomeric GluR6 receptors have not been described in studies performed on neurons. The pattern of the gene expression and the pharmacology of the GluR6 subunit suggest that this subunit might correspond or contribute to the receptor with high affinity for kainate found in the brain.

EXAMPLE XX

GluR-Related Assays

The GluR cDNAs, mRNAs, proteins and functional fragments thereof, are useful in various assays designed to identify and characterize L-glutamate receptors, agonists and antagonists. For example, the cDNAs are useful as probes to identify additional members of the glutamate receptor gene family. mRNAs transcribed from the DNAs of the invention are especially useful in assays designed to identify and characterize both functional receptors and ligands. This use is especially important for the identification and design of compounds that can affect L-glutamate receptor function.

In an assay for identifying and characterizing functional receptors, mRNA is transcribed from DNAs of the invention (either full length or fragments thereof produced by deletions, substitutions, synthesis, etc.) and then translated to produce GluR proteins. In a presently preferred means for carrying out this transcription and translation, the mRNAs are translated in oocytes, preferably Xenopus oocytes. Alternatively, suitable cultured mammalian cells can be used as hosts for the production of glutamate receptor proteins. Such mammalian cells can be transfected in vitro with DNAs of the invention to yield either stable or transiently transfected cell lines. The expressed glutamate receptor proteins are then exposed to ligands known to functionally bind to and activate glutamate receptors. The physiological characteristics of the glutamate receptor proteins are measured by suitable means (e.g., by electrophysiology), and those that form functional ion channels are concluded to be functional glutamate receptor.

In a related assay designed to identify functional ligands for glutamate receptors, proteins known to functionally bind to glutamate receptor agonist or antagonist compound(s) are contacted with at least one "unknown" or test compound whose ability to effect the ion channel activity of glutamate receptors is sought to be determined (in the optional presence of a known glutamate agonist, where antagonist activity is being tested). The electrophysiological properties of the glutamate receptors are measured following exposure to the test compound(s), and those that affect the ion channel response are concluded to be functional ligands for glutamate receptors.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

SUMMARY OF SEQUENCES

Sequence ID No. 1 shows the nucleotide and deduced amino acid sequence of the clone GluR1.

Sequence ID No. 2 is the deduced amino acid sequence of the clone GluR1.

Sequence ID No. 3 shows the nucleotide and deduced amino acid sequence of the clone GluR2.

Sequence ID No. 4 is the deduced amino acid sequence of the clone GluR2.

Sequence ID No. 5 shows the nucleotide and deduced amino acid sequence of the clone GluR3.

Sequence ID No. 6 is the deduced amino acid sequence of the clone GluR3.

Sequence ID No. 7 shows the nucleotide and deduced amino acid sequence of the clone GluR4.

Sequence ID No. 8 is the deduced amino acid sequence of the clone GluR4.

Sequence ID No. 9 shows the nucleotide and deduced amino acid sequence of the cDNA clone encoding glutamate receptor subunit GluR5-1.

Sequence ID No. 10 is the deduced amino acid sequence of the clone GluR5.

Sequence ID No. 11 shows the nucleotide and deduced amino acid sequence of the clone GluR6.

Sequence ID No. 12 is the deduced amino acid sequence of the clone GluR6.

Sequence ID No. 13 shows the nucleotide and deduced amino acid sequence of fragments clone GluR7.

Sequence ID No. 14 is the deduced amino acid sequence of the clone GluR7.

---

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 2992 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: GluR1

( i x ) FEATURE:

(A) NAME/KEY: CDS
(B) LOCATION: 198..2921

(xi) SEQUENCE DESCRIPTION: SEQ ID NO:1:

```
AATTCGGCAC GAGCTCGGCT CCCCTTCCAA GAGAAACAAG AGAAACCTCA CGGAAGGAAG         60

GGAGGAAGGA AAGAAGCAAG CAAGGAACTG CAGGAAGAAA AGAGCCGGCA GAGCATCAAG        120

AAGAATCGAA GGGAGGGGAG GGAAGACCAA ATCTATGGTT GGACCAGGGC TTCTTTTTCG        180

CCAATGTAAA AAGGAAT ATG CCG TAC ATC TTT GCC TTT TTC TGC ACC GGT          230
                   Met Pro Tyr Ile Phe Ala Phe Phe Cys Thr Gly
                    1               5                      10

TTT CTA GGT GCG GTT GTG GGT GCC AAT TTC CCC AAC AAT ATC CAG ATA         278
Phe Leu Gly Ala Val Val Gly Ala Asn Phe Pro Asn Asn Ile Gln Ile
            15              20                  25

GGG GGG TTA TTT CCA AAC CAA CAA TCA CAG GAA CAT GCG GCT TTT AGG         326
Gly Gly Leu Phe Pro Asn Gln Gln Ser Gln Glu His Ala Ala Phe Arg
        30                  35                  40

TTT GCT TTG TCA CAA CTC ACG GAG CCC CCC AAG CTG CTT CCC CAG ATC         374
Phe Ala Leu Ser Gln Leu Thr Glu Pro Pro Lys Leu Leu Pro Gln Ile
    45                  50                  55

GAT ATT GTG AAC ATC AGC GAC ACG TTT GAG ATG ACT TAC CGT TTC TGT         422
Asp Ile Val Asn Ile Ser Asp Thr Phe Glu Met Thr Tyr Arg Phe Cys
60              65                  70                      75

TCC CAG TTC TCC AAA GGA GTC TAT GCC ATC TTT GGA TTT TAT GAA CGA         470
Ser Gln Phe Ser Lys Gly Val Tyr Ala Ile Phe Gly Phe Tyr Glu Arg
                80                  85                      90

AGG ACT GTC AAC ATG CTG ACC TCC TTC TGT GGG GCC CTC CAT GTG TGC         518
Arg Thr Val Asn Met Leu Thr Ser Phe Cys Gly Ala Leu His Val Cys
            95                  100                 105

TTC ATT ACT CCA AGT TTT CCT GTT GAC ACA TCC AAT CAA TTT GTC CTT         566
Phe Ile Thr Pro Ser Phe Pro Val Asp Thr Ser Asn Gln Phe Val Leu
        110                 115                 120

CAG CTA CGC CCG GAA CTA CAG GAA GCT CTC ATT AGC ATT ATC GAC CAT         614
Gln Leu Arg Pro Glu Leu Gln Glu Ala Leu Ile Ser Ile Ile Asp His
    125                 130                 135

TAC AAG TGG CAA ACC TTT GTC TAC ATT TAT GAT GCT GAC CGG GGC CTG         662
Tyr Lys Trp Gln Thr Phe Val Tyr Ile Tyr Asp Ala Asp Arg Gly Leu
140                 145                 150                 155

TCA GTC CTG CAG AGA GTC TTG GAT ACA GCC GCA GAG AAG AAC TGG CAG         710
Ser Val Leu Gln Arg Val Leu Asp Thr Ala Ala Glu Lys Asn Trp Gln
                160                 165                 170

GTA ACG GCT GTC AAC ATT CTG ACA ACC ACC GAG GAA GGA TAC CGG ATG         758
Val Thr Ala Val Asn Ile Leu Thr Thr Thr Glu Glu Gly Tyr Arg Met
            175                 180                 185

CTC TTT CAG GAC CTG GAG AAG AAA AAG GAG AGG CTG GTG GTG GTT GAC         806
Leu Phe Gln Asp Leu Glu Lys Lys Lys Glu Arg Leu Val Val Val Asp
        190                 195                 200

TGT GAA TCA GAA CGC CTC AAC GCC ATC CTG GGC CAG ATC GTG AAG CTA         854
Cys Glu Ser Glu Arg Leu Asn Ala Ile Leu Gly Gln Ile Val Lys Leu
    205                 210                 215

GAA AAG AAT GGC ATC GGG TAC CAC TAC ATC CTC GCC AAT CTG GGC TTC         902
Glu Lys Asn Gly Ile Gly Tyr His Tyr Ile Leu Ala Asn Leu Gly Phe
220                 225                 230                 235

ATG GAC ATT GAC TTA AAT AAG TTC AAG GAG AGC GGA CGC AAT GTG ACA         950
Met Asp Ile Asp Leu Asn Lys Phe Lys Glu Ser Gly Arg Asn Val Thr
                240                 245                 250

GGT TTC CAG CTG GTG AAC TAC ACA GAC ACG ATC CCA GCC AGA ATC ATG         998
Gly Phe Gln Leu Val Asn Tyr Thr Asp Thr Ile Pro Ala Arg Ile Met
            255                 260                 265

CAG CAA TGG AGG ACA AGT GAC TCC CGA GAC CAT ACC AGG GTG GAC TGG        1046
Gln Gln Trp Arg Thr Ser Asp Ser Arg Asp His Thr Arg Val Asp Trp
        270                 275                 280
```

| | | | | | | | | | | | | | | | | |
|---|---|---|---|---|---|---|---|---|---|---|---|---|---|---|---|---|
| AAG | AGG | CCA | AAG | TAC | ACT | TCT | GCT | CTC | ACC | TAT | GAT | GGT | GTC | AAG | GTG | 1094 |
| Lys | Arg | Pro | Lys | Tyr | Thr | Ser | Ala | Leu | Thr | Tyr | Asp | Gly | Val | Lys | Val | |
| | 285 | | | | 290 | | | | | 295 | | | | | | |
| ATG | GCT | GAG | GCC | TTC | CAA | AGC | CTG | CGG | AGG | CAG | AGG | ATT | GAC | ATA | TCC | 1142 |
| Met | Ala | Glu | Ala | Phe | Gln | Ser | Leu | Arg | Arg | Gln | Arg | Ile | Asp | Ile | Ser | |
| 300 | | | | | 305 | | | | | 310 | | | | | 315 | |
| CGC | CGG | GGG | AAT | GCT | GGG | GAC | TGT | CTG | GCT | AAC | CCA | GCT | GTG | CCC | TGG | 1190 |
| Arg | Arg | Gly | Asn | Ala | Gly | Asp | Cys | Leu | Ala | Asn | Pro | Ala | Val | Pro | Trp | |
| | | | | 320 | | | | | 325 | | | | | 330 | | |
| GGT | CAA | GGG | ATC | GAC | ATC | CAG | AGA | GCC | CTG | CAG | CAG | GTG | CGC | TTC | GAA | 1238 |
| Gly | Gln | Gly | Ile | Asp | Ile | Gln | Arg | Ala | Leu | Gln | Gln | Val | Arg | Phe | Glu | |
| | | | 335 | | | | | 340 | | | | | 345 | | | |
| GGT | TTG | ACA | GGA | AAT | GTG | CAG | TTC | AAC | GAG | AAA | GGG | CGC | CGG | ACC | AAT | 1286 |
| Gly | Leu | Thr | Gly | Asn | Val | Gln | Phe | Asn | Glu | Lys | Gly | Arg | Arg | Thr | Asn | |
| | | 350 | | | | | 355 | | | | | 360 | | | | |
| TAC | ACC | CTC | CAC | GTG | ATC | GAA | ATG | AAA | CAT | GAT | GGA | ATC | CGA | AAG | ATT | 1334 |
| Tyr | Thr | Leu | His | Val | Ile | Glu | Met | Lys | His | Asp | Gly | Ile | Arg | Lys | Ile | |
| | 365 | | | | | 370 | | | | | 375 | | | | | |
| GGT | TAC | TGG | AAT | GAA | GAC | GAT | AAA | TTT | GTC | CCC | GCA | GCC | ACC | GAC | GCT | 1382 |
| Gly | Tyr | Trp | Asn | Glu | Asp | Asp | Lys | Phe | Val | Pro | Ala | Ala | Thr | Asp | Ala | |
| 380 | | | | | 385 | | | | | 390 | | | | | 395 | |
| CAG | GCT | GGA | GGG | GAC | AAC | TCA | AGC | GTC | CAG | AAT | AGG | ACC | TAC | ATC | GTC | 1430 |
| Gln | Ala | Gly | Gly | Asp | Asn | Ser | Ser | Val | Gln | Asn | Arg | Thr | Tyr | Ile | Val | |
| | | | | 400 | | | | | 405 | | | | | 410 | | |
| ACT | ACT | ATC | CTC | GAA | GAT | CCT | TAC | GTG | ATG | CTT | AAA | AAG | AAT | GCC | AAC | 1478 |
| Thr | Thr | Ile | Leu | Glu | Asp | Pro | Tyr | Val | Met | Leu | Lys | Lys | Asn | Ala | Asn | |
| | | | 415 | | | | | 420 | | | | | 425 | | | |
| CAG | TTT | GAG | GGC | AAT | GAC | CGC | TAT | GAG | GGC | TAC | TGT | GTG | GAG | CTG | GCT | 1526 |
| Gln | Phe | Glu | Gly | Asn | Asp | Arg | Tyr | Glu | Gly | Tyr | Cys | Val | Glu | Leu | Ala | |
| | | 430 | | | | | 435 | | | | | 440 | | | | |
| GCA | GAG | ATC | GCC | AAG | CAC | GTG | GGC | TAC | TCC | TAC | CGA | CTT | GAG | ATT | GTC | 1574 |
| Ala | Glu | Ile | Ala | Lys | His | Val | Gly | Tyr | Ser | Tyr | Arg | Leu | Glu | Ile | Val | |
| | 445 | | | | | 450 | | | | | 455 | | | | | |
| AGC | GAC | GGC | AAA | TAT | GGA | GCC | CGG | GAT | CCC | GAC | ACA | AAG | GCT | TGG | AAT | 1622 |
| Ser | Asp | Gly | Lys | Tyr | Gly | Ala | Arg | Asp | Pro | Asp | Thr | Lys | Ala | Trp | Asn | |
| 460 | | | | | 465 | | | | | 470 | | | | | 475 | |
| GGC | ATG | GTG | GGA | GAA | CTG | GTC | TAT | GGA | AGA | GCA | GAC | GTG | GCT | GTG | GCT | 1670 |
| Gly | Met | Val | Gly | Glu | Leu | Val | Tyr | Gly | Arg | Ala | Asp | Val | Ala | Val | Ala | |
| | | | | 480 | | | | | 485 | | | | | 490 | | |
| CCC | TTG | ACC | ATA | ACC | TTG | GTC | CGG | GAG | GAA | GTC | ATC | GAC | TTC | TCC | AAG | 1718 |
| Pro | Leu | Thr | Ile | Thr | Leu | Val | Arg | Glu | Glu | Val | Ile | Asp | Phe | Ser | Lys | |
| | | | 495 | | | | | 500 | | | | | 505 | | | |
| CCA | TTC | ATG | AGT | TTG | GGA | ATC | TCC | ATT | ATG | ATT | AAG | AAG | CCA | CAG | AAG | 1766 |
| Pro | Phe | Met | Ser | Leu | Gly | Ile | Ser | Ile | Met | Ile | Lys | Lys | Pro | Gln | Lys | |
| | | 510 | | | | | 515 | | | | | 520 | | | | |
| TCC | AAG | CCA | GGT | GTC | TTC | TCC | TTT | CTT | GAC | CCT | TTG | GCC | TAT | GAG | ATC | 1814 |
| Ser | Lys | Pro | Gly | Val | Phe | Ser | Phe | Leu | Asp | Pro | Leu | Ala | Tyr | Glu | Ile | |
| | 525 | | | | | 530 | | | | | 535 | | | | | |
| TGG | ATG | TGT | ATA | GTG | TTT | GCC | TAC | ATT | GGA | GTG | AGC | GTC | GTC | CTC | TTC | 1862 |
| Trp | Met | Cys | Ile | Val | Phe | Ala | Tyr | Ile | Gly | Val | Ser | Val | Val | Leu | Phe | |
| 540 | | | | | 545 | | | | | 550 | | | | | 555 | |
| CTG | GTC | AGC | CGT | TTC | AGC | CCC | TAC | GAA | TGG | CAC | AGC | GAA | GAG | TTT | GAA | 1910 |
| Leu | Val | Ser | Arg | Phe | Ser | Pro | Tyr | Glu | Trp | His | Ser | Glu | Glu | Phe | Glu | |
| | | | 560 | | | | | 565 | | | | | 570 | | | |
| GAG | GGA | CGA | GAC | CAG | ACA | ACC | AGT | GAC | CAG | TCA | AAT | GAG | TTT | GGC | ATA | 1958 |
| Glu | Gly | Arg | Asp | Gln | Thr | Thr | Ser | Asp | Gln | Ser | Asn | Glu | Phe | Gly | Ile | |
| | | | 575 | | | | | 580 | | | | | 585 | | | |
| TTC | AAC | AGC | CTG | TGG | TTC | TCC | CTG | GGG | GCC | TTC | ATG | CAG | CAA | GGA | TGT | 2006 |
| Phe | Asn | Ser | Leu | Trp | Phe | Ser | Leu | Gly | Ala | Phe | Met | Gln | Gln | Gly | Cys | |
| | | 590 | | | | | 595 | | | | | 600 | | | | |
| GAC | ATT | TCC | CCC | AGG | TCC | CTG | TCC | GGA | CGC | ATC | GTC | GGC | GGC | GTC | TGG | 2054 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
| Asp | Ile | Ser | Pro | Arg | Ser | Leu | Ser | Gly | Arg | Ile | Val | Gly | Gly | Val | Trp  |      |
|     | 605 |     |     |     | 610 |     |     |     |     | 615 |     |     |     |     |      |      |
| TGG | TTC | TTC | ACT | TTG | ATC | ATC | ATC | TCC | TCG | TAC | ACA | GCC | AAC | CTG | GCT  | 2102 |
| Trp | Phe | Phe | Thr | Leu | Ile | Ile | Ile | Ser | Ser | Tyr | Thr | Ala | Asn | Leu | Ala  |      |
| 620 |     |     |     |     | 625 |     |     |     | 630 |     |     |     |     |     | 635  |      |
| GCC | TTC | CTG | ACT | GTG | GAG | AGG | ATG | GTG | TCT | CCC | ATT | GAG | AGT | GCA | GAG  | 2150 |
| Ala | Phe | Leu | Thr | Val | Glu | Arg | Met | Val | Ser | Pro | Ile | Glu | Ser | Ala | Glu  |      |
|     |     |     |     | 640 |     |     |     |     | 645 |     |     |     |     | 650 |      |      |
| GAC | CTG | GCA | AAG | CAG | ACG | GAA | ATT | GCT | TAT | GGG | ACA | TTG | GAA | GCA | GGC  | 2198 |
| Asp | Leu | Ala | Lys | Gln | Thr | Glu | Ile | Ala | Tyr | Gly | Thr | Leu | Glu | Ala | Gly  |      |
|     |     |     |     | 655 |     |     |     |     | 660 |     |     |     |     | 665 |      |      |
| TCC | ACT | AAG | GAG | TTC | TTC | AGG | AGA | TCT | AAA | ATC | GCT | GTG | TTT | GAG | AAG  | 2246 |
| Ser | Thr | Lys | Glu | Phe | Phe | Arg | Arg | Ser | Lys | Ile | Ala | Val | Phe | Glu | Lys  |      |
|     |     | 670 |     |     |     |     | 675 |     |     |     |     | 680 |     |     |      |      |
| ATG | TGG | ACA | TAC | ATG | AAG | TCT | GCA | GAA | CCA | TCC | GTG | TTT | GTT | CGG | ACC  | 2294 |
| Met | Trp | Thr | Tyr | Met | Lys | Ser | Ala | Glu | Pro | Ser | Val | Phe | Val | Arg | Thr  |      |
|     | 685 |     |     |     |     | 690 |     |     |     |     | 695 |     |     |     |      |      |
| ACA | GAG | GAA | GGC | ATG | ATC | AGA | GTG | AGA | AAA | TCT | AAA | GGC | AAA | TAC | GCC  | 2342 |
| Thr | Glu | Glu | Gly | Met | Ile | Arg | Val | Arg | Lys | Ser | Lys | Gly | Lys | Tyr | Ala  |      |
| 700 |     |     |     |     | 705 |     |     |     |     | 710 |     |     |     |     | 715  |      |
| TAC | CTC | CTG | GAG | TCC | ACC | ATG | AAT | GAG | TAT | ATT | GAG | CAA | CGA | AAG | CCC  | 2390 |
| Tyr | Leu | Leu | Glu | Ser | Thr | Met | Asn | Glu | Tyr | Ile | Glu | Gln | Arg | Lys | Pro  |      |
|     |     |     |     | 720 |     |     |     |     | 725 |     |     |     |     | 730 |      |      |
| TGT | GAC | ACC | ATG | AAA | GTG | GGA | GGT | AAC | TTG | GAT | TCC | AAA | GGC | TAT | GGC  | 2438 |
| Cys | Asp | Thr | Met | Lys | Val | Gly | Gly | Asn | Leu | Asp | Ser | Lys | Gly | Tyr | Gly  |      |
|     |     |     | 735 |     |     |     |     | 740 |     |     |     |     | 745 |     |      |      |
| ATT | GCG | ACA | CCC | AAG | GGG | TCC | GCC | CTG | AGA | AAT | CCA | GTA | AAC | CTG | GCA  | 2486 |
| Ile | Ala | Thr | Pro | Lys | Gly | Ser | Ala | Leu | Arg | Asn | Pro | Val | Asn | Leu | Ala  |      |
|     |     | 750 |     |     |     |     | 755 |     |     |     |     | 760 |     |     |      |      |
| GTG | TTA | AAA | CTG | AAC | GAG | CAG | GGG | CTT | TTG | GAC | AAA | TTG | AAA | AAC | AAA  | 2534 |
| Val | Leu | Lys | Leu | Asn | Glu | Gln | Gly | Leu | Leu | Asp | Lys | Leu | Lys | Asn | Lys  |      |
| 765 |     |     |     |     | 770 |     |     |     |     | 775 |     |     |     |     |      |      |
| TGG | TGG | TAC | GAC | AAG | GGC | GAG | TGC | GGC | ACG | GGG | GGA | GGT | GAC | TCC | AAG  | 2582 |
| Trp | Trp | Tyr | Asp | Lys | Gly | Glu | Cys | Gly | Thr | Gly | Gly | Gly | Asp | Ser | Lys  |      |
| 780 |     |     |     |     | 785 |     |     |     |     | 790 |     |     |     |     | 795  |      |
| GAC | AAG | ACC | AGC | GCT | TTG | AGC | CTC | AGC | AAT | GTG | GCA | GGC | GTG | TTC | TAC  | 2630 |
| Asp | Lys | Thr | Ser | Ala | Leu | Ser | Leu | Ser | Asn | Val | Ala | Gly | Val | Phe | Tyr  |      |
|     |     |     |     | 800 |     |     |     |     | 805 |     |     |     |     | 810 |      |      |
| ATC | CTG | ATT | GGA | GGG | CTG | GGA | CTG | GCC | ATG | CTG | GTT | GCC | TTA | ATC | GAG  | 2678 |
| Ile | Leu | Ile | Gly | Gly | Leu | Gly | Leu | Ala | Met | Leu | Val | Ala | Leu | Ile | Glu  |      |
|     |     |     | 815 |     |     |     |     | 820 |     |     |     |     | 825 |     |      |      |
| TTC | TGC | TAC | AAA | TCC | CGT | AGC | GAG | TCG | AAG | CGG | ATG | AAG | GGT | TTC | TGT  | 2726 |
| Phe | Cys | Tyr | Lys | Ser | Arg | Ser | Glu | Ser | Lys | Arg | Met | Lys | Gly | Phe | Cys  |      |
|     |     | 830 |     |     |     |     | 835 |     |     |     |     | 840 |     |     |      |      |
| TTG | ATC | CCA | CAG | CAA | TCC | ATC | AAT | GAA | GCC | ATA | CGG | ACA | TCG | ACC | CTC  | 2774 |
| Leu | Ile | Pro | Gln | Gln | Ser | Ile | Asn | Glu | Ala | Ile | Arg | Thr | Ser | Thr | Leu  |      |
| 845 |     |     |     |     | 850 |     |     |     |     | 855 |     |     |     |     |      |      |
| CCC | CGG | AAC | AGT | GGG | GCA | GGA | GCC | AGC | GGA | GGA | GGC | GGC | AGT | GGA | GAG  | 2822 |
| Pro | Arg | Asn | Ser | Gly | Ala | Gly | Ala | Ser | Gly | Gly | Gly | Gly | Ser | Gly | Glu  |      |
| 860 |     |     |     |     | 865 |     |     |     |     | 870 |     |     |     |     | 875  |      |
| AAT | GGC | CGG | GTG | GTC | AGC | CAG | GAC | TTC | CCC | AAG | TCC | ATG | CAA | TCC | ATT  | 2870 |
| Asn | Gly | Arg | Val | Val | Ser | Gln | Asp | Phe | Pro | Lys | Ser | Met | Gln | Ser | Ile  |      |
|     |     |     |     | 880 |     |     |     |     | 885 |     |     |     |     | 890 |      |      |
| CCC | TGC | ATG | AGT | CAC | AGT | TCA | GGG | ATG | CCC | TTG | GGA | GCC | ACA | GGA | TTG  | 2918 |
| Pro | Cys | Met | Ser | His | Ser | Ser | Gly | Met | Pro | Leu | Gly | Ala | Thr | Gly | Leu  |      |
|     |     |     | 895 |     |     |     |     | 900 |     |     |     |     | 905 |     |      |      |

TAACTGGAGC AGACAGGAAA CCCTTGGGGA GCAGGCTCAG GCTTCCACAG CCCCATCCCA    2978

AGCCCTTCAG TGCC    2992

( 2 ) INFORMATION FOR SEQ ID NO:2:

(i) SEQUENCE CHARACTERISTICS:
  (A) LENGTH: 907 amino acids
  (B) TYPE: amino acid
  (D) TOPOLOGY: linear (ii) MOLECULE TYPE: protein (xi) SEQUENCE DESCRIPTION: SEQ ID NO:2:

```
Met Pro Tyr Ile Phe Ala Phe Phe Cys Thr Gly Phe Leu Gly Ala Val
 1               5                  10                  15

Val Gly Ala Asn Phe Pro Asn Asn Ile Gln Ile Gly Gly Leu Phe Pro
                20                  25                  30

Asn Gln Gln Ser Gln Glu His Ala Ala Phe Arg Phe Ala Leu Ser Gln
            35                  40                  45

Leu Thr Glu Pro Pro Lys Leu Leu Pro Gln Ile Asp Ile Val Asn Ile
        50                  55                  60

Ser Asp Thr Phe Glu Met Thr Tyr Arg Phe Cys Ser Gln Phe Ser Lys
 65                  70                  75                  80

Gly Val Tyr Ala Ile Phe Gly Phe Tyr Glu Arg Arg Thr Val Asn Met
                85                  90                  95

Leu Thr Ser Phe Cys Gly Ala Leu His Val Cys Phe Ile Thr Pro Ser
                100                 105                 110

Phe Pro Val Asp Thr Ser Asn Gln Phe Val Leu Gln Leu Arg Pro Glu
            115                 120                 125

Leu Gln Glu Ala Leu Ile Ser Ile Asp His Tyr Lys Trp Gln Thr
        130                 135                 140

Phe Val Tyr Ile Tyr Asp Ala Asp Arg Gly Leu Ser Val Leu Gln Arg
145                 150                 155                 160

Val Leu Asp Thr Ala Ala Glu Lys Asn Trp Gln Val Thr Ala Val Asn
                165                 170                 175

Ile Leu Thr Thr Thr Glu Glu Gly Tyr Arg Met Leu Phe Gln Asp Leu
                180                 185                 190

Glu Lys Lys Lys Glu Arg Leu Val Val Val Asp Cys Glu Ser Glu Arg
            195                 200                 205

Leu Asn Ala Ile Leu Gly Gln Ile Val Lys Leu Glu Lys Asn Gly Ile
        210                 215                 220

Gly Tyr His Tyr Ile Leu Ala Asn Leu Gly Phe Met Asp Ile Asp Leu
225                 230                 235                 240

Asn Lys Phe Lys Glu Ser Gly Arg Asn Val Thr Gly Phe Gln Leu Val
                245                 250                 255

Asn Tyr Thr Asp Thr Ile Pro Ala Arg Ile Met Gln Gln Trp Arg Thr
                260                 265                 270

Ser Asp Ser Arg Asp His Thr Arg Val Asp Trp Lys Arg Pro Lys Tyr
            275                 280                 285

Thr Ser Ala Leu Thr Tyr Asp Gly Val Lys Val Met Ala Glu Ala Phe
    290                 295                 300

Gln Ser Leu Arg Arg Gln Arg Ile Asp Ile Ser Arg Arg Gly Asn Ala
305                 310                 315                 320

Gly Asp Cys Leu Ala Asn Pro Ala Val Pro Trp Gly Gln Gly Ile Asp
                325                 330                 335

Ile Gln Arg Ala Leu Gln Gln Val Arg Phe Glu Gly Leu Thr Gly Asn
                340                 345                 350

Val Gln Phe Asn Glu Lys Gly Arg Arg Thr Asn Tyr Thr Leu His Val
            355                 360                 365

Ile Glu Met Lys His Asp Gly Ile Arg Lys Ile Gly Tyr Trp Asn Glu
        370                 375                 380

Asp Asp Lys Phe Val Pro Ala Ala Thr Asp Ala Gln Ala Gly Gly Asp
```

|     |     |     |     |     |     |     |     |     |     |     |     |     |     |     |
| --- | --- | --- | --- | --- | --- | --- | --- | --- | --- | --- | --- | --- | --- | --- |
| 385 |     |     |     |     | 390 |     |     |     |     | 395 |     |     |     | 400 |
| Asn | Ser | Ser | Val | Gln | Asn | Arg | Thr | Tyr | Ile | Val | Thr | Thr | Ile | Leu | Glu |
|     |     |     |     | 405 |     |     |     | 410 |     |     |     | 415 |     |     |
| Asp | Pro | Tyr | Val | Met | Leu | Lys | Lys | Asn | Ala | Asn | Gln | Phe | Glu | Gly | Asn |
|     |     |     | 420 |     |     |     | 425 |     |     |     | 430 |     |     |     |
| Asp | Arg | Tyr | Glu | Gly | Tyr | Cys | Val | Glu | Leu | Ala | Ala | Glu | Ile | Ala | Lys |
|     |     | 435 |     |     |     | 440 |     |     |     | 445 |     |     |     |     |
| His | Val | Gly | Tyr | Ser | Tyr | Arg | Leu | Glu | Ile | Val | Ser | Asp | Gly | Lys | Tyr |
|     | 450 |     |     |     | 455 |     |     |     | 460 |     |     |     |     |     |
| Gly | Ala | Arg | Asp | Pro | Asp | Thr | Lys | Ala | Trp | Asn | Gly | Met | Val | Gly | Glu |
| 465 |     |     |     | 470 |     |     |     | 475 |     |     |     |     |     | 480 |
| Leu | Val | Tyr | Gly | Arg | Ala | Asp | Val | Ala | Val | Ala | Pro | Leu | Thr | Ile | Thr |
|     |     |     | 485 |     |     |     |     | 490 |     |     |     |     | 495 |     |
| Leu | Val | Arg | Glu | Glu | Val | Ile | Asp | Phe | Ser | Lys | Pro | Phe | Met | Ser | Leu |
|     |     |     | 500 |     |     |     |     | 505 |     |     |     | 510 |     |     |
| Gly | Ile | Ser | Ile | Met | Ile | Lys | Lys | Pro | Gln | Lys | Ser | Lys | Pro | Gly | Val |
|     |     | 515 |     |     |     | 520 |     |     |     |     | 525 |     |     |     |
| Phe | Ser | Phe | Leu | Asp | Pro | Leu | Ala | Tyr | Glu | Ile | Trp | Met | Cys | Ile | Val |
|     | 530 |     |     |     | 535 |     |     |     |     | 540 |     |     |     |     |
| Phe | Ala | Tyr | Ile | Gly | Val | Ser | Val | Val | Leu | Phe | Leu | Val | Ser | Arg | Phe |
| 545 |     |     |     |     | 550 |     |     |     | 555 |     |     |     |     | 560 |
| Ser | Pro | Tyr | Glu | Trp | His | Ser | Glu | Glu | Phe | Glu | Glu | Gly | Arg | Asp | Gln |
|     |     |     |     | 565 |     |     |     | 570 |     |     |     | 575 |     |     |
| Thr | Thr | Ser | Asp | Gln | Ser | Asn | Glu | Phe | Gly | Ile | Phe | Asn | Ser | Leu | Trp |
|     |     |     | 580 |     |     |     |     | 585 |     |     |     | 590 |     |     |
| Phe | Ser | Leu | Gly | Ala | Phe | Met | Gln | Gln | Gly | Cys | Asp | Ile | Ser | Pro | Arg |
|     |     | 595 |     |     |     | 600 |     |     |     | 605 |     |     |     |     |
| Ser | Leu | Ser | Gly | Arg | Ile | Val | Gly | Gly | Val | Trp | Trp | Phe | Phe | Thr | Leu |
|     | 610 |     |     |     | 615 |     |     |     | 620 |     |     |     |     |     |
| Ile | Ile | Ile | Ser | Ser | Tyr | Thr | Ala | Asn | Leu | Ala | Ala | Phe | Leu | Thr | Val |
| 625 |     |     |     | 630 |     |     |     | 635 |     |     |     |     |     | 640 |
| Glu | Arg | Met | Val | Ser | Pro | Ile | Glu | Ser | Ala | Glu | Asp | Leu | Ala | Lys | Gln |
|     |     |     | 645 |     |     |     | 650 |     |     |     | 655 |     |     |     |
| Thr | Glu | Ile | Ala | Tyr | Gly | Thr | Leu | Glu | Ala | Gly | Ser | Thr | Lys | Glu | Phe |
|     |     |     | 660 |     |     |     | 665 |     |     |     | 670 |     |     |     |
| Phe | Arg | Arg | Ser | Lys | Ile | Ala | Val | Phe | Glu | Lys | Met | Trp | Thr | Tyr | Met |
|     |     | 675 |     |     |     | 680 |     |     |     | 685 |     |     |     |     |
| Lys | Ser | Ala | Glu | Pro | Ser | Val | Phe | Val | Arg | Thr | Thr | Glu | Glu | Gly | Met |
|     | 690 |     |     |     | 695 |     |     |     | 700 |     |     |     |     |     |
| Ile | Arg | Val | Arg | Lys | Ser | Lys | Gly | Lys | Tyr | Ala | Tyr | Leu | Leu | Glu | Ser |
| 705 |     |     |     | 710 |     |     |     | 715 |     |     |     |     |     | 720 |
| Thr | Met | Asn | Glu | Tyr | Ile | Glu | Gln | Arg | Lys | Pro | Cys | Asp | Thr | Met | Lys |
|     |     |     | 725 |     |     |     | 730 |     |     |     | 735 |     |     |     |
| Val | Gly | Gly | Asn | Leu | Asp | Ser | Lys | Gly | Tyr | Gly | Ile | Ala | Thr | Pro | Lys |
|     |     | 740 |     |     |     | 745 |     |     |     | 750 |     |     |     |     |
| Gly | Ser | Ala | Leu | Arg | Asn | Pro | Val | Asn | Leu | Ala | Val | Leu | Lys | Leu | Asn |
|     |     | 755 |     |     |     | 760 |     |     |     | 765 |     |     |     |     |
| Glu | Gln | Gly | Leu | Leu | Asp | Lys | Leu | Lys | Asn | Lys | Trp | Trp | Tyr | Asp | Lys |
|     | 770 |     |     |     | 775 |     |     |     | 780 |     |     |     |     |     |
| Gly | Glu | Cys | Gly | Thr | Gly | Gly | Asp | Ser | Lys | Asp | Lys | Thr | Ser | Ala |
| 785 |     |     |     | 790 |     |     |     | 795 |     |     |     |     | 800 |
| Leu | Ser | Leu | Ser | Asn | Val | Ala | Gly | Val | Phe | Tyr | Ile | Leu | Ile | Gly | Gly |
|     |     |     | 805 |     |     |     | 810 |     |     |     | 815 |     |     |
| Leu | Gly | Leu | Ala | Met | Leu | Val | Ala | Leu | Ile | Glu | Phe | Cys | Tyr | Lys | Ser |
|     |     |     | 820 |     |     |     | 825 |     |     |     | 830 |     |     |     |

| | | | | | | | | | | | | |
|---|---|---|---|---|---|---|---|---|---|---|---|---|
|Arg|Ser|Glu|Ser|Lys|Arg|Met|Lys|Gly|Phe|Cys|Leu|Ile|Pro|Gln|Gln|
| | |835| | | |840| | | |845| | |
|Ser|Ile|Asn|Glu|Ala|Ile|Arg|Thr|Ser|Thr|Leu|Pro|Arg|Asn|Ser|Gly|
| | |850| | | |855| | | |860| | |
|Ala|Gly|Ala|Ser|Gly|Gly|Gly|Gly|Ser|Gly|Glu|Asn|Gly|Arg|Val|Val|
|865| | | |870| | | |875| | | |880|
|Ser|Gln|Asp|Phe|Pro|Lys|Ser|Met|Gln|Ser|Ile|Pro|Cys|Met|Ser|His|
| | | |885| | | |890| | | |895| |
|Ser|Ser|Gly|Met|Pro|Leu|Gly|Ala|Thr|Gly|Leu|
| | | |900| | | |905| |

( 2 ) INFORMATION FOR SEQ ID NO:3:

( i ) SEQUENCE CHARACTERISTICS:
      ( A ) LENGTH: 3505 base pairs
      ( B ) TYPE: nucleic acid
      ( C ) STRANDEDNESS: single
      ( D ) TOPOLOGY: linear ( i i ) MOLECULE TYPE: cDNA ( v i i ) IMMEDIATE SOURCE:
      ( B ) CLONE: GluR2

( i x ) FEATURE:
      ( A ) NAME/KEY: CDS
      ( B ) LOCATION: 316..2967

( x i ) SEQUENCE DESCRIPTION: SEQ ID NO:3:

| | | |
|---|---|---|
|GAATTCGGCA CGAGGTGCAT GGGAGGGTGC TGATATTCCC AGACACCAGG ACTACAGCGG|60|
|CAGCTCAGCT AAAAACTGCA TTCAGCCAGT CCTCGGGACT TCGGGAGCAG GGACAGGACG|120|
|CAAGGCATCA ACAGCCACCA GCTACAACTG GAAATAAGG ATTCTTCTGC CTTCACTTCG|180|
|TGTTTTTAGC AGCTCCTTGC TAAATATCGA CCTCACAATG CAGAGGATCT AATTTGCTGA|240|
|GGAAAACAGT CAAAGAAGGA AGAGGAAGAA AGGGAAACGA GGGGATATTT TGTGGATGCT|300|
|CTACTTTTCT TGGAA ATG CAA AAG ATT ATG CAT ATT TCT GTC CTC CTT TCT|351|
|            Met Gln Lys Ile Met His Ile Ser Val Leu Leu Ser| |
|             1               5                      10| |

|CCT|GTT|TTA|TGG|GGA|CTG|ATT|TTT|GGT|GTC|TCT|TCT|AAC|AGC|ATA|CAG|399|
|Pro|Val|Leu|Trp|Gly|Leu|Ile|Phe|Gly|Val|Ser|Ser|Asn|Ser|Ile|Gln|
| | |15| | | |20| | | |25| | | |
|ATA|GGG|GGG|CTA|TTT|CCA|AGG|GGC|GCT|GAT|CAA|GAA|TAC|AGT|GCA|TTT|447|
|Ile|Gly|Gly|Leu|Phe|Pro|Arg|Gly|Ala|Asp|Gln|Glu|Tyr|Ser|Ala|Phe|
| |30| | | |35| | | |40| | | | |
|CGG|GTA|GGG|ATG|GTT|CAG|TTT|TCC|ACT|TCG|GAG|TTC|AGA|CTG|ACA|CCC|495|
|Arg|Val|Gly|Met|Val|Gln|Phe|Ser|Thr|Ser|Glu|Phe|Arg|Leu|Thr|Pro|
|45| | | |50| | | |55| | | |60|
|CAT|ATC|GAC|AAT|TTG|GAG|GTA|GCC|AAC|AGT|TTC|GCA|GTC|ACC|AAT|GCT|543|
|His|Ile|Asp|Asn|Leu|Glu|Val|Ala|Asn|Ser|Phe|Ala|Val|Thr|Asn|Ala|
| | | |65| | | |70| | | |75| |
|TTC|TGC|TCC|CAG|TTT|TCA|AGA|GGA|GTC|TAC|GCA|ATT|TTT|GGA|TTT|TAT|591|
|Phe|Cys|Ser|Gln|Phe|Ser|Arg|Gly|Val|Tyr|Ala|Ile|Phe|Gly|Phe|Tyr|
| | |80| | | |85| | | |90| | |
|GAC|AAG|AAG|TCT|GTA|AAT|ACC|ATC|ACA|TCA|TTC|TGT|GGG|ACA|CTC|CAT|639|
|Asp|Lys|Lys|Ser|Val|Asn|Thr|Ile|Thr|Ser|Phe|Cys|Gly|Thr|Leu|His|
| | |95| | | |100| | | |105| | |
|GTG|TCC|TTC|ATC|ACA|CCT|AGC|TTC|CCA|ACA|GAT|GGC|ACA|CAT|CCA|TTT|687|
|Val|Ser|Phe|Ile|Thr|Pro|Ser|Phe|Pro|Thr|Asp|Gly|Thr|His|Pro|Phe|
| |110| | | |115| | | |120| | | |
|GTC|ATC|CAG|ATG|CGA|CCT|GAC|CTC|AAA|GGA|GCA|CTC|CTT|AGC|TTG|ATT|735|
|Val|Ile|Gln|Met|Arg|Pro|Asp|Leu|Lys|Gly|Ala|Leu|Leu|Ser|Leu|Ile|
|125| | | |130| | | |135| | | |140|

| | | | | | | | | | | | | | | | | |
|---|---|---|---|---|---|---|---|---|---|---|---|---|---|---|---|---|
| GAG | TAC | TAC | CAA | TGG | GAC | AAG | TTC | GCA | TAC | CTC | TAT | GAC | AGT | GAC | AGA | 783 |
| Glu | Tyr | Tyr | Gln | Trp | Asp | Lys | Phe | Ala | Tyr | Leu | Tyr | Asp | Ser | Asp | Arg | |
| | | | | 145 | | | | 150 | | | | | 155 | | | |
| GGC | TTA | TCA | ACA | CTG | CAA | GCT | GTT | CTG | GAT | TCT | GCT | GCA | GAG | AAG | AAG | 831 |
| Gly | Leu | Ser | Thr | Leu | Gln | Ala | Val | Leu | Asp | Ser | Ala | Ala | Glu | Lys | Lys | |
| | | | 160 | | | | 165 | | | | | 170 | | | | |
| TGG | CAG | GTG | ACT | GCT | ATC | AAT | GTG | GGG | AAC | ATC | AAC | AAT | GAC | AAG | AAA | 879 |
| Trp | Gln | Val | Thr | Ala | Ile | Asn | Val | Gly | Asn | Ile | Asn | Asn | Asp | Lys | Lys | |
| | | 175 | | | | 180 | | | | | 185 | | | | | |
| GAT | GAG | ACC | TAC | AGA | TCG | CTC | TTT | CAA | GAT | CTG | GAG | TTA | AAA | AAA | GAA | 927 |
| Asp | Glu | Thr | Tyr | Arg | Ser | Leu | Phe | Gln | Asp | Leu | Glu | Leu | Lys | Lys | Glu | |
| | 190 | | | | 195 | | | | 200 | | | | | | | |
| CGG | CGT | GTA | ATC | CTG | GAC | TGT | GAA | AGG | GAT | AAA | GTA | AAT | GAC | ATT | GTG | 975 |
| Arg | Arg | Val | Ile | Leu | Asp | Cys | Glu | Arg | Asp | Lys | Val | Asn | Asp | Ile | Val | |
| 205 | | | | 210 | | | | 215 | | | | | 220 | | | |
| GAC | CAG | GTT | ATT | ACC | ATT | GGA | AAA | CAT | GTT | AAA | GGG | TAC | CAT | TAT | ATC | 1023 |
| Asp | Gln | Val | Ile | Thr | Ile | Gly | Lys | His | Val | Lys | Gly | Tyr | His | Tyr | Ile | |
| | | | | 225 | | | | | 230 | | | | | 235 | | |
| ATT | GCA | AAT | CTG | GGA | TTC | ACT | GAT | GGG | GAC | CTG | CTG | AAA | ATT | CAG | TTT | 1071 |
| Ile | Ala | Asn | Leu | Gly | Phe | Thr | Asp | Gly | Asp | Leu | Leu | Lys | Ile | Gln | Phe | |
| | | | 240 | | | | | 245 | | | | | 250 | | | |
| GGA | GGA | GCA | AAT | GTC | TCT | GGA | TTT | CAG | ATT | GTA | GAC | TAC | GAC | GAT | TCC | 1119 |
| Gly | Gly | Ala | Asn | Val | Ser | Gly | Phe | Gln | Ile | Val | Asp | Tyr | Asp | Asp | Ser | |
| | | 255 | | | | | 260 | | | | | 265 | | | | |
| CTG | GTG | TCT | AAA | TTT | ATA | GAA | AGA | TGG | TCA | ACA | CTG | GAA | GAG | AAA | GAA | 1167 |
| Leu | Val | Ser | Lys | Phe | Ile | Glu | Arg | Trp | Ser | Thr | Leu | Glu | Glu | Lys | Glu | |
| | 270 | | | | | 275 | | | | | 280 | | | | | |
| TAC | CCT | GGA | GCA | CAC | ACA | GCG | ACA | ATT | AAG | TAT | ACT | TCG | GCC | CTG | ACG | 1215 |
| Tyr | Pro | Gly | Ala | His | Thr | Ala | Thr | Ile | Lys | Tyr | Thr | Ser | Ala | Leu | Thr | |
| 285 | | | | | 290 | | | | | 295 | | | | | 300 | |
| TAT | GAT | GCT | GTC | CAA | GTG | ATG | ACT | GAA | GCA | TTC | CGT | AAC | CTT | CGG | AAG | 1263 |
| Tyr | Asp | Ala | Val | Gln | Val | Met | Thr | Glu | Ala | Phe | Arg | Asn | Leu | Arg | Lys | |
| | | | | 305 | | | | 310 | | | | | 315 | | | |
| CAG | AGG | ATT | GAA | ATA | TCC | CGG | AGA | GGA | AAT | GCA | GGG | GAT | TGT | TTG | GCC | 1311 |
| Gln | Arg | Ile | Glu | Ile | Ser | Arg | Arg | Gly | Asn | Ala | Gly | Asp | Cys | Leu | Ala | |
| | | | 320 | | | | | 325 | | | | | 330 | | | |
| AAC | CCA | GCT | GTG | CCC | TGG | GGA | CAA | GGG | GTC | GAA | ATA | GAA | AGG | GCC | CTC | 1359 |
| Asn | Pro | Ala | Val | Pro | Trp | Gly | Gln | Gly | Val | Glu | Ile | Glu | Arg | Ala | Leu | |
| | | 335 | | | | | 340 | | | | | 345 | | | | |
| AAG | CAG | GTT | CAA | GTT | GAA | GGC | CTC | TCT | GGA | AAT | ATA | AAG | TTT | GAC | CAG | 1407 |
| Lys | Gln | Val | Gln | Val | Glu | Gly | Leu | Ser | Gly | Asn | Ile | Lys | Phe | Asp | Gln | |
| | 350 | | | | | 355 | | | | | 360 | | | | | |
| AAT | GGA | AAA | CGA | ATA | AAC | TAC | ACA | ATT | AAC | ATC | ATG | GAG | CTC | AAA | ACA | 1455 |
| Asn | Gly | Lys | Arg | Ile | Asn | Tyr | Thr | Ile | Asn | Ile | Met | Glu | Leu | Lys | Thr | |
| 365 | | | | | 370 | | | | | 375 | | | | | 380 | |
| AAT | GGA | CCC | CGG | AAG | ATT | GGG | TAC | TGG | AGT | GAA | GTG | GAT | AAA | ATG | GTT | 1503 |
| Asn | Gly | Pro | Arg | Lys | Ile | Gly | Tyr | Trp | Ser | Glu | Val | Asp | Lys | Met | Val | |
| | | | | 385 | | | | | 390 | | | | | 395 | | |
| GTC | ACC | CTA | ACT | GAG | CTC | CCA | TCA | GGA | AAT | GAC | ACG | TCT | GGG | CTT | GAA | 1551 |
| Val | Thr | Leu | Thr | Glu | Leu | Pro | Ser | Gly | Asn | Asp | Thr | Ser | Gly | Leu | Glu | |
| | | | 400 | | | | 405 | | | | | 410 | | | | |
| AAC | AAA | ACT | GTG | GTG | GTC | ACC | ACA | ATA | TTG | GAA | TCT | CCA | TAT | GTT | ATG | 1599 |
| Asn | Lys | Thr | Val | Val | Val | Thr | Thr | Ile | Leu | Glu | Ser | Pro | Tyr | Val | Met | |
| | | 415 | | | | | 420 | | | | | 425 | | | | |
| ATG | AAG | AAA | AAT | CAT | GAA | ATG | CTT | GAA | GGG | AAT | GAG | CGT | TAC | GAG | GGC | 1647 |
| Met | Lys | Lys | Asn | His | Glu | Met | Leu | Glu | Gly | Asn | Glu | Arg | Tyr | Glu | Gly | |
| | | 430 | | | | 435 | | | | | 440 | | | | | |
| TAC | TGT | GTT | GAC | TTA | GCT | GCA | GAA | ATT | GCC | AAA | CAC | TGT | GGG | TTC | AAG | 1695 |
| Tyr | Cys | Val | Asp | Leu | Ala | Ala | Glu | Ile | Ala | Lys | His | Cys | Gly | Phe | Lys | |
| 445 | | | | | 450 | | | | | 455 | | | | | 460 | |
| TAC | AAG | CTG | ACT | ATT | GTT | GGG | GAT | GGC | AAG | TAT | GGG | GCC | AGG | GAT | GCC | 1743 |

```
Tyr Lys Leu Thr Ile Val Gly Asp Gly Lys Tyr Gly Ala Arg Asp Ala
                465             470             475

GAC ACC AAA ATT TGG AAT GGT ATG GTT GGA GAG CTT GTC TAC GGG AAA        1791
Asp Thr Lys Ile Trp Asn Gly Met Val Gly Glu Leu Val Tyr Gly Lys
            480             485             490

GCT GAC ATT GCA ATT GCT CCA TTA ACT ATC ACT CTC GTG AGA GAA GAG        1839
Ala Asp Ile Ala Ile Ala Pro Leu Thr Ile Thr Leu Val Arg Glu Glu
        495             500             505

GTG ATT GAC TTC TCC AAG CCC TTC ATG AGT CTT GGA ATC TCT ATC ATG        1887
Val Ile Asp Phe Ser Lys Pro Phe Met Ser Leu Gly Ile Ser Ile Met
    510             515             520

ATC AAG AAG CCT CAG AAG TCC AAA CCA GGA GTG TTT TCC TTT CTT GAT        1935
Ile Lys Lys Pro Gln Lys Ser Lys Pro Gly Val Phe Ser Phe Leu Asp
525             530             535             540

CCT TTA GCC TAT GAG ATC TGG ATG TGC ATT GTG TTT GCC TAC ATT GGG        1983
Pro Leu Ala Tyr Glu Ile Trp Met Cys Ile Val Phe Ala Tyr Ile Gly
            545             550             555

GTC AGT GTA GTT TTA TTC CTG GTC AGC AGA TTT AGC CCC TAC GAG TGG        2031
Val Ser Val Val Leu Phe Leu Val Ser Arg Phe Ser Pro Tyr Glu Trp
        560             565             570

CAC ACT GAG GAA TTT GAA GAT GGA AGA GAA ACA CAA AGT AGT GAA TCA        2079
His Thr Glu Glu Phe Glu Asp Gly Arg Glu Thr Gln Ser Ser Glu Ser
    575             580             585

ACT AAT GAA TTT GGG ATT TTT AAT AGT CTC TGG TTT TCC TTG GGT GCC        2127
Thr Asn Glu Phe Gly Ile Phe Asn Ser Leu Trp Phe Ser Leu Gly Ala
590             595             600

TTT ATG CGG CAG GGA TGC GAT ATT TCG CCA AGA TCC CTC TCT GGG CGC        2175
Phe Met Arg Gln Gly Cys Asp Ile Ser Pro Arg Ser Leu Ser Gly Arg
605             610             615             620

ATT GTT GGA GGT GTG TGG TGG TTC TTT ACC CTG ATC ATA ATC TCC TCC        2223
Ile Val Gly Gly Val Trp Trp Phe Phe Thr Leu Ile Ile Ile Ser Ser
            625             630             635

TAC ACG GCT AAC TTA GCT GCC TTC CTG ACT GTA GAG AGG ATG GTG TCT        2271
Tyr Thr Ala Asn Leu Ala Ala Phe Leu Thr Val Glu Arg Met Val Ser
        640             645             650

CCC ATC GAA AGT GCT GAG GAT CTG TCT AAG CAA ACA GAA ATT GCT TAT        2319
Pro Ile Glu Ser Ala Glu Asp Leu Ser Lys Gln Thr Glu Ile Ala Tyr
    655             660             665

GGA ACA TTA GAC TCT GGC TCC ACT AAA GAG TTT TTC AGG AGA TCT AAA        2367
Gly Thr Leu Asp Ser Gly Ser Thr Lys Glu Phe Phe Arg Arg Ser Lys
670             675             680

ATC GCA GTG TTT GAT AAA ATG TGG ACT TAT ATG AGG AGT GCA GAG CCC        2415
Ile Ala Val Phe Asp Lys Met Trp Thr Tyr Met Arg Ser Ala Glu Pro
685             690             695             700

TCT GTG TTT GTG AGG ACT ACC GCA GAA GGA GTA GCC AGA GTC CGG AAA        2463
Ser Val Phe Val Arg Thr Thr Ala Glu Gly Val Ala Arg Val Arg Lys
            705             710             715

TCC AAA GGA AAG TAT GCC TAC TTG CTG GAG TCC ACA ATG AAC GAG TAC        2511
Ser Lys Gly Lys Tyr Ala Tyr Leu Leu Glu Ser Thr Met Asn Glu Tyr
        720             725             730

ATC GAG CAG AGG AAG CCT TGT GAC ACC ATG AAA GTG GGA GGA AAC TTG        2559
Ile Glu Gln Arg Lys Pro Cys Asp Thr Met Lys Val Gly Gly Asn Leu
    735             740             745

GAT TCC AAA GGC TAC GGC ATC GCC ACA CCT AAA GGA TCC TCA TTA GGA        2607
Asp Ser Lys Gly Tyr Gly Ile Ala Thr Pro Lys Gly Ser Ser Leu Gly
750             755             760

AAT GCG GTT AAC CTC GCA GTA CTA AAA CTG AAT GAA CAA GGC CTG TTG        2655
Asn Ala Val Asn Leu Ala Val Leu Lys Leu Asn Glu Gln Gly Leu Leu
765             770             775             780

GAC AAA TTG AAA AAC AAA TGG TGG TAC GAC AAA GGA GAG TGC GGC AGC        2703
Asp Lys Leu Lys Asn Lys Trp Trp Tyr Asp Lys Gly Glu Cys Gly Ser
            785             790             795
```

| | | | | | | | | | | | | | | | | |
|---|---|---|---|---|---|---|---|---|---|---|---|---|---|---|---|---|
| GGG | GGA | GGT | GAT | TCC | AAG | GAA | AAG | ACC | AGT | GCC | CTC | AGT | CTG | AGC | AAC | 2751 |
| Gly | Gly | Gly | Asp | Ser | Lys | Glu | Lys | Thr | Ser | Ala | Leu | Ser | Leu | Ser | Asn | |
| | | | 800 | | | | 805 | | | | | | 810 | | | |
| GTT | GCT | GGA | GTA | TTC | TAC | ATC | CTT | GTC | GGG | GGC | CTT | GGT | TTG | GCA | ATG | 2799 |
| Val | Ala | Gly | Val | Phe | Tyr | Ile | Leu | Val | Gly | Gly | Leu | Gly | Leu | Ala | Met | |
| | | 815 | | | | | 820 | | | | | 825 | | | | |
| CTG | GTG | GCT | TTG | ATT | GAG | TTC | TGT | TAC | AAG | TCA | AGG | GCC | GAG | GCG | AAA | 2847 |
| Leu | Val | Ala | Leu | Ile | Glu | Phe | Cys | Tyr | Lys | Ser | Arg | Ala | Glu | Ala | Lys | |
| | 830 | | | | | 835 | | | | | 840 | | | | | |
| CGA | ATG | AAG | GTG | GCA | AAG | AAT | CCA | CAG | AAT | ATT | AAC | CCA | TCT | TCC | TCG | 2895 |
| Arg | Met | Lys | Val | Ala | Lys | Asn | Pro | Gln | Asn | Ile | Asn | Pro | Ser | Ser | Ser | |
| 845 | | | | | 850 | | | | | 855 | | | | | 860 | |
| CAG | AAT | TCC | CAG | AAT | TTT | GCA | ACT | TAT | AAG | GAA | GGT | TAC | AAC | GTA | TAT | 2943 |
| Gln | Asn | Ser | Gln | Asn | Phe | Ala | Thr | Tyr | Lys | Glu | Gly | Tyr | Asn | Val | Tyr | |
| | | | | 865 | | | | | 870 | | | | | 875 | | |
| GGC | ATC | GAG | AGT | GTT | AAA | ATT | TAGGGGATGA | CCTTGAGTGA | TGTCATGAGG | | | | | | | 2994 |
| Gly | Ile | Glu | Ser | Val | Lys | Ile | | | | | | | | | | |
| | | | 880 | | | | | | | | | | | | | |

| | | | | | |
|---|---|---|---|---|---|
| AGCAAGGCAA | GGCTGTCAAT | TACAGGAAGT | ACTGGAGAAA | ATGGACGTGT | TATGACTCCA | 3054 |
| GAATTTCCCA | AAGCAGTGCA | TGCTGTCCCT | TACGTGAGTC | CTGGCATGGG | AATGAATGTC | 3114 |
| AGTGTGACTG | ATCTCTCGTG | ATTGATAGGA | ACCTTCTGAG | TGCCTTACAC | AATGGTTTCC | 3174 |
| TTGTGTGTTT | ATTGTCAAAG | TGGTGAGAGG | CATCCGATAT | CTTGAAGGCT | TTTCTTTCAG | 3234 |
| CCAAGAATTC | TTAACTATGT | GGAGTTCACC | TTGAATTGTA | AGGAAAGATA | AATTACAAAC | 3294 |
| AGAGCATCAT | TTTCTACTCC | GATATCAGAG | GAAGCGTGGT | GGACATGCAC | AGCTAACATG | 3354 |
| GAAATACTAT | CATTTAACTG | AAGTCTTTGT | ACAGACAACA | AACCCGTTTC | CGCAGCCACT | 3414 |
| ATTGTTAGTC | TCTTGATTCA | TAATGACTTA | AGCACACTTG | ACATCAACTG | CATCAAGATG | 3474 |
| TGACCTGTTT | TATAAAAAAA | AAAAAAAAAA | A | | | 3505 |

( 2 ) INFORMATION FOR SEQ ID NO:4:

( i ) SEQUENCE CHARACTERISTICS:
          ( A ) LENGTH: 883 amino acids
          ( B ) TYPE: amino acid
          ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met | Gln | Lys | Ile | Met | His | Ile | Ser | Val | Leu | Leu | Ser | Pro | Val | Leu | Trp |
| 1 | | | | 5 | | | | | 10 | | | | | 15 | |
| Gly | Leu | Ile | Phe | Gly | Val | Ser | Ser | Asn | Ser | Ile | Gln | Ile | Gly | Gly | Leu |
| | | | 20 | | | | | 25 | | | | | 30 | | |
| Phe | Pro | Arg | Gly | Ala | Asp | Gln | Glu | Tyr | Ser | Ala | Phe | Arg | Val | Gly | Met |
| | | 35 | | | | | 40 | | | | | 45 | | | |
| Val | Gln | Phe | Ser | Thr | Ser | Glu | Phe | Arg | Leu | Thr | Pro | His | Ile | Asp | Asn |
| | 50 | | | | | 55 | | | | | 60 | | | | |
| Leu | Glu | Val | Ala | Asn | Ser | Phe | Ala | Val | Thr | Asn | Ala | Phe | Cys | Ser | Gln |
| 65 | | | | | 70 | | | | | 75 | | | | | 80 |
| Phe | Ser | Arg | Gly | Val | Tyr | Ala | Ile | Phe | Gly | Phe | Tyr | Asp | Lys | Lys | Ser |
| | | | | 85 | | | | | 90 | | | | | 95 | |
| Val | Asn | Thr | Ile | Thr | Ser | Phe | Cys | Gly | Thr | Leu | His | Val | Ser | Phe | Ile |
| | | | 100 | | | | | 105 | | | | | 110 | | |
| Thr | Pro | Ser | Phe | Pro | Thr | Asp | Gly | Thr | His | Pro | Phe | Val | Ile | Gln | Met |
| | | | 115 | | | | | 120 | | | | | 125 | | |
| Arg | Pro | Asp | Leu | Lys | Gly | Ala | Leu | Leu | Ser | Leu | Ile | Glu | Tyr | Tyr | Gln |
| | 130 | | | | | 135 | | | | | 140 | | | | |

-continued

| | | | | | | | | | | | | | | | |
|---|---|---|---|---|---|---|---|---|---|---|---|---|---|---|---|
|Trp|Asp|Lys|Phe|Ala|Tyr|Leu|Tyr|Asp|Ser|Asp|Arg|Gly|Leu|Ser|Thr|
|145| | | | |150| | | |155| | | | | |160|
|Leu|Gln|Ala|Val|Leu|Asp|Ser|Ala|Ala|Glu|Lys|Lys|Trp|Gln|Val|Thr|
| | | | |165| | | |170| | | | |175| | |
|Ala|Ile|Asn|Val|Gly|Asn|Ile|Asn|Asn|Asp|Lys|Lys|Asp|Glu|Thr|Tyr|
| | | |180| | | | |185| | | | |190| | |
|Arg|Ser|Leu|Phe|Gln|Asp|Leu|Glu|Leu|Lys|Lys|Glu|Arg|Arg|Val|Ile|
| | |195| | | | |200| | | | |205| | | |
|Leu|Asp|Cys|Glu|Arg|Asp|Lys|Val|Asn|Asp|Ile|Val|Asp|Gln|Val|Ile|
| |210| | | | |215| | | | |220| | | | |
|Thr|Ile|Gly|Lys|His|Val|Lys|Gly|Tyr|His|Tyr|Ile|Ile|Ala|Asn|Leu|
|225| | | | |230| | | |235| | | | | |240|
|Gly|Phe|Thr|Asp|Gly|Asp|Leu|Leu|Lys|Ile|Gln|Phe|Gly|Gly|Ala|Asn|
| | | | |245| | | |250| | | | |255| | |
|Val|Ser|Gly|Phe|Gln|Ile|Val|Asp|Tyr|Asp|Asp|Ser|Leu|Val|Ser|Lys|
| | | |260| | | |265| | | | |270| | | |
|Phe|Ile|Glu|Arg|Trp|Ser|Thr|Leu|Glu|Glu|Lys|Glu|Tyr|Pro|Gly|Ala|
| | |275| | | | |280| | | | |285| | | |
|His|Thr|Ala|Thr|Ile|Lys|Tyr|Thr|Ser|Ala|Leu|Thr|Tyr|Asp|Ala|Val|
| |290| | | | |295| | | | |300| | | | |
|Gln|Val|Met|Thr|Glu|Ala|Phe|Arg|Asn|Leu|Arg|Lys|Gln|Arg|Ile|Glu|
|305| | | | |310| | | |315| | | | | |320|
|Ile|Ser|Arg|Arg|Gly|Asn|Ala|Gly|Asp|Cys|Leu|Ala|Asn|Pro|Ala|Val|
| | | | |325| | | | |330| | | | |335| |
|Pro|Trp|Gly|Gln|Gly|Val|Glu|Ile|Glu|Arg|Ala|Leu|Lys|Gln|Val|Gln|
| | | | |340| | | | |345| | | | |350| |
|Val|Glu|Gly|Leu|Ser|Gly|Asn|Ile|Lys|Phe|Asp|Gln|Asn|Gly|Lys|Arg|
| | | |355| | | | |360| | | | |365| | |
|Ile|Asn|Tyr|Thr|Ile|Asn|Ile|Met|Glu|Leu|Lys|Thr|Asn|Gly|Pro|Arg|
| |370| | | | |375| | | | |380| | | | |
|Lys|Ile|Gly|Tyr|Trp|Ser|Glu|Val|Asp|Lys|Met|Val|Val|Thr|Leu|Thr|
|385| | | | |390| | | |395| | | | | |400|
|Glu|Leu|Pro|Ser|Gly|Asn|Asp|Thr|Ser|Gly|Leu|Glu|Asn|Lys|Thr|Val|
| | | | |405| | | | |410| | | | |415| |
|Val|Val|Thr|Thr|Ile|Leu|Glu|Ser|Pro|Tyr|Val|Met|Met|Lys|Lys|Asn|
| | | |420| | | | |425| | | | |430| | |
|His|Glu|Met|Leu|Glu|Gly|Asn|Glu|Arg|Tyr|Glu|Gly|Tyr|Cys|Val|Asp|
| | |435| | | | |440| | | | |445| | | |
|Leu|Ala|Ala|Glu|Ile|Ala|Lys|His|Cys|Gly|Phe|Lys|Tyr|Lys|Leu|Thr|
| |450| | | | |455| | | | |460| | | | |
|Ile|Val|Gly|Asp|Gly|Lys|Tyr|Gly|Ala|Arg|Asp|Ala|Asp|Thr|Lys|Ile|
|465| | | | |470| | | |475| | | | | |480|
|Trp|Asn|Gly|Met|Val|Gly|Glu|Leu|Val|Tyr|Gly|Lys|Ala|Asp|Ile|Ala|
| | | | |485| | | | |490| | | | |495| |
|Ile|Ala|Pro|Leu|Thr|Ile|Thr|Leu|Val|Arg|Glu|Glu|Val|Ile|Asp|Phe|
| | | |500| | | | |505| | | | |510| | |
|Ser|Lys|Pro|Phe|Met|Ser|Leu|Gly|Ile|Ser|Ile|Met|Ile|Lys|Lys|Pro|
| | |515| | | | |520| | | | |525| | | |
|Gln|Lys|Ser|Lys|Pro|Gly|Val|Phe|Ser|Phe|Leu|Asp|Pro|Leu|Ala|Tyr|
| |530| | | | |535| | | | |540| | | | |
|Glu|Ile|Trp|Met|Cys|Ile|Val|Phe|Ala|Tyr|Ile|Gly|Val|Ser|Val|Val|
|545| | | | |550| | | |555| | | | | |560|
|Leu|Phe|Leu|Val|Ser|Arg|Phe|Ser|Pro|Tyr|Glu|Trp|His|Thr|Glu|Glu|
| | | | |565| | | | |570| | | | |575| |
|Phe|Glu|Asp|Gly|Arg|Glu|Thr|Gln|Ser|Ser|Glu|Ser|Thr|Asn|Glu|Phe|

|     |     |     |     | 580 |     |     |     |     | 585 |     |     |     |     | 590 |     |
| --- | --- | --- | --- | --- | --- | --- | --- | --- | --- | --- | --- | --- | --- | --- | --- |
| Gly | Ile | Phe | Asn | Ser | Leu | Trp | Phe | Ser | Leu | Gly | Ala | Phe | Met | Arg | Gln |
|     |     |     |     | 595 |     |     |     |     | 600 |     |     |     |     | 605 |     |
| Gly | Cys | Asp | Ile | Ser | Pro | Arg | Ser | Leu | Ser | Gly | Arg | Ile | Val | Gly | Gly |
|     |     |     |     | 610 |     |     |     |     | 615 |     |     |     |     | 620 |     |
| Val | Trp | Trp | Phe | Phe | Thr | Leu | Ile | Ile | Ile | Ser | Ser | Tyr | Thr | Ala | Asn |
| 625 |     |     |     |     |     | 630 |     |     |     |     | 635 |     |     |     | 640 |
| Leu | Ala | Ala | Phe | Leu | Thr | Val | Glu | Arg | Met | Val | Ser | Pro | Ile | Glu | Ser |
|     |     |     |     | 645 |     |     |     |     | 650 |     |     |     |     | 655 |     |
| Ala | Glu | Asp | Leu | Ser | Lys | Gln | Thr | Glu | Ile | Ala | Tyr | Gly | Thr | Leu | Asp |
|     |     |     |     | 660 |     |     |     |     | 665 |     |     |     |     | 670 |     |
| Ser | Gly | Ser | Thr | Lys | Glu | Phe | Phe | Arg | Arg | Ser | Lys | Ile | Ala | Val | Phe |
|     |     |     |     | 675 |     |     |     |     | 680 |     |     |     |     | 685 |     |
| Asp | Lys | Met | Trp | Thr | Tyr | Met | Arg | Ser | Ala | Glu | Pro | Ser | Val | Phe | Val |
|     |     |     |     | 690 |     |     |     |     | 695 |     |     |     |     | 700 |     |
| Arg | Thr | Thr | Ala | Glu | Gly | Val | Ala | Arg | Val | Arg | Lys | Ser | Lys | Gly | Lys |
| 705 |     |     |     |     |     | 710 |     |     |     |     | 715 |     |     |     | 720 |
| Tyr | Ala | Tyr | Leu | Leu | Glu | Ser | Thr | Met | Asn | Glu | Tyr | Ile | Glu | Gln | Arg |
|     |     |     |     | 725 |     |     |     |     | 730 |     |     |     |     | 735 |     |
| Lys | Pro | Cys | Asp | Thr | Met | Lys | Val | Gly | Gly | Asn | Leu | Asp | Ser | Lys | Gly |
|     |     |     |     | 740 |     |     |     |     | 745 |     |     |     |     | 750 |     |
| Tyr | Gly | Ile | Ala | Thr | Pro | Lys | Gly | Ser | Ser | Leu | Gly | Asn | Ala | Val | Asn |
|     |     |     |     | 755 |     |     |     |     | 760 |     |     |     |     | 765 |     |
| Leu | Ala | Val | Leu | Lys | Leu | Asn | Glu | Gln | Gly | Leu | Leu | Asp | Lys | Leu | Lys |
|     |     |     |     | 770 |     |     |     |     | 775 |     |     |     |     | 780 |     |
| Asn | Lys | Trp | Trp | Tyr | Asp | Lys | Gly | Glu | Cys | Gly | Ser | Gly | Gly | Gly | Asp |
| 785 |     |     |     |     |     | 790 |     |     |     |     | 795 |     |     |     | 800 |
| Ser | Lys | Glu | Lys | Thr | Ser | Ala | Leu | Ser | Leu | Ser | Asn | Val | Ala | Gly | Val |
|     |     |     |     | 805 |     |     |     |     | 810 |     |     |     |     | 815 |     |
| Phe | Tyr | Ile | Leu | Val | Gly | Gly | Leu | Gly | Leu | Ala | Met | Leu | Val | Ala | Leu |
|     |     |     |     | 820 |     |     |     |     | 825 |     |     |     |     | 830 |     |
| Ile | Glu | Phe | Cys | Tyr | Lys | Ser | Arg | Ala | Glu | Ala | Lys | Arg | Met | Lys | Val |
|     |     |     |     | 835 |     |     |     |     | 840 |     |     |     |     | 845 |     |
| Ala | Lys | Asn | Pro | Gln | Asn | Ile | Asn | Pro | Ser | Ser | Ser | Gln | Asn | Ser | Gln |
|     |     |     |     | 850 |     |     |     |     | 855 |     |     |     |     | 860 |     |
| Asn | Phe | Ala | Thr | Tyr | Lys | Glu | Gly | Tyr | Asn | Val | Tyr | Gly | Ile | Glu | Ser |
| 865 |     |     |     |     |     | 870 |     |     |     |     | 875 |     |     |     | 880 |
| Val | Lys | Ile |     |     |     |     |     |     |     |     |     |     |     |     |     |

( 2 ) INFORMATION FOR SEQ ID NO:5:

( i ) SEQUENCE CHARACTERISTICS:
        ( A ) LENGTH: 3083 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: GluR3

( i x ) FEATURE:
        ( A ) NAME/KEY: CDS
        ( B ) LOCATION: 167..2833

( x i ) SEQUENCE DESCRIPTION: SEQ ID NO:5:

```
GCTCTCTCTC TCTCTCTCTC TCTCTCTCTC TCTCTCTCTC TCTCTCTCTC TTCTCTCAGA        60

AATCGCTTTG GGGAACCCAG CTTGCAGCCA ATGAACCCGC CTTCCAGATT GGTGTGAAGA       120
```

```
CAGAAGTGAG CTTCGTTTTA GGCGTCAAGC AGCCAGGCAG AAGAAA ATG GGG CAA                              175
                                                        Met Gly Gln
                                                         1

AGC GTG CTC CGG GCG GTC TTC TTT TTA GTC CTG GGG CTT TTG GGT CAT                              223
Ser Val Leu Arg Ala Val Phe Phe Leu Val Leu Gly Leu Leu Gly His
     5               10                  15

TCT CAC GGA GGA TTC CCC AAC ACC ATC AGC ATA GGT GGA CTT TTC ATG                              271
Ser His Gly Gly Phe Pro Asn Thr Ile Ser Ile Gly Gly Leu Phe Met
 20              25                  30                      35

AGA AAC ACG GTT CAG GAG CAC AGC GCT TTC CGC TTT GCT GTG CAG TTA                              319
Arg Asn Thr Val Gln Glu His Ser Ala Phe Arg Phe Ala Val Gln Leu
                 40                  45                      50

TAC AAC ACC AAC CAG AAC ACC ACT GAG AAG CCC TTC CAT TTG AAT TAC                              367
Tyr Asn Thr Asn Gln Asn Thr Thr Glu Lys Pro Phe His Leu Asn Tyr
             55                  60                      65

CAC GTA GAC CAC TTG GAT TCC TCC AAT AGT TTT TCT GTG ACT AAT GCT                              415
His Val Asp His Leu Asp Ser Ser Asn Ser Phe Ser Val Thr Asn Ala
         70                  75                      80

TTC TGC TCC CAG TTC TCC AGA GGG GTG TAT GCT ATC TTT GGA TTC TAT                              463
Phe Cys Ser Gln Phe Ser Arg Gly Val Tyr Ala Ile Phe Gly Phe Tyr
     85                  90                      95

GAC CAG ATG TCA ATG AAC ACC CTG ACC TCC TTC TGT GGG GCC CTG CAC                              511
Asp Gln Met Ser Met Asn Thr Leu Thr Ser Phe Cys Gly Ala Leu His
100                  105                 110                 115

ACA TCT TTT GTC ACA CCT AGC TTT CCC ACT GAT GCA GAT GTG CAG TTT                              559
Thr Ser Phe Val Thr Pro Ser Phe Pro Thr Asp Ala Asp Val Gln Phe
                 120                 125                     130

GTC ATC CAG ATG CGC CCA GCC TTG AAG GGT GCC ATT CTG AGT CTT CTC                              607
Val Ile Gln Met Arg Pro Ala Leu Lys Gly Ala Ile Leu Ser Leu Leu
             135                 140                     145

AGT TAC TAC AAG TGG GAG AAG TTT GTG TAC CTC TAT GAC ACA GAA CGA                              655
Ser Tyr Tyr Lys Trp Glu Lys Phe Val Tyr Leu Tyr Asp Thr Glu Arg
         150                 155                     160

GGG TTT TCT GTC CTA CAA GCA ATT ATG GAG GCA GCA GTG CAA AAC AAC                              703
Gly Phe Ser Val Leu Gln Ala Ile Met Glu Ala Ala Val Gln Asn Asn
     165                 170                     175

TGG CAA GTG ACA GCA AGG TCT GTG GGA AAC ATA AAG GAC GTC CAG GAA                              751
Trp Gln Val Thr Ala Arg Ser Val Gly Asn Ile Lys Asp Val Gln Glu
180                  185                 190                     195

TTC AGA CGC ATC ATT GAA GAA ATG GAC AGA AGG CAG GAA AAA CGA TAC                              799
Phe Arg Arg Ile Ile Glu Glu Met Asp Arg Arg Gln Glu Lys Arg Tyr
                 200                 205                     210

TTG ATT GAC TGT GAA GTC GAA AGG ATT AAC ACA ATT TTG GAA CAG GTT                              847
Leu Ile Asp Cys Glu Val Glu Arg Ile Asn Thr Ile Leu Glu Gln Val
             215                 220                     225

GTG ATC CTG GGG AAG CAT TCA AGA GGC TAT CAC TAC ATG CTT GCT AAC                              895
Val Ile Leu Gly Lys His Ser Arg Gly Tyr His Tyr Met Leu Ala Asn
         230                 235                     240

CTG GGT TTT ACT GAC ATT TTA CTG GAA AGA GTC ATG CAT GGG GGA GCC                              943
Leu Gly Phe Thr Asp Ile Leu Leu Glu Arg Val Met His Gly Gly Ala
     245                 250                     255

AAC ATT ACA GGT TTC CAG ATT GTC AAC AAT GAA AAC CCA ATG GTT CAG                              991
Asn Ile Thr Gly Phe Gln Ile Val Asn Asn Glu Asn Pro Met Val Gln
260                  265                 270                     275

CAG TTC ATA CAG CGC TGG GTG AGA CTG GAT GAA AGG GAA TTC CCT GAA                             1039
Gln Phe Ile Gln Arg Trp Val Arg Leu Asp Glu Arg Glu Phe Pro Glu
                 280                 285                     290

GCC AAG AAT GCA CCA CTG AAG TAT ACA TCT GCG CTG ACA CAT GAC GCA                             1087
Ala Lys Asn Ala Pro Leu Lys Tyr Thr Ser Ala Leu Thr His Asp Ala
             295                 300                     305

ATA TTG GTC ATA GCA GAA GCC TTC CGA TAC CTG AGG AGA CAG AGA GTG                             1135
Ile Leu Val Ile Ala Glu Ala Phe Arg Tyr Leu Arg Arg Gln Arg Val
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 310 |     |     |     |     | 315 |     |     |     |     |     | 320 |     |     |      |
| GAT | GTC | TCC | CGC | AGA | GGC | AGT | GCT | GGA | GAC | TGC | TTA | GCA | AAT | CCT | GCT | 1183 |
| Asp | Val | Ser | Arg | Arg | Gly | Ser | Ala | Gly | Asp | Cys | Leu | Ala | Asn | Pro | Ala |      |
|     | 325 |     |     |     | 330 |     |     |     |     | 335 |     |     |     |     |     |      |
| GTG | CCC | TGG | AGT | CAA | GGA | ATT | GAT | ATT | GAG | AGA | GCT | CTG | AAA | ATG | GTG | 1231 |
| Val | Pro | Trp | Ser | Gln | Gly | Ile | Asp | Ile | Glu | Arg | Ala | Leu | Lys | Met | Val |      |
| 340 |     |     |     |     | 345 |     |     |     |     | 350 |     |     |     |     | 355 |      |
| CAA | GTA | CAA | GGA | ATG | ACT | GGA | AAC | ATC | CAA | TTT | GAC | ACT | TAT | GGA | CGT | 1279 |
| Gln | Val | Gln | Gly | Met | Thr | Gly | Asn | Ile | Gln | Phe | Asp | Thr | Tyr | Gly | Arg |      |
|     |     |     |     | 360 |     |     |     |     | 365 |     |     |     |     | 370 |     |      |
| AGG | ACA | AAT | TAT | ACC | ATT | GAT | GTC | TAT | GAA | ATG | AAA | GTC | TCG | GGT | TCT | 1327 |
| Arg | Thr | Asn | Tyr | Thr | Ile | Asp | Val | Tyr | Glu | Met | Lys | Val | Ser | Gly | Ser |      |
|     |     |     | 375 |     |     |     |     | 380 |     |     |     |     | 385 |     |     |      |
| CGA | AAA | GCT | GGT | TAC | TGG | AAC | GAA | TAT | GAA | AGG | TTT | GTG | CCC | TTC | TCA | 1375 |
| Arg | Lys | Ala | Gly | Tyr | Trp | Asn | Glu | Tyr | Glu | Arg | Phe | Val | Pro | Phe | Ser |      |
|     |     | 390 |     |     |     |     | 395 |     |     |     |     | 400 |     |     |     |      |
| GAT | CAA | CAA | ATC | AGC | AAT | GAC | AGC | TCA | TCC | TCA | GAG | AAC | CGG | ACC | ATT | 1423 |
| Asp | Gln | Gln | Ile | Ser | Asn | Asp | Ser | Ser | Ser | Ser | Glu | Asn | Arg | Thr | Ile |      |
|     | 405 |     |     |     |     | 410 |     |     |     |     | 415 |     |     |     |     |      |
| GTA | GTG | ACT | ACC | ATT | CTG | GAA | TCA | CCA | TAT | GTG | ATG | TAT | AAA | AAG | AAT | 1471 |
| Val | Val | Thr | Thr | Ile | Leu | Glu | Ser | Pro | Tyr | Val | Met | Tyr | Lys | Lys | Asn |      |
| 420 |     |     |     |     | 425 |     |     |     |     | 430 |     |     |     |     | 435 |      |
| CAT | GAG | CAG | CTG | GAA | GGA | AAT | GAG | CGC | TAT | GAA | GGC | TAC | TGT | GTT | GAT | 1519 |
| His | Glu | Gln | Leu | Glu | Gly | Asn | Glu | Arg | Tyr | Glu | Gly | Tyr | Cys | Val | Asp |      |
|     |     |     |     | 440 |     |     |     |     | 445 |     |     |     |     | 450 |     |      |
| TTA | GCC | TAT | GAA | ATA | GCC | AAA | CAC | GTA | AGG | ATC | AAA | TAC | AAA | TTG | TCC | 1567 |
| Leu | Ala | Tyr | Glu | Ile | Ala | Lys | His | Val | Arg | Ile | Lys | Tyr | Lys | Leu | Ser |      |
|     |     |     | 455 |     |     |     |     | 460 |     |     |     |     | 465 |     |     |      |
| ATT | GTC | GGT | GAT | GGG | AAA | TAT | GGC | GCC | AGA | GAT | CCA | GAG | ACT | AAA | ATA | 1615 |
| Ile | Val | Gly | Asp | Gly | Lys | Tyr | Gly | Ala | Arg | Asp | Pro | Glu | Thr | Lys | Ile |      |
|     |     | 470 |     |     |     |     | 475 |     |     |     |     | 480 |     |     |     |      |
| TGG | AAT | GGC | ATG | GTT | GGG | GAA | CTT | GTC | TAT | GGA | AGA | GCT | GAT | ATA | GCT | 1663 |
| Trp | Asn | Gly | Met | Val | Gly | Glu | Leu | Val | Tyr | Gly | Arg | Ala | Asp | Ile | Ala |      |
|     | 485 |     |     |     |     | 490 |     |     |     |     | 495 |     |     |     |     |      |
| GTT | GCT | CCA | CTC | ACT | ATA | ACA | TTG | GTC | CGT | GAA | GAA | GTC | ATA | GAT | TTC | 1711 |
| Val | Ala | Pro | Leu | Thr | Ile | Thr | Leu | Val | Arg | Glu | Glu | Val | Ile | Asp | Phe |      |
| 500 |     |     |     |     | 505 |     |     |     |     | 510 |     |     |     |     | 515 |      |
| TCA | AAC | GCA | TTT | ATG | AGC | CTG | GGA | ATC | TCC | ATC | ATG | ATA | AAG | AAG | CCT | 1759 |
| Ser | Asn | Ala | Phe | Met | Ser | Leu | Gly | Ile | Ser | Ile | Met | Ile | Lys | Lys | Pro |      |
|     |     |     |     | 520 |     |     |     |     | 525 |     |     |     |     | 530 |     |      |
| CAG | AAA | TCA | AAG | CCA | GGC | GTC | TTT | TCA | TTC | CTG | GAT | CCT | TTG | GCT | TAT | 1807 |
| Gln | Lys | Ser | Lys | Pro | Gly | Val | Phe | Ser | Phe | Leu | Asp | Pro | Leu | Ala | Tyr |      |
|     |     |     | 535 |     |     |     |     | 540 |     |     |     |     | 545 |     |     |      |
| GAA | ATC | TGG | ATG | TGC | ATT | GTC | TTC | GCT | TAC | ATT | GGA | GTC | AGT | GTA | GTT | 1855 |
| Glu | Ile | Trp | Met | Cys | Ile | Val | Phe | Ala | Tyr | Ile | Gly | Val | Ser | Val | Val |      |
|     |     | 550 |     |     |     |     | 555 |     |     |     |     | 560 |     |     |     |      |
| CTC | TTC | CTA | GTC | AGC | AGA | TTT | AGC | CCT | TAT | GAA | TGG | CAC | TTG | GAA | GAC | 1903 |
| Leu | Phe | Leu | Val | Ser | Arg | Phe | Ser | Pro | Tyr | Glu | Trp | His | Leu | Glu | Asp |      |
|     | 565 |     |     |     |     | 570 |     |     |     |     | 575 |     |     |     |     |      |
| AAC | AAT | GAA | GAA | CCT | CGT | GAC | CCA | CAA | AGC | CCT | CCT | GAT | CCT | CCC | AAT | 1951 |
| Asn | Asn | Glu | Glu | Pro | Arg | Asp | Pro | Gln | Ser | Pro | Pro | Asp | Pro | Pro | Asn |      |
| 580 |     |     |     |     | 585 |     |     |     |     | 590 |     |     |     |     | 595 |      |
| GAA | TTT | GGA | ATA | TTT | AAC | AGT | CTT | TGG | TTT | TCC | TTG | GGT | GCT | TTC | ATG | 1999 |
| Glu | Phe | Gly | Ile | Phe | Asn | Ser | Leu | Trp | Phe | Ser | Leu | Gly | Ala | Phe | Met |      |
|     |     |     |     | 600 |     |     |     |     | 605 |     |     |     |     | 610 |     |      |
| CAG | CAA | GGA | TGT | GAT | ATT | TCT | CCA | AGA | TCA | CTT | TCT | GGG | CGC | ATT | GTT | 2047 |
| Gln | Gln | Gly | Cys | Asp | Ile | Ser | Pro | Arg | Ser | Leu | Ser | Gly | Arg | Ile | Val |      |
|     |     |     | 615 |     |     |     |     | 620 |     |     |     |     | 625 |     |     |      |
| GGA | GGG | GTT | TGG | TGG | TTC | TTC | ACC | CTG | ATC | ATA | ATC | TCT | TCC | TAC | ACT | 2095 |
| Gly | Gly | Val | Trp | Trp | Phe | Phe | Thr | Leu | Ile | Ile | Ile | Ser | Ser | Tyr | Thr |      |
|     |     | 630 |     |     |     |     | 635 |     |     |     |     | 640 |     |     |     |      |

| | | | | | | | | | | | | | | | |
|---|---|---|---|---|---|---|---|---|---|---|---|---|---|---|---|
| GCA | AAC | CTT | GCT | GCT | TTC | CTG | ACT | GTG | GAG | AGG | ATG | GTG | TCC | CCT | ATA |
| Ala | Asn | Leu | Ala | Ala | Phe | Leu | Thr | Val | Glu | Arg | Met | Val | Ser | Pro | Ile |
| | 645 | | | | | 650 | | | | | 655 | | | | |

2143

GAG AGC GCT GAA GAC TTA GCC AAG CAG ACT GAA ATT GCA TAT GGG ACC 2191
Glu Ser Ala Glu Asp Leu Ala Lys Gln Thr Glu Ile Ala Tyr Gly Thr
660             665             670             675

CTG GAC TCT GGT TCA ACA AAA GAA TTT TTC AGA CGA TCC AAA ATT GCT 2239
Leu Asp Ser Gly Ser Thr Lys Glu Phe Phe Arg Arg Ser Lys Ile Ala
            680             685             690

GTG TAT GAG AAA ATG TGG TCT TAC ATG AAA TCC GCA GAG CCA TCT GTG 2287
Val Tyr Glu Lys Met Trp Ser Tyr Met Lys Ser Ala Glu Pro Ser Val
        695             700             705

TTT ACC AAA ACA ACA GCT GAC GGG GTA GCC CGA GTT CGG AAG TCC AAG 2335
Phe Thr Lys Thr Thr Ala Asp Gly Val Ala Arg Val Arg Lys Ser Lys
    710             715             720

GGA AAG TTC GCC TTC CTG CTG GAG TCG ACC ATG AAC GAG TAC ATT GAG 2383
Gly Lys Phe Ala Phe Leu Leu Glu Ser Thr Met Asn Glu Tyr Ile Glu
725             730             735

CAG AGA AAG CCG TGC GAT ACG ATG AAA GTT GGT GGA AAT CTG GAT TCC 2431
Gln Arg Lys Pro Cys Asp Thr Met Lys Val Gly Gly Asn Leu Asp Ser
740             745             750             755

AAA GGC TAT GGT GTG GCA ACC CCT AAA GGC TCA GCA TTA GGA AAT GCT 2479
Lys Gly Tyr Gly Val Ala Thr Pro Lys Gly Ser Ala Leu Gly Asn Ala
            760             765             770

GTT AAC CTG GCA GTA TTA AAA CTG AAT GAG CAA GGC CTC TTG GAC AAA 2527
Val Asn Leu Ala Val Leu Lys Leu Asn Glu Gln Gly Leu Leu Asp Lys
        775             780             785

TTG AAA AAC AAA TGG TGG TAC GAC AAA GGA GAG TGC GGC AGC GGG GGC 2575
Leu Lys Asn Lys Trp Trp Tyr Asp Lys Gly Glu Cys Gly Ser Gly Gly
    790             795             800

GGT GAC TCC AAG GAC AAG ACC AGT GCT CTA AGC CTG AGC AAT GTG GCA 2623
Gly Asp Ser Lys Asp Lys Thr Ser Ala Leu Ser Leu Ser Asn Val Ala
805             810             815

GGC GTG TTC TAT ATA CTT GTC GGA GGT CTG GGC CTG GCC ATG ATG GTG 2671
Gly Val Phe Tyr Ile Leu Val Gly Gly Leu Gly Leu Ala Met Met Val
820             825             830             835

GCT TTG ATA GAA TTC TGT TAC AAA TCA CGG GCA GAG TCC AAA CGC ATG 2719
Ala Leu Ile Glu Phe Cys Tyr Lys Ser Arg Ala Glu Ser Lys Arg Met
            840             845             850

AAA CTC ACA AAG AAC ACC CAA AAC TTT AAG CCT GCT CCT GCC ACC AAC 2767
Lys Leu Thr Lys Asn Thr Gln Asn Phe Lys Pro Ala Pro Ala Thr Asn
        855             860             865

ACT CAG AAT TAC GCT ACA TAC AGA GAA GGC TAC AAC GTG TAT GGA ACA 2815
Thr Gln Asn Tyr Ala Thr Tyr Arg Glu Gly Tyr Asn Val Tyr Gly Thr
    870             875             880

GAA AGT GTT AAG ATC TAGGGATCCC TTCCCACCAG AAGCATGCAA TGAGAGGAAA 2870
Glu Ser Val Lys Ile
885

TCACTGAAAA CGTGGCTGCT TCAAGGATCC TGAGCCGGAT TTCACTCTCC CTGGTGTCGG 2930

GCATGACACG AATATTGCTG ATGGTGCAAT GACCTTTCAA TAGGAAAAAC TGATTTTTTT 2990

TTTCCTTCAG TGCCTTATGG AACACTCTGA GACTTGCGAC AATGCAAACC ATCATTGAAA 3050

TCTTTTTGCT TTGCTTGAAA AAAAAAAAA AAA 3083

( 2 ) INFORMATION FOR SEQ ID NO:6:

( i ) SEQUENCE CHARACTERISTICS:
( A ) LENGTH: 888 amino acids
( B ) TYPE: amino acid
( D ) TOPOLOGY: linear ( i i ) MOLECULE TYPE: protein ( x i ) SEQUENCE DESCRIPTION: SEQ ID NO:6:

| Met | Gly | Gln | Ser | Val | Leu | Arg | Ala | Val | Phe | Phe | Leu | Val | Leu | Gly | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Gly | His | Ser | His | Gly | Gly | Phe | Pro | Asn | Thr | Ile | Ser | Ile | Gly | Gly |
|     |     |     | 20  |     |     |     |     | 25  |     |     |     |     | 30  |     |     |

| Leu | Phe | Met | Arg | Asn | Thr | Val | Gln | Glu | His | Ser | Ala | Phe | Arg | Phe | Ala |
|     |     | 35  |     |     |     |     | 40  |     |     |     |     | 45  |     |     |     |

| Val | Gln | Leu | Tyr | Asn | Thr | Asn | Gln | Asn | Thr | Thr | Glu | Lys | Pro | Phe | His |
|     | 50  |     |     |     |     | 55  |     |     |     |     | 60  |     |     |     |     |

| Leu | Asn | Tyr | His | Val | Asp | His | Leu | Asp | Ser | Ser | Asn | Ser | Phe | Ser | Val |
| 65  |     |     |     |     | 70  |     |     |     |     | 75  |     |     |     |     | 80  |

| Thr | Asn | Ala | Phe | Cys | Ser | Gln | Phe | Ser | Arg | Gly | Val | Tyr | Ala | Ile | Phe |
|     |     |     |     | 85  |     |     |     |     | 90  |     |     |     |     | 95  |     |

| Gly | Phe | Tyr | Asp | Gln | Met | Ser | Met | Asn | Thr | Leu | Thr | Ser | Phe | Cys | Gly |
|     |     |     | 100 |     |     |     |     | 105 |     |     |     |     | 110 |     |     |

| Ala | Leu | His | Thr | Ser | Phe | Val | Thr | Pro | Ser | Phe | Pro | Thr | Asp | Ala | Asp |
|     |     | 115 |     |     |     |     | 120 |     |     |     |     | 125 |     |     |     |

| Val | Gln | Phe | Val | Ile | Gln | Met | Arg | Pro | Ala | Leu | Lys | Gly | Ala | Ile | Leu |
|     | 130 |     |     |     |     | 135 |     |     |     |     | 140 |     |     |     |     |

| Ser | Leu | Leu | Ser | Tyr | Tyr | Lys | Trp | Glu | Lys | Phe | Val | Tyr | Leu | Tyr | Asp |
| 145 |     |     |     |     | 150 |     |     |     |     | 155 |     |     |     |     | 160 |

| Thr | Glu | Arg | Gly | Phe | Ser | Val | Leu | Gln | Ala | Ile | Met | Glu | Ala | Ala | Val |
|     |     |     |     | 165 |     |     |     |     | 170 |     |     |     |     | 175 |     |

| Gln | Asn | Asn | Trp | Gln | Val | Thr | Ala | Arg | Ser | Val | Gly | Asn | Ile | Lys | Asp |
|     |     |     | 180 |     |     |     |     | 185 |     |     |     |     | 190 |     |     |

| Val | Gln | Glu | Phe | Arg | Arg | Ile | Ile | Glu | Glu | Met | Asp | Arg | Arg | Gln | Glu |
|     |     | 195 |     |     |     |     | 200 |     |     |     |     | 205 |     |     |     |

| Lys | Arg | Tyr | Leu | Ile | Asp | Cys | Glu | Val | Glu | Arg | Ile | Asn | Thr | Ile | Leu |
|     | 210 |     |     |     |     | 215 |     |     |     |     | 220 |     |     |     |     |

| Glu | Gln | Val | Val | Ile | Leu | Gly | Lys | His | Ser | Arg | Gly | Tyr | His | Tyr | Met |
| 225 |     |     |     |     | 230 |     |     |     |     | 235 |     |     |     |     | 240 |

| Leu | Ala | Asn | Leu | Gly | Phe | Thr | Asp | Ile | Leu | Leu | Glu | Arg | Val | Met | His |
|     |     |     |     | 245 |     |     |     |     | 250 |     |     |     |     | 255 |     |

| Gly | Gly | Ala | Asn | Ile | Thr | Gly | Phe | Gln | Ile | Val | Asn | Asn | Glu | Asn | Pro |
|     |     |     | 260 |     |     |     |     | 265 |     |     |     |     | 270 |     |     |

| Met | Val | Gln | Gln | Phe | Ile | Gln | Arg | Trp | Val | Arg | Leu | Asp | Glu | Arg | Glu |
|     |     | 275 |     |     |     |     | 280 |     |     |     |     | 285 |     |     |     |

| Phe | Pro | Glu | Ala | Lys | Asn | Ala | Pro | Leu | Lys | Tyr | Thr | Ser | Ala | Leu | Thr |
|     | 290 |     |     |     |     | 295 |     |     |     |     | 300 |     |     |     |     |

| His | Asp | Ala | Ile | Leu | Val | Ile | Ala | Glu | Ala | Phe | Arg | Tyr | Leu | Arg | Arg |
| 305 |     |     |     |     | 310 |     |     |     |     | 315 |     |     |     |     | 320 |

| Gln | Arg | Val | Asp | Val | Ser | Arg | Arg | Gly | Ser | Ala | Gly | Asp | Cys | Leu | Ala |
|     |     |     |     | 325 |     |     |     |     | 330 |     |     |     |     | 335 |     |

| Asn | Pro | Ala | Val | Pro | Trp | Ser | Gln | Gly | Ile | Asp | Ile | Glu | Arg | Ala | Leu |
|     |     |     | 340 |     |     |     |     | 345 |     |     |     |     | 350 |     |     |

| Lys | Met | Val | Gln | Val | Gln | Gly | Met | Thr | Gly | Asn | Ile | Gln | Phe | Asp | Thr |
|     |     | 355 |     |     |     |     | 360 |     |     |     |     | 365 |     |     |     |

| Tyr | Gly | Arg | Arg | Thr | Asn | Tyr | Thr | Ile | Asp | Val | Tyr | Glu | Met | Lys | Val |
|     | 370 |     |     |     |     | 375 |     |     |     |     | 380 |     |     |     |     |

| Ser | Gly | Ser | Arg | Lys | Ala | Gly | Tyr | Trp | Asn | Glu | Tyr | Glu | Arg | Phe | Val |
| 385 |     |     |     |     | 390 |     |     |     |     | 395 |     |     |     |     | 400 |

| Pro | Phe | Ser | Asp | Gln | Gln | Ile | Ser | Asn | Asp | Ser | Ser | Ser | Ser | Glu | Asn |
|     |     |     |     | 405 |     |     |     |     | 410 |     |     |     |     | 415 |     |

| Arg | Thr | Ile | Val | Val | Thr | Thr | Ile | Leu | Glu | Ser | Pro | Tyr | Val | Met | Tyr |
|     |     |     | 420 |     |     |     |     | 425 |     |     |     |     | 430 |     |     |

-continued

| | | | | | | | | | | | | | | |
|---|---|---|---|---|---|---|---|---|---|---|---|---|---|---|
| Lys | Lys | Asn | His | Glu | Gln | Leu | Glu | Gly | Asn | Glu | Arg | Tyr | Glu | Gly | Tyr |
| | | 435 | | | 440 | | | | | | 445 | | | | |
| Cys | Val | Asp | Leu | Ala | Tyr | Glu | Ile | Ala | Lys | His | Val | Arg | Ile | Lys | Tyr |
| | | 450 | | | | 455 | | | | | 460 | | | | |
| Lys | Leu | Ser | Ile | Val | Gly | Asp | Gly | Lys | Tyr | Gly | Ala | Arg | Asp | Pro | Glu |
| 465 | | | | | 470 | | | | 475 | | | | | | 480 |
| Thr | Lys | Ile | Trp | Asn | Gly | Met | Val | Gly | Glu | Leu | Val | Tyr | Gly | Arg | Ala |
| | | | | 485 | | | | | 490 | | | | | 495 | |
| Asp | Ile | Ala | Val | Ala | Pro | Leu | Thr | Ile | Thr | Leu | Val | Arg | Glu | Glu | Val |
| | | | | 500 | | | | | 505 | | | | | 510 | |
| Ile | Asp | Phe | Ser | Asn | Ala | Phe | Met | Ser | Leu | Gly | Ile | Ser | Ile | Met | Ile |
| | | | 515 | | | | 520 | | | | | 525 | | | |
| Lys | Lys | Pro | Gln | Lys | Ser | Lys | Pro | Gly | Val | Phe | Ser | Phe | Leu | Asp | Pro |
| | | 530 | | | | 535 | | | | | 540 | | | | |
| Leu | Ala | Tyr | Glu | Ile | Trp | Met | Cys | Ile | Val | Phe | Ala | Tyr | Ile | Gly | Val |
| 545 | | | | | 550 | | | | | 555 | | | | | 560 |
| Ser | Val | Val | Leu | Phe | Leu | Val | Ser | Arg | Phe | Ser | Pro | Tyr | Glu | Trp | His |
| | | | | 565 | | | | | 570 | | | | | 575 | |
| Leu | Glu | Asp | Asn | Glu | Glu | Pro | Arg | Asp | Pro | Gln | Ser | Pro | Pro | Asp | |
| | | | 580 | | | | 585 | | | | | 590 | | | |
| Pro | Pro | Asn | Glu | Phe | Gly | Ile | Phe | Asn | Ser | Leu | Trp | Phe | Ser | Leu | Gly |
| | | 595 | | | | | 600 | | | | | 605 | | | |
| Ala | Phe | Met | Gln | Gln | Gly | Cys | Asp | Ile | Ser | Pro | Arg | Ser | Leu | Ser | Gly |
| | 610 | | | | | 615 | | | | | 620 | | | | |
| Arg | Ile | Val | Gly | Gly | Val | Trp | Trp | Phe | Phe | Thr | Leu | Ile | Ile | Ile | Ser |
| 625 | | | | | 630 | | | | | 635 | | | | | 640 |
| Ser | Tyr | Thr | Ala | Asn | Leu | Ala | Ala | Phe | Leu | Thr | Val | Glu | Arg | Met | Val |
| | | | | 645 | | | | | 650 | | | | | 655 | |
| Ser | Pro | Ile | Glu | Ser | Ala | Glu | Asp | Leu | Ala | Lys | Gln | Thr | Glu | Ile | Ala |
| | | | 660 | | | | | 665 | | | | | 670 | | |
| Tyr | Gly | Thr | Leu | Asp | Ser | Gly | Ser | Thr | Lys | Glu | Phe | Phe | Arg | Arg | Ser |
| | | 675 | | | | | 680 | | | | | 685 | | | |
| Lys | Ile | Ala | Val | Tyr | Glu | Lys | Met | Trp | Ser | Tyr | Met | Lys | Ser | Ala | Glu |
| | 690 | | | | | 695 | | | | | 700 | | | | |
| Pro | Ser | Val | Phe | Thr | Lys | Thr | Thr | Ala | Asp | Gly | Val | Ala | Arg | Val | Arg |
| 705 | | | | | 710 | | | | | 715 | | | | | 720 |
| Lys | Ser | Lys | Gly | Lys | Phe | Ala | Phe | Leu | Leu | Glu | Ser | Thr | Met | Asn | Glu |
| | | | | 725 | | | | | 730 | | | | | 735 | |
| Tyr | Ile | Glu | Gln | Arg | Lys | Pro | Cys | Asp | Thr | Met | Lys | Val | Gly | Gly | Asn |
| | | | 740 | | | | | 745 | | | | | 750 | | |
| Leu | Asp | Ser | Lys | Gly | Tyr | Gly | Val | Ala | Thr | Pro | Lys | Gly | Ser | Ala | Leu |
| | | 755 | | | | | 760 | | | | | 765 | | | |
| Gly | Asn | Ala | Val | Asn | Leu | Ala | Val | Leu | Lys | Leu | Asn | Glu | Gln | Gly | Leu |
| | 770 | | | | | 775 | | | | | 780 | | | | |
| Leu | Asp | Lys | Leu | Lys | Asn | Lys | Trp | Trp | Tyr | Asp | Lys | Gly | Glu | Cys | Gly |
| 785 | | | | | 790 | | | | | 795 | | | | | 800 |
| Ser | Gly | Gly | Gly | Asp | Ser | Lys | Asp | Lys | Thr | Ser | Ala | Leu | Ser | Leu | Ser |
| | | | | 805 | | | | | 810 | | | | | 815 | |
| Asn | Val | Ala | Gly | Val | Phe | Tyr | Ile | Leu | Val | Gly | Gly | Leu | Gly | Leu | Ala |
| | | | 820 | | | | | 825 | | | | | 830 | | |
| Met | Met | Val | Ala | Leu | Ile | Glu | Phe | Cys | Tyr | Lys | Ser | Arg | Ala | Glu | Ser |
| | | 835 | | | | | 840 | | | | | 845 | | | |
| Lys | Arg | Met | Lys | Leu | Thr | Lys | Asn | Thr | Gln | Asn | Phe | Lys | Pro | Ala | Pro |
| | 850 | | | | | 855 | | | | | 860 | | | | |

| Ala | Thr | Asn | Thr | Gln | Asn | Tyr | Ala | Thr | Tyr | Arg | Glu | Gly | Tyr | Asn | Val |
|-----|-----|-----|-----|-----|-----|-----|-----|-----|-----|-----|-----|-----|-----|-----|-----|
| 865 |     |     |     | 870 |     |     |     |     | 875 |     |     |     |     | 880 |     |

| Tyr | Gly | Thr | Glu | Ser | Val | Lys | Ile |
|-----|-----|-----|-----|-----|-----|-----|-----|
|     |     |     |     | 885 |     |     |     |

( 2 ) INFORMATION FOR SEQ ID NO:7:

( i ) SEQUENCE CHARACTERISTICS:
        ( A ) LENGTH: 2971 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: GluR4

( i x ) FEATURE:
        ( A ) NAME/KEY: CDS
        ( B ) LOCATION: 162..2870

( x i ) SEQUENCE DESCRIPTION: SEQ ID NO:7:

```
GTAATGGAGT GTACGCAAAA TCCTCTGTCT GTGGACTCGC ACCAGAGCCT CCCAGAAAAC      60

CTGGGCGATC TGCGCCATCG TCTTCAATGC CTCTCTGAAA AGCCTTTAGC AAGACTGAGA     120

GAAAGAGAAA AGAGAGCGCG CCAGAGAGAG GAGCAAAGAA G ATG AGG ATT ATT        173
                                              Met Arg Ile Ile
                                               1
```

| TGC | AGG | CAG | ATT | GTC | TTG | TTG | TTT | TCT | GGA | TTT | TGG | GGA | CTC | GCC | ATG | 221 |
|-----|-----|-----|-----|-----|-----|-----|-----|-----|-----|-----|-----|-----|-----|-----|-----|-----|
| Cys | Arg | Gln | Ile | Val | Leu | Leu | Phe | Ser | Gly | Phe | Trp | Gly | Leu | Ala | Met |     |
| 5   |     |     |     |     | 10  |     |     |     |     | 15  |     |     |     |     | 20  |     |

| GGA | GCC | TTT | CCA | AGC | AGC | GTT | CAA | ATA | GGT | GGT | CTC | TTC | ATC | CGA | AAC | 269 |
|-----|-----|-----|-----|-----|-----|-----|-----|-----|-----|-----|-----|-----|-----|-----|-----|-----|
| Gly | Ala | Phe | Pro | Ser | Ser | Val | Gln | Ile | Gly | Gly | Leu | Phe | Ile | Arg | Asn |     |
|     |     |     |     | 25  |     |     |     |     | 30  |     |     |     |     | 35  |     |     |

| ACA | GAC | CAG | GAA | TAC | ACT | GCT | TTT | AGA | CTG | GCA | ATC | TTT | CTT | CAT | AAC | 317 |
|-----|-----|-----|-----|-----|-----|-----|-----|-----|-----|-----|-----|-----|-----|-----|-----|-----|
| Thr | Asp | Gln | Glu | Tyr | Thr | Ala | Phe | Arg | Leu | Ala | Ile | Phe | Leu | His | Asn |     |
|     |     |     | 40  |     |     |     |     | 45  |     |     |     |     | 50  |     |     |     |

| ACC | AGC | CCC | AAT | GCA | TCG | GAA | GCT | CCT | TTC | AAT | TTG | GTA | CCT | CAT | GTG | 365 |
|-----|-----|-----|-----|-----|-----|-----|-----|-----|-----|-----|-----|-----|-----|-----|-----|-----|
| Thr | Ser | Pro | Asn | Ala | Ser | Glu | Ala | Pro | Phe | Asn | Leu | Val | Pro | His | Val |     |
|     |     | 55  |     |     |     |     | 60  |     |     |     |     | 65  |     |     |     |     |

| GAC | AAC | ATT | GAG | ACT | GCC | AAC | AGT | TTT | GCT | GTG | ACA | AAC | GCC | TTC | TGT | 413 |
|-----|-----|-----|-----|-----|-----|-----|-----|-----|-----|-----|-----|-----|-----|-----|-----|-----|
| Asp | Asn | Ile | Glu | Thr | Ala | Asn | Ser | Phe | Ala | Val | Thr | Asn | Ala | Phe | Cys |     |
|     | 70  |     |     |     |     | 75  |     |     |     |     | 80  |     |     |     |     |     |

| TCC | CAG | TAT | TCT | AGA | GGG | GTG | TTT | GCC | ATT | TTT | GGA | CTC | TAT | GAC | AAG | 461 |
|-----|-----|-----|-----|-----|-----|-----|-----|-----|-----|-----|-----|-----|-----|-----|-----|-----|
| Ser | Gln | Tyr | Ser | Arg | Gly | Val | Phe | Ala | Ile | Phe | Gly | Leu | Tyr | Asp | Lys |     |
| 85  |     |     |     |     | 90  |     |     |     |     | 95  |     |     |     |     | 100 |     |

| AGA | TCC | GTG | CAT | ACC | TTG | ACC | TCG | TTC | TGC | AGG | CGT | CTG | CAC | ATC | TCT | 509 |
|-----|-----|-----|-----|-----|-----|-----|-----|-----|-----|-----|-----|-----|-----|-----|-----|-----|
| Arg | Ser | Val | His | Thr | Leu | Thr | Ser | Phe | Cys | Arg | Arg | Leu | His | Ile | Ser |     |
|     |     |     |     | 105 |     |     |     |     | 110 |     |     |     |     | 115 |     |     |

| CTC | ATC | ACA | CCA | AGC | TTT | CCC | ACT | GAA | GGG | GAG | AGC | CAG | TTT | GTG | CTG | 557 |
|-----|-----|-----|-----|-----|-----|-----|-----|-----|-----|-----|-----|-----|-----|-----|-----|-----|
| Leu | Ile | Thr | Pro | Ser | Phe | Pro | Thr | Glu | Gly | Glu | Ser | Gln | Phe | Val | Leu |     |
|     |     |     | 120 |     |     |     |     | 125 |     |     |     |     | 130 |     |     |     |

| CAG | CTA | AGA | CCT | TCA | CTG | AGA | GGT | GCA | CTC | CTG | AGC | CTC | CTG | GAT | CAC | 605 |
|-----|-----|-----|-----|-----|-----|-----|-----|-----|-----|-----|-----|-----|-----|-----|-----|-----|
| Gln | Leu | Arg | Pro | Ser | Leu | Arg | Gly | Ala | Leu | Leu | Ser | Leu | Leu | Asp | His |     |
|     |     | 135 |     |     |     |     | 140 |     |     |     |     | 145 |     |     |     |     |

| TAT | GAG | TGG | AAC | TGT | TTC | GTC | TTC | CTG | TAT | GAT | ACA | GAC | AGG | GGG | TAT | 653 |
|-----|-----|-----|-----|-----|-----|-----|-----|-----|-----|-----|-----|-----|-----|-----|-----|-----|
| Tyr | Glu | Trp | Asn | Cys | Phe | Val | Phe | Leu | Tyr | Asp | Thr | Asp | Arg | Gly | Tyr |     |
|     | 150 |     |     |     |     | 155 |     |     |     |     | 160 |     |     |     |     |     |

| TCA | ATA | CTT | CAA | GCT | ATA | ATG | GAA | AAA | GCA | GGA | CAA | AAT | GGA | TGG | CAT | 701 |
|-----|-----|-----|-----|-----|-----|-----|-----|-----|-----|-----|-----|-----|-----|-----|-----|-----|
| Ser | Ile | Leu | Gln | Ala | Ile | Met | Glu | Lys | Ala | Gly | Gln | Asn | Gly | Trp | His |     |
| 165 |     |     |     |     | 170 |     |     |     |     | 175 |     |     |     |     | 180 |     |

| GTC | AGT | GCA | ATA | TGT | GTG | GAA | AAT | TTT | AAT | GAT | GTC | AGC | TAC | AGG | CAA | 749 |
|-----|-----|-----|-----|-----|-----|-----|-----|-----|-----|-----|-----|-----|-----|-----|-----|-----|
| Val | Ser | Ala | Ile | Cys | Val | Glu | Asn | Phe | Asn | Asp | Val | Ser | Tyr | Arg | Gln |     |
|     |     |     |     | 185 |     |     |     |     | 190 |     |     |     |     | 195 |     |     |

```
CTG CTA GAA GAG CTT GAC AGA AGA CAA GAG AAG AAA TTT GTG ATA GAT      797
Leu Leu Glu Glu Leu Asp Arg Arg Gln Glu Lys Lys Phe Val Ile Asp
        200                 205                 210

TGT GAG ATA GAG AGG CTT CAA AAC ATT TTA GAA CAA ATT GTG AGT GTT      845
Cys Glu Ile Glu Arg Leu Gln Asn Ile Leu Glu Gln Ile Val Ser Val
            215                 220                 225

GGG AAG CAT GTC AAA GGC TAC CAT TAT ATC ATC GCA AAT TTG GGT TTC      893
Gly Lys His Val Lys Gly Tyr His Tyr Ile Ile Ala Asn Leu Gly Phe
        230                 235                 240

AAG GAT ATT TCT CTT GAG AGA TTT ATA CAT GGA GGA GCA AAT GTA ACA      941
Lys Asp Ile Ser Leu Glu Arg Phe Ile His Gly Gly Ala Asn Val Thr
245                 250                 255                 260

GGA TTC CAG TTG GTA GAT TTT AAT ACA CCC ATG GTA ACC AAA CTA ATG      989
Gly Phe Gln Leu Val Asp Phe Asn Thr Pro Met Val Thr Lys Leu Met
                265                 270                 275

GAT CGG TGG AAG AAA CTA GAT CAG AGA GAA TAT CCA GGT TCT GAA ACA     1037
Asp Arg Trp Lys Lys Leu Asp Gln Arg Glu Tyr Pro Gly Ser Glu Thr
            280                 285                 290

CCT CCA AAG TAC ACC TCT GCT CTC ACT TAT GAT GGA GTC CTG GTG ATG     1085
Pro Pro Lys Tyr Thr Ser Ala Leu Thr Tyr Asp Gly Val Leu Val Met
        295                 300                 305

GCT GAA ACT TTC CGA AGT CTC AGA AGA CAG AAA ATT GAT ATT TCA AGG     1133
Ala Glu Thr Phe Arg Ser Leu Arg Arg Gln Lys Ile Asp Ile Ser Arg
310                 315                 320

AGA GGA AAT GCT GGG GAC TGT CTG GCA AAC CCT GCT GCT CCC TGG GGC     1181
Arg Gly Asn Ala Gly Asp Cys Leu Ala Asn Pro Ala Ala Pro Trp Gly
325                 330                 335                 340

CAG GGA ATT GAC ATG GAG AGG ACA CTG AAG CAG GTT CGA ATT CAA GGG     1229
Gln Gly Ile Asp Met Glu Arg Thr Leu Lys Gln Val Arg Ile Gln Gly
                345                 350                 355

CTG ACT GGG AAT GTT CAA TTT GAC CAT TAT GGA CGT AGA GTT AAT TAC     1277
Leu Thr Gly Asn Val Gln Phe Asp His Tyr Gly Arg Arg Val Asn Tyr
            360                 365                 370

ACA ATG GAT GTG TTT GAA CTA AAA AGC ACA GGA CCT CGA AAG GTT GGC     1325
Thr Met Asp Val Phe Glu Leu Lys Ser Thr Gly Pro Arg Lys Val Gly
        375                 380                 385

TAC TGG AAT GAT ATG GAT AAA TTA GTC TTG ATT CAA GAT ATG CCT ACT     1373
Tyr Trp Asn Asp Met Asp Lys Leu Val Leu Ile Gln Asp Met Pro Thr
        390                 395                 400

CTG GGC AAT GAC ACA GCA GCT ATT GAG AAC AGA ACA GTG GTT GTA ACC     1421
Leu Gly Asn Asp Thr Ala Ala Ile Glu Asn Arg Thr Val Val Val Thr
405                 410                 415                 420

ACA ATT ATG GAA TCT CCC TAT GTT ATG TAC AAG AAA AAT CAT GAA ATG     1469
Thr Ile Met Glu Ser Pro Tyr Val Met Tyr Lys Lys Asn His Glu Met
                425                 430                 435

TTT GAA GGA AAT GAC AAG TAC GAA GGC TAC TGT GTA GAT CTG GCA TCG     1517
Phe Glu Gly Asn Asp Lys Tyr Glu Gly Tyr Cys Val Asp Leu Ala Ser
            440                 445                 450

GAA AGT GCA AAA CAT ATT GGT ATC AAA TAT AAA ATT GCC ATT GTT CCT     1565
Glu Ser Ala Lys His Ile Gly Ile Lys Tyr Lys Ile Ala Ile Val Pro
        455                 460                 465

GAT GGA AAA TAT GGA GCA AGG GAC GCA GAC ACT AAG ATC TGG AAT GGG     1613
Asp Gly Lys Tyr Gly Ala Arg Asp Ala Asp Thr Lys Ile Trp Asn Gly
        470                 475                 480

ATG GTA GGA GAG CTT GTG TAT GGG AAA GCA GAG ATT GCT ATT GCC CCT     1661
Met Val Gly Glu Leu Val Tyr Gly Lys Ala Glu Ile Ala Ile Ala Pro
485                 490                 495                 500

CTG ACA ATC ACA TTG GTT CGA GAG GAA GTC ATC GAT TTT TCT AAG CCT     1709
Leu Thr Ile Thr Leu Val Arg Glu Glu Val Ile Asp Phe Ser Lys Pro
                505                 510                 515

TTT ATG AGT TTA GGC ATC TCT ATC ATG ATC AAA AAA CCT CAG AAA TCT     1757
Phe Met Ser Leu Gly Ile Ser Ile Met Ile Lys Lys Pro Gln Lys Ser
```

-continued

|     |     |     | 520 |     |     |     |     | 525 |     |     |     |     | 530 |     |     |      |
|-----|-----|-----|-----|-----|-----|-----|-----|-----|-----|-----|-----|-----|-----|-----|-----|------|
| AAA | CCA | GGA | GTC | TTT | TCC | TTC | TTG | GAC | CCT | CTG | GCC | TAT | GAG | ATC | TGG | 1805 |
| Lys | Pro | Gly | Val | Phe | Ser | Phe | Leu | Asp | Pro | Leu | Ala | Tyr | Glu | Ile | Trp |      |
|     |     | 535 |     |     |     |     | 540 |     |     |     |     | 545 |     |     |     |      |
| ATG | TGC | ATA | GTG | TTT | GCA | TAC | ATT | GGT | GTC | AGT | GTG | GTC | TTG | TTC | CTA | 1853 |
| Met | Cys | Ile | Val | Phe | Ala | Tyr | Ile | Gly | Val | Ser | Val | Val | Leu | Phe | Leu |      |
|     |     | 550 |     |     |     |     | 555 |     |     |     |     | 560 |     |     |     |      |
| GTC | AGT | AGG | TTT | AGC | CCA | TAT | GAG | TGG | CAC | ACA | GAA | GAA | CCT | GAG | GAT | 1901 |
| Val | Ser | Arg | Phe | Ser | Pro | Tyr | Glu | Trp | His | Thr | Glu | Glu | Pro | Glu | Asp |      |
| 565 |     |     |     |     | 570 |     |     |     |     | 575 |     |     |     |     | 580 |      |
| GGG | AAG | GAA | GGA | CCC | AGT | GAC | CAG | CCT | CCC | AAT | GAA | TTT | GGC | ATC | TTT | 1949 |
| Gly | Lys | Glu | Gly | Pro | Ser | Asp | Gln | Pro | Pro | Asn | Glu | Phe | Gly | Ile | Phe |      |
|     |     |     |     | 585 |     |     |     |     | 590 |     |     |     |     | 595 |     |      |
| AAC | AGC | CTT | TGG | TTT | TCC | CTG | GGT | GCC | TTT | ATG | CAA | CAA | GGA | TGT | GAC | 1997 |
| Asn | Ser | Leu | Trp | Phe | Ser | Leu | Gly | Ala | Phe | Met | Gln | Gln | Gly | Cys | Asp |      |
|     |     |     | 600 |     |     |     |     | 605 |     |     |     |     | 610 |     |     |      |
| ATT | TCA | CCC | AGA | TCC | CTG | TCA | GGT | CGG | ATT | GTT | GGA | GGC | GTG | TGG | TGG | 2045 |
| Ile | Ser | Pro | Arg | Ser | Leu | Ser | Gly | Arg | Ile | Val | Gly | Gly | Val | Trp | Trp |      |
|     |     | 615 |     |     |     |     | 620 |     |     |     |     | 625 |     |     |     |      |
| TTC | TTC | ACA | CTC | ATC | ATT | ATA | TCG | TCC | TAC | ACT | GCT | AAT | CTG | GCT | GCA | 2093 |
| Phe | Phe | Thr | Leu | Ile | Ile | Ile | Ser | Ser | Tyr | Thr | Ala | Asn | Leu | Ala | Ala |      |
|     |     | 630 |     |     |     |     | 635 |     |     |     |     | 640 |     |     |     |      |
| TTC | CTT | ACT | GTG | GAG | AGA | ATG | GTC | TCC | CCC | ATA | GAA | AGT | GCA | GAA | GAC | 2141 |
| Phe | Leu | Thr | Val | Glu | Arg | Met | Val | Ser | Pro | Ile | Glu | Ser | Ala | Glu | Asp |      |
| 645 |     |     |     |     | 650 |     |     |     |     | 655 |     |     |     |     | 660 |      |
| CTG | GCC | AAA | CAA | ACA | GAA | ATT | GCC | TAT | GGA | ACA | CTT | GAT | TCT | GGG | TCA | 2189 |
| Leu | Ala | Lys | Gln | Thr | Glu | Ile | Ala | Tyr | Gly | Thr | Leu | Asp | Ser | Gly | Ser |      |
|     |     |     |     | 665 |     |     |     |     | 670 |     |     |     |     | 675 |     |      |
| ACA | AAA | GAA | TTC | TTC | AGA | AGA | TCA | AAA | ATA | GCA | GTG | TAT | GAA | AAG | ATG | 2237 |
| Thr | Lys | Glu | Phe | Phe | Arg | Arg | Ser | Lys | Ile | Ala | Val | Tyr | Glu | Lys | Met |      |
|     |     |     | 680 |     |     |     |     | 685 |     |     |     |     | 690 |     |     |      |
| TGG | ACC | TAC | ATG | CGA | TCG | GCA | GAG | CCG | TCT | GTG | TTC | ACT | AGA | ACT | ACA | 2285 |
| Trp | Thr | Tyr | Met | Arg | Ser | Ala | Glu | Pro | Ser | Val | Phe | Thr | Arg | Thr | Thr |      |
|     |     | 695 |     |     |     |     | 700 |     |     |     |     | 705 |     |     |     |      |
| GCT | GAG | GGC | GTG | GCT | CGT | GTC | CGC | AAG | TCC | AAG | GGC | AAA | TTT | GCC | TTT | 2333 |
| Ala | Glu | Gly | Val | Ala | Arg | Val | Arg | Lys | Ser | Lys | Gly | Lys | Phe | Ala | Phe |      |
|     |     | 710 |     |     |     |     | 715 |     |     |     |     | 720 |     |     |     |      |
| CTC | CTG | GAG | TCC | ACG | ATG | AAT | GAA | TAC | ATT | GAG | CAG | CGA | AAG | CCC | TGT | 2381 |
| Leu | Leu | Glu | Ser | Thr | Met | Asn | Glu | Tyr | Ile | Glu | Gln | Arg | Lys | Pro | Cys |      |
| 725 |     |     |     |     | 730 |     |     |     |     | 735 |     |     |     |     | 740 |      |
| GAC | ACG | ATG | AAA | GTG | GGA | GGA | AAC | CTG | GAT | TCC | AAA | GGC | TAT | GGT | GTA | 2429 |
| Asp | Thr | Met | Lys | Val | Gly | Gly | Asn | Leu | Asp | Ser | Lys | Gly | Tyr | Gly | Val |      |
|     |     |     |     | 745 |     |     |     |     | 750 |     |     |     |     | 755 |     |      |
| GCA | ACG | CCC | AAG | GGT | TCC | TCA | TTA | AGA | ACT | CCT | GTA | AAC | CTT | GCC | GTT | 2477 |
| Ala | Thr | Pro | Lys | Gly | Ser | Ser | Leu | Arg | Thr | Pro | Val | Asn | Leu | Ala | Val |      |
|     |     |     | 760 |     |     |     |     | 765 |     |     |     |     | 770 |     |     |      |
| TTG | AAA | CTC | AGT | GAG | GCA | GGC | GTC | TTA | GAC | AAG | CTG | AAA | AAC | AAA | TGG | 2525 |
| Leu | Lys | Leu | Ser | Glu | Ala | Gly | Val | Leu | Asp | Lys | Leu | Lys | Asn | Lys | Trp |      |
|     |     | 775 |     |     |     |     | 780 |     |     |     |     | 785 |     |     |     |      |
| TGG | TAC | GAT | AAA | GGT | GAA | TGT | GGA | CCC | AAG | GAC | TCG | GGA | AGC | AAG | GAC | 2573 |
| Trp | Tyr | Asp | Lys | Gly | Glu | Cys | Gly | Pro | Lys | Asp | Ser | Gly | Ser | Lys | Asp |      |
|     |     | 790 |     |     |     |     | 795 |     |     |     |     | 800 |     |     |     |      |
| AAG | ACG | AGT | GCC | TTG | AGC | CTG | AGC | AAC | GTA | GCA | GGC | GTC | TTC | TAC | ATT | 2621 |
| Lys | Thr | Ser | Ala | Leu | Ser | Leu | Ser | Asn | Val | Ala | Gly | Val | Phe | Tyr | Ile |      |
| 805 |     |     |     |     | 810 |     |     |     |     | 815 |     |     |     |     | 820 |      |
| CTG | GTT | GGC | GGC | CTG | GGC | TTG | GCA | ATG | CTG | GTG | GCT | TTG | ATA | GAG | TTC | 2669 |
| Leu | Val | Gly | Gly | Leu | Gly | Leu | Ala | Met | Leu | Val | Ala | Leu | Ile | Glu | Phe |      |
|     |     |     |     | 825 |     |     |     |     | 830 |     |     |     |     | 835 |     |      |
| TGT | TAC | AAG | TCC | AGG | GCA | GAG | GCG | AAG | AGA | ATG | AAG | CTG | ACT | TTT | TCC | 2717 |
| Cys | Tyr | Lys | Ser | Arg | Ala | Glu | Ala | Lys | Arg | Met | Lys | Leu | Thr | Phe | Ser |      |
|     |     |     | 840 |     |     |     |     | 845 |     |     |     |     | 850 |     |     |      |

| | | | | | | | | | | | | | | | | |
|---|---|---|---|---|---|---|---|---|---|---|---|---|---|---|---|---|
| GAA | GCC | ATA | AGA | AAC | AAA | GCC | AGG | TTA | TCC | ATC | ACT | GGG | AGT | GTG | GGA | 2765 |
| Glu | Ala | Ile | Arg | Asn | Lys | Ala | Arg | Leu | Ser | Ile | Thr | Gly | Ser | Val | Gly | |
| | | 855 | | | | | 860 | | | | | 865 | | | | |
| GAA | AAC | GGC | CGT | GTG | CTT | ACC | CCT | GAC | TGC | CCC | AAG | GCC | GTA | CAC | ACA | 2813 |
| Glu | Asn | Gly | Arg | Val | Leu | Thr | Pro | Asp | Cys | Pro | Lys | Ala | Val | His | Thr | |
| | | 870 | | | | | 875 | | | | | 880 | | | | |
| GGA | ACT | GCA | ATT | AGA | CAA | AGT | TCG | GGA | TTG | GCT | GTC | ATT | GCA | TCG | GAC | 2861 |
| Gly | Thr | Ala | Ile | Arg | Gln | Ser | Ser | Gly | Leu | Ala | Val | Ile | Ala | Ser | Asp | |
| 885 | | | | | 890 | | | | | 895 | | | | | 900 | |
| CTA | CCA | TAAAAACCAA | AAAAATAATT | GAGTGCCTTA | ATCAAACTGT | GTTGGTGACT | | | | | | | | | | 2917 |
| Leu | Pro | | | | | | | | | | | | | | | |

GACTGAAACG CAGCCCTGAG GGAAAGGCCA AGAGTGGGTC TTGACTAAAT CCAT    2971

( 2 ) INFORMATION FOR SEQ ID NO:8:

( i ) SEQUENCE CHARACTERISTICS:
        ( A ) LENGTH: 902 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| | | | | | | | | | | | | | | |
|---|---|---|---|---|---|---|---|---|---|---|---|---|---|---|
| Met | Arg | Ile | Ile | Cys | Arg | Gln | Ile | Val | Leu | Leu | Phe | Ser | Gly | Phe | Trp |
| 1 | | | | 5 | | | | | 10 | | | | | 15 | |
| Gly | Leu | Ala | Met | Gly | Ala | Phe | Pro | Ser | Ser | Val | Gln | Ile | Gly | Gly | Leu |
| | | | 20 | | | | | 25 | | | | 30 | | | |
| Phe | Ile | Arg | Asn | Thr | Asp | Gln | Glu | Tyr | Thr | Ala | Phe | Arg | Leu | Ala | Ile |
| | | 35 | | | | | 40 | | | | | 45 | | | |
| Phe | Leu | His | Asn | Thr | Ser | Pro | Asn | Ala | Ser | Glu | Ala | Pro | Phe | Asn | Leu |
| | 50 | | | | | 55 | | | | | 60 | | | | |
| Val | Pro | His | Val | Asp | Asn | Ile | Glu | Thr | Ala | Asn | Ser | Phe | Ala | Val | Thr |
| 65 | | | | | 70 | | | | | 75 | | | | | 80 |
| Asn | Ala | Phe | Cys | Ser | Gln | Tyr | Ser | Arg | Gly | Val | Phe | Ala | Ile | Phe | Gly |
| | | | | 85 | | | | | 90 | | | | | 95 | |
| Leu | Tyr | Asp | Lys | Arg | Ser | Val | His | Thr | Leu | Thr | Ser | Phe | Cys | Arg | Arg |
| | | | 100 | | | | | 105 | | | | | 110 | | |
| Leu | His | Ile | Ser | Leu | Ile | Thr | Pro | Ser | Phe | Pro | Thr | Glu | Gly | Glu | Ser |
| | | 115 | | | | | 120 | | | | | 125 | | | |
| Gln | Phe | Val | Leu | Gln | Leu | Arg | Pro | Ser | Leu | Arg | Gly | Ala | Leu | Leu | Ser |
| | 130 | | | | | 135 | | | | | 140 | | | | |
| Leu | Leu | Asp | His | Tyr | Glu | Trp | Asn | Cys | Phe | Val | Phe | Leu | Tyr | Asp | Thr |
| 145 | | | | | 150 | | | | | 155 | | | | | 160 |
| Asp | Arg | Gly | Tyr | Ser | Ile | Leu | Gln | Ala | Ile | Met | Glu | Lys | Ala | Gly | Gln |
| | | | | 165 | | | | | 170 | | | | | 175 | |
| Asn | Gly | Trp | His | Val | Ser | Ala | Ile | Cys | Val | Glu | Asn | Phe | Asn | Asp | Val |
| | | | 180 | | | | | 185 | | | | | 190 | | |
| Ser | Tyr | Arg | Gln | Leu | Leu | Glu | Glu | Leu | Asp | Arg | Arg | Gln | Glu | Lys | Lys |
| | | 195 | | | | | 200 | | | | | 205 | | | |
| Phe | Val | Ile | Asp | Cys | Glu | Ile | Glu | Arg | Leu | Gln | Asn | Ile | Leu | Glu | Gln |
| | 210 | | | | | 215 | | | | | 220 | | | | |
| Ile | Val | Ser | Val | Gly | Lys | His | Val | Lys | Gly | Tyr | His | Tyr | Ile | Ile | Ala |
| 225 | | | | | 230 | | | | | 235 | | | | | 240 |
| Asn | Leu | Gly | Phe | Lys | Asp | Ile | Ser | Leu | Glu | Arg | Phe | Ile | His | Gly | Gly |
| | | | | 245 | | | | | 250 | | | | | 255 | |
| Ala | Asn | Val | Thr | Gly | Phe | Gln | Leu | Val | Asp | Phe | Asn | Thr | Pro | Met | Val |
| | | | 260 | | | | | 265 | | | | | 270 | | |
| Thr | Lys | Leu | Met | Asp | Arg | Trp | Lys | Lys | Leu | Asp | Gln | Arg | Glu | Tyr | Pro |

-continued

|     | 275 |     |     |     |     | 280 |     |     |     |     | 285 |     |     |     |
|-----|-----|-----|-----|-----|-----|-----|-----|-----|-----|-----|-----|-----|-----|-----|
| Gly | Ser | Glu | Thr | Pro | Pro | Lys | Tyr | Thr | Ser | Ala | Leu | Thr | Tyr | Asp | Gly |
|     | 290 |     |     |     |     | 295 |     |     |     |     | 300 |     |     |     |     |
| Val | Leu | Val | Met | Ala | Glu | Thr | Phe | Arg | Ser | Leu | Arg | Arg | Gln | Lys | Ile |
| 305 |     |     |     |     | 310 |     |     |     |     | 315 |     |     |     |     | 320 |
| Asp | Ile | Ser | Arg | Arg | Gly | Asn | Ala | Gly | Asp | Cys | Leu | Ala | Asn | Pro | Ala |
|     |     |     |     | 325 |     |     |     |     | 330 |     |     |     |     | 335 |     |
| Ala | Pro | Trp | Gly | Gln | Gly | Ile | Asp | Met | Glu | Arg | Thr | Leu | Lys | Gln | Val |
|     |     |     | 340 |     |     |     |     | 345 |     |     |     |     | 350 |     |     |
| Arg | Ile | Gln | Gly | Leu | Thr | Gly | Asn | Val | Gln | Phe | Asp | His | Tyr | Gly | Arg |
|     |     | 355 |     |     |     |     | 360 |     |     |     |     | 365 |     |     |     |
| Arg | Val | Asn | Tyr | Thr | Met | Asp | Val | Phe | Glu | Leu | Lys | Ser | Thr | Gly | Pro |
|     | 370 |     |     |     |     | 375 |     |     |     |     | 380 |     |     |     |     |
| Arg | Lys | Val | Gly | Tyr | Trp | Asn | Asp | Met | Asp | Lys | Leu | Val | Leu | Ile | Gln |
| 385 |     |     |     |     | 390 |     |     |     |     | 395 |     |     |     |     | 400 |
| Asp | Met | Pro | Thr | Leu | Gly | Asn | Asp | Thr | Ala | Ala | Ile | Glu | Asn | Arg | Thr |
|     |     |     |     | 405 |     |     |     |     | 410 |     |     |     |     | 415 |     |
| Val | Val | Val | Thr | Thr | Ile | Met | Glu | Ser | Pro | Tyr | Val | Met | Tyr | Lys | Lys |
|     |     |     | 420 |     |     |     |     | 425 |     |     |     |     | 430 |     |     |
| Asn | His | Glu | Met | Phe | Glu | Gly | Asn | Asp | Lys | Tyr | Glu | Gly | Tyr | Cys | Val |
|     |     | 435 |     |     |     |     | 440 |     |     |     |     | 445 |     |     |     |
| Asp | Leu | Ala | Ser | Glu | Ser | Ala | Lys | His | Ile | Gly | Ile | Lys | Tyr | Lys | Ile |
|     | 450 |     |     |     |     | 455 |     |     |     |     | 460 |     |     |     |     |
| Ala | Ile | Val | Pro | Asp | Gly | Lys | Tyr | Gly | Ala | Arg | Asp | Ala | Asp | Thr | Lys |
| 465 |     |     |     |     | 470 |     |     |     |     | 475 |     |     |     |     | 480 |
| Ile | Trp | Asn | Gly | Met | Val | Gly | Glu | Leu | Val | Tyr | Gly | Lys | Ala | Glu | Ile |
|     |     |     |     | 485 |     |     |     |     | 490 |     |     |     |     | 495 |     |
| Ala | Ile | Ala | Pro | Leu | Thr | Ile | Thr | Leu | Val | Arg | Glu | Glu | Val | Ile | Asp |
|     |     |     | 500 |     |     |     |     | 505 |     |     |     |     | 510 |     |     |
| Phe | Ser | Lys | Pro | Phe | Met | Ser | Leu | Gly | Ile | Ser | Ile | Met | Ile | Lys | Lys |
|     |     | 515 |     |     |     |     | 520 |     |     |     |     | 525 |     |     |     |
| Pro | Gln | Lys | Ser | Lys | Pro | Gly | Val | Phe | Ser | Phe | Leu | Asp | Pro | Leu | Ala |
|     | 530 |     |     |     |     | 535 |     |     |     |     | 540 |     |     |     |     |
| Tyr | Glu | Ile | Trp | Met | Cys | Ile | Val | Phe | Ala | Tyr | Ile | Gly | Val | Ser | Val |
| 545 |     |     |     |     | 550 |     |     |     |     | 555 |     |     |     |     | 560 |
| Val | Leu | Phe | Leu | Val | Ser | Arg | Phe | Ser | Pro | Tyr | Glu | Trp | His | Thr | Glu |
|     |     |     |     | 565 |     |     |     |     | 570 |     |     |     |     | 575 |     |
| Glu | Pro | Glu | Asp | Gly | Lys | Glu | Gly | Pro | Ser | Asp | Gln | Pro | Pro | Asn | Glu |
|     |     |     | 580 |     |     |     |     | 585 |     |     |     |     | 590 |     |     |
| Phe | Gly | Ile | Phe | Asn | Ser | Leu | Trp | Phe | Ser | Leu | Gly | Ala | Phe | Met | Gln |
|     |     | 595 |     |     |     |     | 600 |     |     |     |     | 605 |     |     |     |
| Gln | Gly | Cys | Asp | Ile | Ser | Pro | Arg | Ser | Leu | Ser | Gly | Arg | Ile | Val | Gly |
|     | 610 |     |     |     |     | 615 |     |     |     |     | 620 |     |     |     |     |
| Gly | Val | Trp | Trp | Phe | Phe | Thr | Leu | Ile | Ile | Ile | Ser | Ser | Tyr | Thr | Ala |
| 625 |     |     |     |     | 630 |     |     |     |     | 635 |     |     |     |     | 640 |
| Asn | Leu | Ala | Ala | Phe | Leu | Thr | Val | Glu | Arg | Met | Val | Ser | Pro | Ile | Glu |
|     |     |     |     | 645 |     |     |     |     | 650 |     |     |     |     | 655 |     |
| Ser | Ala | Glu | Asp | Leu | Ala | Lys | Gln | Thr | Glu | Ile | Ala | Tyr | Gly | Thr | Leu |
|     |     |     | 660 |     |     |     |     | 665 |     |     |     |     | 670 |     |     |
| Asp | Ser | Gly | Ser | Thr | Lys | Glu | Phe | Phe | Arg | Arg | Ser | Lys | Ile | Ala | Val |
|     |     | 675 |     |     |     |     | 680 |     |     |     |     | 685 |     |     |     |
| Tyr | Glu | Lys | Met | Trp | Thr | Tyr | Met | Arg | Ser | Ala | Glu | Pro | Ser | Val | Phe |
|     | 690 |     |     |     |     | 695 |     |     |     |     | 700 |     |     |     |     |
| Thr | Arg | Thr | Thr | Ala | Glu | Gly | Val | Ala | Arg | Val | Arg | Lys | Ser | Lys | Gly |
| 705 |     |     |     |     | 710 |     |     |     |     | 715 |     |     |     |     | 720 |

-continued

| | | | | | | | | | | | | | | |
|---|---|---|---|---|---|---|---|---|---|---|---|---|---|---|
| Lys | Phe | Ala | Phe | Leu | Leu | Glu | Ser | Thr | Met | Asn | Glu | Tyr | Ile | Glu | Gln |
| | | | | 725 | | | | 730 | | | | | 735 | | |
| Arg | Lys | Pro | Cys | Asp | Thr | Met | Lys | Val | Gly | Gly | Asn | Leu | Asp | Ser | Lys |
| | | | 740 | | | | | 745 | | | | | 750 | | |
| Gly | Tyr | Gly | Val | Ala | Thr | Pro | Lys | Gly | Ser | Ser | Leu | Arg | Thr | Pro | Val |
| | | 755 | | | | | 760 | | | | | 765 | | | |
| Asn | Leu | Ala | Val | Leu | Lys | Leu | Ser | Glu | Ala | Gly | Val | Leu | Asp | Lys | Leu |
| | 770 | | | | | 775 | | | | | 780 | | | | |
| Lys | Asn | Lys | Trp | Trp | Tyr | Asp | Lys | Gly | Glu | Cys | Gly | Pro | Lys | Asp | Ser |
| 785 | | | | | 790 | | | | | 795 | | | | | 800 |
| Gly | Ser | Lys | Asp | Lys | Thr | Ser | Ala | Leu | Ser | Leu | Ser | Asn | Val | Ala | Gly |
| | | | | 805 | | | | | 810 | | | | | 815 | |
| Val | Phe | Tyr | Ile | Leu | Val | Gly | Gly | Leu | Gly | Leu | Ala | Met | Leu | Val | Ala |
| | | | 820 | | | | | | 825 | | | | | 830 | |
| Leu | Ile | Glu | Phe | Cys | Tyr | Lys | Ser | Arg | Ala | Glu | Ala | Lys | Arg | Met | Lys |
| | | 835 | | | | | | 840 | | | | | 845 | | |
| Leu | Thr | Phe | Ser | Glu | Ala | Ile | Arg | Asn | Lys | Ala | Arg | Leu | Ser | Ile | Thr |
| | 850 | | | | | | 855 | | | | | 860 | | | |
| Gly | Ser | Val | Gly | Glu | Asn | Gly | Arg | Val | Leu | Thr | Pro | Asp | Cys | Pro | Lys |
| 865 | | | | | 870 | | | | | 875 | | | | | 880 |
| Ala | Val | His | Thr | Gly | Thr | Ala | Ile | Arg | Gln | Ser | Ser | Gly | Leu | Ala | Val |
| | | | | 885 | | | | | 890 | | | | | 895 | |
| Ile | Ala | Ser | Asp | Leu | Pro | | | | | | | | | | |
| | | | 900 | | | | | | | | | | | | |

( 2 ) INFORMATION FOR SEQ ID NO:9:

( i ) SEQUENCE CHARACTERISTICS:
        ( A ) LENGTH: 3250 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: GluR5

( i x ) FEATURE:
        ( A ) NAME/KEY: CDS
        ( B ) LOCATION: 188..2950

( x i ) SEQUENCE DESCRIPTION: SEQ ID NO:9:

| | | | | | | | | | | | |
|---|---|---|---|---|---|---|---|---|---|---|---|
| GGCTAGGAAG | CCCGCTTCAC | GTCCCCACGC | TTGTTCCCTC | CACCTCGCTC | TCCTGAGAGC | | | | | | 60 |
| AGAGAGCGCG | CGGTGTGCAG | ACTCGGAGCA | TTCCGGGAGG | ATGAGGCGGG | GACCCAGCCC | | | | | | 120 |
| AAGTTGGGTG | CATCTTGCGG | GCGTGAGGCC | ACAACTGGGT | TTCGGCATGA | ATTAAGAAGC | | | | | | 180 |
| TTGAAAG | ATG | GAG | CGC | AGC | ACA | GTC | CTT | ATC | CAA | CCC | GGG | CTC | TGG | ACC | 229 |
| | Met | Glu | Arg | Ser | Thr | Val | Leu | Ile | Gln | Pro | Gly | Leu | Trp | Thr | |
| | 1 | | | | 5 | | | | | 10 | | | | | |
| AGG | GAC | ACC | AGC | TGG | ACA | CTC | CTC | TAT | TTC | CTG | TGC | TAC | ATC | CTC | CCT | 277 |
| Arg | Asp | Thr | Ser | Trp | Thr | Leu | Leu | Tyr | Phe | Leu | Cys | Tyr | Ile | Leu | Pro | |
| 15 | | | | | 20 | | | | | 25 | | | | | 30 | |
| CAG | ACC | TCC | CCT | CAA | GTG | CTC | AGG | ATC | GGA | GGG | ATT | TTT | GAA | ACT | GTG | 325 |
| Gln | Thr | Ser | Pro | Gln | Val | Leu | Arg | Ile | Gly | Gly | Ile | Phe | Glu | Thr | Val | |
| | | | | 35 | | | | | 40 | | | | | 45 | | |
| GAA | AAT | GAA | CCT | GTT | AAT | GTT | GAA | GAA | TTA | GCT | TTC | AAG | TTT | GCA | GTC | 373 |
| Glu | Asn | Glu | Pro | Val | Asn | Val | Glu | Glu | Leu | Ala | Phe | Lys | Phe | Ala | Val | |
| | | | 50 | | | | | 55 | | | | | 60 | | | |
| ACC | AGT | ATT | AAC | CGA | AAC | CGA | ACC | TTG | ATG | CCC | AAT | ACC | ACA | TTA | ACC | 421 |
| Thr | Ser | Ile | Asn | Arg | Asn | Arg | Thr | Leu | Met | Pro | Asn | Thr | Thr | Leu | Thr | |
| | | 65 | | | | | 70 | | | | | 75 | | | | |

-continued

| | | | | | | | | | | | | | | | | |
|---|---|---|---|---|---|---|---|---|---|---|---|---|---|---|---|---|
| TAT | GAC | ATC | CAG | AGA | ATT | AAT | CTT | TTT | GAT | AGT | TTT | GAA | GCC | TCC | CGA | 469 |
| Tyr | Asp | Ile | Gln | Arg | Ile | Asn | Leu | Phe | Asp | Ser | Phe | Glu | Ala | Ser | Arg | |
| | 80 | | | | 85 | | | | | 90 | | | | | | |
| AGA | GCA | TGC | GAC | CAG | CTG | GCT | CTC | GGG | GTG | GCC | GCA | CTC | TTC | GGC | CCT | 517 |
| Arg | Ala | Cys | Asp | Gln | Leu | Ala | Leu | Gly | Val | Ala | Ala | Leu | Phe | Gly | Pro | |
| 95 | | | | | 100 | | | | | 105 | | | | | 110 | |
| TCC | CAC | AGC | TCC | TCC | GTC | AGT | GCT | GTA | CAG | TCT | ATT | TGC | AAT | GCT | CTG | 565 |
| Ser | His | Ser | Ser | Ser | Val | Ser | Ala | Val | Gln | Ser | Ile | Cys | Asn | Ala | Leu | |
| | | | | 115 | | | | | 120 | | | | | 125 | | |
| GAA | GTT | CCA | CAC | ATT | CAG | ACT | CGC | TGG | AAA | CAC | CCT | TCC | GTG | GAC | AGC | 613 |
| Glu | Val | Pro | His | Ile | Gln | Thr | Arg | Trp | Lys | His | Pro | Ser | Val | Asp | Ser | |
| | | | 130 | | | | 135 | | | | | 140 | | | | |
| AGA | GAC | CTA | TTT | TAT | ATC | AAC | CTC | TAC | CCG | GAC | TAT | GCG | GCT | ATC | AGC | 661 |
| Arg | Asp | Leu | Phe | Tyr | Ile | Asn | Leu | Tyr | Pro | Asp | Tyr | Ala | Ala | Ile | Ser | |
| | | | 145 | | | | | 150 | | | | | 155 | | | |
| AGG | GCG | GTC | CTG | GAT | TTG | GTC | CTC | TAT | TAC | AAC | TGG | AAA | ACA | GTG | ACG | 709 |
| Arg | Ala | Val | Leu | Asp | Leu | Val | Leu | Tyr | Tyr | Asn | Trp | Lys | Thr | Val | Thr | |
| | 160 | | | | | 165 | | | | | 170 | | | | | |
| GTG | GTG | TAT | GAA | GAT | AGC | ACA | GGT | CTA | ATT | CGT | CTG | CAA | GAG | CTC | ATC | 757 |
| Val | Val | Tyr | Glu | Asp | Ser | Thr | Gly | Leu | Ile | Arg | Leu | Gln | Glu | Leu | Ile | |
| 175 | | | | | 180 | | | | | 185 | | | | | 190 | |
| AAA | GCT | CCC | TCC | AGA | TAC | AAC | ATT | AAA | ATC | AAA | ATC | CGC | CAG | CTT | CCC | 805 |
| Lys | Ala | Pro | Ser | Arg | Tyr | Asn | Ile | Lys | Ile | Lys | Ile | Arg | Gln | Leu | Pro | |
| | | | | 195 | | | | | 200 | | | | | 205 | | |
| CCT | GCG | AAT | AAA | GAC | GCC | AAA | CCT | CTG | CTC | AAG | GAG | ATG | AAG | AAA | AGC | 853 |
| Pro | Ala | Asn | Lys | Asp | Ala | Lys | Pro | Leu | Leu | Lys | Glu | Met | Lys | Lys | Ser | |
| | | | 210 | | | | | 215 | | | | | 220 | | | |
| AAA | GAG | TTC | TAT | GTG | ATA | TTT | GAT | TGT | TCG | CAC | GAA | ACA | GCT | GCG | GAA | 901 |
| Lys | Glu | Phe | Tyr | Val | Ile | Phe | Asp | Cys | Ser | His | Glu | Thr | Ala | Ala | Glu | |
| | | 225 | | | | | 230 | | | | | 235 | | | | |
| ATT | CTT | AAG | CAG | ATT | TTG | TTC | ATG | GGC | ATG | ATG | ACT | GAA | TAT | TAT | CAC | 949 |
| Ile | Leu | Lys | Gln | Ile | Leu | Phe | Met | Gly | Met | Met | Thr | Glu | Tyr | Tyr | His | |
| | 240 | | | | | 245 | | | | | 250 | | | | | |
| TAC | TTC | TTC | ACA | ACC | CTG | GAC | TTG | TTT | GCT | TTA | GAT | CTG | GAA | CTC | TAT | 997 |
| Tyr | Phe | Phe | Thr | Thr | Leu | Asp | Leu | Phe | Ala | Leu | Asp | Leu | Glu | Leu | Tyr | |
| 255 | | | | | 260 | | | | | 265 | | | | | 270 | |
| AGG | TAC | AGC | GGT | GTA | AAT | ATG | ACT | GGA | TTT | CGG | TTG | CTG | AAT | ATT | GAC | 1045 |
| Arg | Tyr | Ser | Gly | Val | Asn | Met | Thr | Gly | Phe | Arg | Leu | Leu | Asn | Ile | Asp | |
| | | | | 275 | | | | | 280 | | | | | 285 | | |
| AAC | CCT | CAC | GTG | TCA | TCC | ATC | ATT | GAG | AAG | TGG | TCC | ATG | GAG | AGG | TTG | 1093 |
| Asn | Pro | His | Val | Ser | Ser | Ile | Ile | Glu | Lys | Trp | Ser | Met | Glu | Arg | Leu | |
| | | | 290 | | | | | 295 | | | | | 300 | | | |
| CAG | GCC | CCG | CCC | AGA | CCC | GAG | ACT | GGT | CTT | CTG | GAT | GGC | ATG | ATG | ACA | 1141 |
| Gln | Ala | Pro | Pro | Arg | Pro | Glu | Thr | Gly | Leu | Leu | Asp | Gly | Met | Met | Thr | |
| | | 305 | | | | | 310 | | | | | 315 | | | | |
| ACT | GAA | GCA | GCG | CTG | ATG | TAC | GAT | GCT | GTG | TAC | ATG | GTA | GCC | ATT | GCG | 1189 |
| Thr | Glu | Ala | Ala | Leu | Met | Tyr | Asp | Ala | Val | Tyr | Met | Val | Ala | Ile | Ala | |
| | 320 | | | | | 325 | | | | | 330 | | | | | |
| TCC | CAC | CGT | GCC | TCT | CAG | CTG | ACC | GTC | AGC | TCC | CTG | CAG | TGC | CAT | CGA | 1237 |
| Ser | His | Arg | Ala | Ser | Gln | Leu | Thr | Val | Ser | Ser | Leu | Gln | Cys | His | Arg | |
| 335 | | | | | 340 | | | | | 345 | | | | | 350 | |
| CAT | AAG | CCA | TGG | CGC | CTT | GGA | CCC | AGA | TTT | ATG | AAC | CTC | ATC | AAA | GAG | 1285 |
| His | Lys | Pro | Trp | Arg | Leu | Gly | Pro | Arg | Phe | Met | Asn | Leu | Ile | Lys | Glu | |
| | | | | 355 | | | | | 360 | | | | | 365 | | |
| GCT | CGG | TGG | GAC | GGC | TTG | ACT | GGG | CGG | ATC | ACC | TTC | AAT | AAG | ACC | GAT | 1333 |
| Ala | Arg | Trp | Asp | Gly | Leu | Thr | Gly | Arg | Ile | Thr | Phe | Asn | Lys | Thr | Asp | |
| | | | 370 | | | | | 375 | | | | | 380 | | | |
| GGC | TTG | AGA | AAG | GAT | TTT | GAC | CTG | GAC | ATT | ATC | AGT | CTC | AAA | GAG | GAA | 1381 |
| Gly | Leu | Arg | Lys | Asp | Phe | Asp | Leu | Asp | Ile | Ile | Ser | Leu | Lys | Glu | Glu | |
| | | | 385 | | | | | 390 | | | | | 395 | | | |
| GGA | ACT | GAA | AAG | GCC | TCT | GGT | GAA | GTG | TCT | AAA | CAC | TTG | TAT | AAA | GTG | 1429 |

|  |  |  |  |  |  |  |  |  |  |  |  |  |  |  |  |
|---|---|---|---|---|---|---|---|---|---|---|---|---|---|---|---|
| Gly | Thr | Glu | Lys | Ala | Ser | Gly | Glu | Val | Ser | Lys | His | Leu | Tyr | Lys | Val |
|  | 400 |  |  |  |  | 405 |  |  |  |  | 410 |  |  |  |  |

| TGG | AAG | AAG | ATT | GGG | ATT | TGG | AAC | TCC | AAC | AGT | GGG | CTG | AAC | ATG | ACG | 1477 |
|---|---|---|---|---|---|---|---|---|---|---|---|---|---|---|---|---|
| Trp | Lys | Lys | Ile | Gly | Ile | Trp | Asn | Ser | Asn | Ser | Gly | Leu | Asn | Met | Thr |  |
| 415 |  |  |  | 420 |  |  |  |  | 425 |  |  |  |  |  | 430 |  |

| GAT | GGC | AAC | AGA | GAC | AGG | TCC | AAC | AAT | ATC | ACG | GAC | TCG | CTG | GCT | AAC | 1525 |
|---|---|---|---|---|---|---|---|---|---|---|---|---|---|---|---|---|
| Asp | Gly | Asn | Arg | Asp | Arg | Ser | Asn | Asn | Ile | Thr | Asp | Ser | Leu | Ala | Asn |  |
|  |  |  | 435 |  |  |  |  |  | 440 |  |  |  |  | 445 |  |  |

| CGC | ACA | CTC | ATT | GTC | ACC | ACT | ATT | CTG | GAA | GAG | CCC | TAC | GTG | ATG | TAC | 1573 |
|---|---|---|---|---|---|---|---|---|---|---|---|---|---|---|---|---|
| Arg | Thr | Leu | Ile | Val | Thr | Thr | Ile | Leu | Glu | Glu | Pro | Tyr | Val | Met | Tyr |  |
|  |  | 450 |  |  |  |  |  | 455 |  |  |  |  | 460 |  |  |  |

| AGG | AAA | TCC | GAT | AAG | CCC | TTG | TAT | GGA | AAC | GAC | AGG | TTT | GAA | GGA | TAT | 1621 |
|---|---|---|---|---|---|---|---|---|---|---|---|---|---|---|---|---|
| Arg | Lys | Ser | Asp | Lys | Pro | Leu | Tyr | Gly | Asn | Asp | Arg | Phe | Glu | Gly | Tyr |  |
|  | 465 |  |  |  |  | 470 |  |  |  |  | 475 |  |  |  |  |  |

| TGC | CTG | GAT | CTG | CTG | AAA | GAA | CTG | TCC | AAT | ATC | CTG | GGT | TTT | CTT | TAC | 1669 |
|---|---|---|---|---|---|---|---|---|---|---|---|---|---|---|---|---|
| Cys | Leu | Asp | Leu | Leu | Lys | Glu | Leu | Ser | Asn | Ile | Leu | Gly | Phe | Leu | Tyr |  |
| 480 |  |  |  |  | 485 |  |  |  |  | 490 |  |  |  |  |  |  |

| GAT | GTT | AAA | CTG | GTT | CCT | GAT | GGC | AAA | TAT | GGA | GCA | CAG | AAT | GAC | AAA | 1717 |
|---|---|---|---|---|---|---|---|---|---|---|---|---|---|---|---|---|
| Asp | Val | Lys | Leu | Val | Pro | Asp | Gly | Lys | Tyr | Gly | Ala | Gln | Asn | Asp | Lys |  |
| 495 |  |  |  |  | 500 |  |  |  |  | 505 |  |  |  |  | 510 |  |

| GGG | GAA | TGG | AAT | GGG | ATG | GTA | AAA | GAA | CTC | ATC | GAC | CAC | AGA | GCT | GAC | 1765 |
|---|---|---|---|---|---|---|---|---|---|---|---|---|---|---|---|---|
| Gly | Glu | Trp | Asn | Gly | Met | Val | Lys | Glu | Leu | Ile | Asp | His | Arg | Ala | Asp |  |
|  |  |  |  | 515 |  |  |  |  | 520 |  |  |  |  | 525 |  |  |

| CTG | GCA | GTG | GCC | CCT | CTC | ACC | ATC | ACA | TAC | GTA | CGG | GAG | AAA | GTC | ATT | 1813 |
|---|---|---|---|---|---|---|---|---|---|---|---|---|---|---|---|---|
| Leu | Ala | Val | Ala | Pro | Leu | Thr | Ile | Thr | Tyr | Val | Arg | Glu | Lys | Val | Ile |  |
|  |  | 530 |  |  |  |  |  | 535 |  |  |  |  | 540 |  |  |  |

| GAC | TTC | TCC | AAG | CCC | TTC | ATG | ACC | CTG | GGC | ATT | AGC | ATC | CTT | TAC | CGG | 1861 |
|---|---|---|---|---|---|---|---|---|---|---|---|---|---|---|---|---|
| Asp | Phe | Ser | Lys | Pro | Phe | Met | Thr | Leu | Gly | Ile | Ser | Ile | Leu | Tyr | Arg |  |
|  |  | 545 |  |  |  |  | 550 |  |  |  |  | 555 |  |  |  |  |

| AAG | CCC | AAT | GGA | ACC | AAC | CCG | GGT | GTC | TTC | TCC | TTC | CTC | AAC | CCC | CTA | 1909 |
|---|---|---|---|---|---|---|---|---|---|---|---|---|---|---|---|---|
| Lys | Pro | Asn | Gly | Thr | Asn | Pro | Gly | Val | Phe | Ser | Phe | Leu | Asn | Pro | Leu |  |
| 560 |  |  |  |  | 565 |  |  |  |  | 570 |  |  |  |  |  |  |

| TCT | CCG | GAC | ATT | TGG | ATG | TAC | GTG | CTG | CTC | GCC | TGC | CTA | GGA | GTC | AGT | 1957 |
|---|---|---|---|---|---|---|---|---|---|---|---|---|---|---|---|---|
| Ser | Pro | Asp | Ile | Trp | Met | Tyr | Val | Leu | Leu | Ala | Cys | Leu | Gly | Val | Ser |  |
| 575 |  |  |  |  | 580 |  |  |  |  | 585 |  |  |  |  | 590 |  |

| TGT | GTA | CTG | TTT | GTG | ATT | GCG | AGG | TTC | ACA | CCC | TAC | GAG | TGG | TAT | AAC | 2005 |
|---|---|---|---|---|---|---|---|---|---|---|---|---|---|---|---|---|
| Cys | Val | Leu | Phe | Val | Ile | Ala | Arg | Phe | Thr | Pro | Tyr | Glu | Trp | Tyr | Asn |  |
|  |  |  | 595 |  |  |  |  | 600 |  |  |  |  | 605 |  |  |  |

| CCC | CAC | CCA | TGC | AAC | CCC | GAC | TCA | GAC | GTG | GTG | GAA | AAC | AAT | TTC | ACT | 2053 |
|---|---|---|---|---|---|---|---|---|---|---|---|---|---|---|---|---|
| Pro | His | Pro | Cys | Asn | Pro | Asp | Ser | Asp | Val | Val | Glu | Asn | Asn | Phe | Thr |  |
|  |  | 610 |  |  |  |  | 615 |  |  |  |  | 620 |  |  |  |  |

| TTG | CTA | AAT | AGT | TTC | TGG | TTT | GGA | GTT | GGA | GCT | CTC | ATG | CAG | CAA | GGA | 2101 |
|---|---|---|---|---|---|---|---|---|---|---|---|---|---|---|---|---|
| Leu | Leu | Asn | Ser | Phe | Trp | Phe | Gly | Val | Gly | Ala | Leu | Met | Gln | Gln | Gly |  |
|  |  | 625 |  |  |  |  | 630 |  |  |  |  | 635 |  |  |  |  |

| TCA | GAG | CTG | ATG | CCC | AAG | GCT | CTA | TCG | ACC | AGA | ATA | GTT | GGA | GGA | ATA | 2149 |
|---|---|---|---|---|---|---|---|---|---|---|---|---|---|---|---|---|
| Ser | Glu | Leu | Met | Pro | Lys | Ala | Leu | Ser | Thr | Arg | Ile | Val | Gly | Gly | Ile |  |
| 640 |  |  |  |  | 645 |  |  |  |  | 650 |  |  |  |  |  |  |

| TGG | TGG | TTT | TTC | ACC | CTA | ATC | ATC | ATT | TCA | TCC | TAC | ACG | GCC | AAC | CTG | 2197 |
|---|---|---|---|---|---|---|---|---|---|---|---|---|---|---|---|---|
| Trp | Trp | Phe | Phe | Thr | Leu | Ile | Ile | Ile | Ser | Ser | Tyr | Thr | Ala | Asn | Leu |  |
| 655 |  |  |  |  | 660 |  |  |  |  | 665 |  |  |  |  | 670 |  |

| GCT | GCC | TTC | TTG | ACG | GTA | GAA | AGA | ATG | GAA | TCC | CCC | ATC | GAT | TCC | GCA | 2245 |
|---|---|---|---|---|---|---|---|---|---|---|---|---|---|---|---|---|
| Ala | Ala | Phe | Leu | Thr | Val | Glu | Arg | Met | Glu | Ser | Pro | Ile | Asp | Ser | Ala |  |
|  |  |  |  | 675 |  |  |  |  | 680 |  |  |  |  | 685 |  |  |

| GAC | GAT | CTG | GCC | AAA | CAA | ACC | AAG | ATA | GAA | TAT | GGG | GCA | GTC | AGA | GAT | 2293 |
|---|---|---|---|---|---|---|---|---|---|---|---|---|---|---|---|---|
| Asp | Asp | Leu | Ala | Lys | Gln | Thr | Lys | Ile | Glu | Tyr | Gly | Ala | Val | Arg | Asp |  |
|  |  |  | 690 |  |  |  |  | 695 |  |  |  |  | 700 |  |  |  |

| GGC | TCG | ACG | ATG | ACC | TTC | TTC | AAG | AAA | TCA | AAG | ATC | TCC | ACC | TAT | GAG | 2341 |
|---|---|---|---|---|---|---|---|---|---|---|---|---|---|---|---|---|
| Gly | Ser | Thr | Met | Thr | Phe | Phe | Lys | Lys | Ser | Lys | Ile | Ser | Thr | Tyr | Glu |  |
|  |  | 705 |  |  |  |  | 710 |  |  |  |  | 715 |  |  |  |  |

| AAA | ATG | TGG | GCT | TTC | ATG | AGC | AGT | AGA | CAG | CAG | AGC | GCA | CTG | GTT | AAA | 2389 |
|---|---|---|---|---|---|---|---|---|---|---|---|---|---|---|---|---|
| Lys | Met | Trp | Ala | Phe | Met | Ser | Ser | Arg | Gln | Gln | Ser | Ala | Leu | Val | Lys |  |
| 720 |  |  |  |  | 725 |  |  |  |  | 730 |  |  |  |  |  |  |

| | | | | | | | | | | | | | | | | |
|---|---|---|---|---|---|---|---|---|---|---|---|---|---|---|---|---|
| AAC | AGT | GAC | GAG | GGG | ATC | CAA | AGG | GTG | CTC | ACC | ACC | GAC | TAC | GCA | CTG | 2437 |
| Asn | Ser | Asp | Glu | Gly | Ile | Gln | Arg | Val | Leu | Thr | Thr | Asp | Tyr | Ala | Leu | |
| 735 | | | | 740 | | | | | 745 | | | | | | 750 | |
| CTG | ATG | GAG | TCC | ACC | AGC | ATT | GAG | TAT | GTG | ACG | CAG | AGG | AAC | TGC | AAC | 2485 |
| Leu | Met | Glu | Ser | Thr | Ser | Ile | Glu | Tyr | Val | Thr | Gln | Arg | Asn | Cys | Asn | |
| | | | | 755 | | | | | 760 | | | | | 765 | | |
| CTC | ACT | CAG | ATC | GGG | GGC | CTC | ATA | GAC | TCC | AAA | GGC | TAT | GGA | GTG | GGG | 2533 |
| Leu | Thr | Gln | Ile | Gly | Gly | Leu | Ile | Asp | Ser | Lys | Gly | Tyr | Gly | Val | Gly | |
| | | | 770 | | | | | 775 | | | | | 780 | | | |
| ACG | CCT | ATC | GGC | TCC | CCT | TAC | CGG | GAT | AAA | ATT | ACG | ATT | GCC | ATT | CTT | 2581 |
| Thr | Pro | Ile | Gly | Ser | Pro | Tyr | Arg | Asp | Lys | Ile | Thr | Ile | Ala | Ile | Leu | |
| | | 785 | | | | 790 | | | | | 795 | | | | | |
| CAA | CTG | CAA | GAA | GAA | GGG | AAG | CTT | CAT | ATG | ATG | AAA | GAG | AAG | TGG | TGG | 2629 |
| Gln | Leu | Gln | Glu | Glu | Gly | Lys | Leu | His | Met | Met | Lys | Glu | Lys | Trp | Trp | |
| 800 | | | | | 805 | | | | | 810 | | | | | | |
| AGG | GGG | AAT | GGC | TGC | CCT | GAA | GAA | GAC | AGT | AAG | GAA | GCC | AGT | GCT | CTG | 2677 |
| Arg | Gly | Asn | Gly | Cys | Pro | Glu | Glu | Asp | Ser | Lys | Glu | Ala | Ser | Ala | Leu | |
| 815 | | | | 820 | | | | | 825 | | | | | 830 | | |
| GGA | GTG | GAA | AAT | ATC | GGC | GGC | ATC | TTC | ATT | GTT | CTG | GCT | GCA | GGA | CTC | 2725 |
| Gly | Val | Glu | Asn | Ile | Gly | Gly | Ile | Phe | Ile | Val | Leu | Ala | Ala | Gly | Leu | |
| | | | 835 | | | | | 840 | | | | | 845 | | | |
| GTG | CTT | TCT | GTG | TTT | GTA | GCC | ATT | GGA | GAA | TTT | TTA | TAC | AAA | TCA | CGG | 2773 |
| Val | Leu | Ser | Val | Phe | Val | Ala | Ile | Gly | Glu | Phe | Leu | Tyr | Lys | Ser | Arg | |
| | | | 850 | | | | | 855 | | | | | 860 | | | |
| AAG | AAC | AAT | GAC | GTT | GAG | CAG | TGT | CTC | TCT | TTC | AAT | GCC | ATC | ATG | GAA | 2821 |
| Lys | Asn | Asn | Asp | Val | Glu | Gln | Cys | Leu | Ser | Phe | Asn | Ala | Ile | Met | Glu | |
| | | 865 | | | | 870 | | | | | 875 | | | | | |
| GAG | CTG | GGA | ATA | TCC | CTC | AAG | AAT | CAG | AAA | AAA | TTA | AAG | AAA | AAG | TCA | 2869 |
| Glu | Leu | Gly | Ile | Ser | Leu | Lys | Asn | Gln | Lys | Lys | Leu | Lys | Lys | Lys | Ser | |
| 880 | | | | | 885 | | | | | 890 | | | | | | |
| AGA | ACT | AAG | GGC | AAA | TCT | TCT | TTC | ACA | AGT | ATC | CTT | ACT | TGT | CAC | CAG | 2917 |
| Arg | Thr | Lys | Gly | Lys | Ser | Ser | Phe | Thr | Ser | Ile | Leu | Thr | Cys | His | Gln | |
| 895 | | | | | 900 | | | | | 905 | | | | | 910 | |
| AGA | CGA | ACT | CAG | AGA | AAA | GAG | ACA | GTG | GCG | TGATCAAAGA | | | ACACACCTGT | | | 2967 |
| Arg | Arg | Thr | Gln | Arg | Lys | Glu | Thr | Val | Ala | | | | | | | |
| | | | | 915 | | | | | 920 | | | | | | | |

AAGAAGAAAA AGCCCACACG TCCGCTGCAC ATATTTGGAG GACAGATTTC AGAGGACTAT 3027

GTCTTTATCC ATAACCCCAG TCGTGGACAG AGGGGGAAGA AATGCACAAT TTTTAAAGCT 3087

CACATAGATA TTACTTGAGA AGTGAAACTG ATTCTTTTCA GATGAATTTG TATGCACACT 3147

TATTTTGAAT TTTTCCATTT CCTCCGATAA ATTGCTATGT GTGCTTTCTA AATAATAATA 3207

AACAAGCGGA CTTTGTTTTT CATAAAAAAA AAAAAAAAAA AAA 3250

( 2 ) INFORMATION FOR SEQ ID NO:10:

( i ) SEQUENCE CHARACTERISTICS:
        ( A ) LENGTH: 920 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| | | | | | | | | | | | | | | |
|---|---|---|---|---|---|---|---|---|---|---|---|---|---|---|
| Met | Glu | Arg | Ser | Thr | Val | Leu | Ile | Gln | Pro | Gly | Leu | Trp | Thr | Arg | Asp |
| 1 | | | | 5 | | | | | 10 | | | | | 15 | |
| Thr | Ser | Trp | Thr | Leu | Leu | Tyr | Phe | Leu | Cys | Tyr | Ile | Leu | Pro | Gln | Thr |
| | | | 20 | | | | | 25 | | | | | 30 | | |
| Ser | Pro | Gln | Val | Leu | Arg | Ile | Gly | Gly | Ile | Phe | Glu | Thr | Val | Glu | Asn |
| | | | 35 | | | | 40 | | | | | 45 | | | |
| Glu | Pro | Val | Asn | Val | Glu | Glu | Leu | Ala | Phe | Lys | Phe | Ala | Val | Thr | Ser |
| | | 50 | | | | | 55 | | | | | 60 | | | |

```
Ile Asn Arg Asn Arg Thr Leu Met Pro Asn Thr Thr Leu Thr Tyr Asp
 65              70              75              80
Ile Gln Arg Ile Asn Leu Phe Asp Ser Phe Glu Ala Ser Arg Arg Ala
             85              90                   95
Cys Asp Gln Leu Ala Leu Gly Val Ala Ala Leu Phe Gly Pro Ser His
            100             105            110
Ser Ser Ser Val Ser Ala Val Gln Ser Ile Cys Asn Ala Leu Glu Val
        115             120             125
Pro His Ile Gln Thr Arg Trp Lys His Pro Ser Val Asp Ser Arg Asp
    130             135             140
Leu Phe Tyr Ile Asn Leu Tyr Pro Asp Tyr Ala Ala Ile Ser Arg Ala
145             150             155                         160
Val Leu Asp Leu Val Leu Tyr Tyr Asn Trp Lys Thr Val Thr Val Val
                165             170             175
Tyr Glu Asp Ser Thr Gly Leu Ile Arg Leu Gln Glu Leu Ile Lys Ala
            180             185             190
Pro Ser Arg Tyr Asn Ile Lys Ile Lys Ile Arg Gln Leu Pro Pro Ala
        195             200             205
Asn Lys Asp Ala Lys Pro Leu Leu Lys Glu Met Lys Lys Ser Lys Glu
    210             215             220
Phe Tyr Val Ile Phe Asp Cys Ser His Glu Thr Ala Ala Glu Ile Leu
225             230             235                         240
Lys Gln Ile Leu Phe Met Gly Met Met Thr Glu Tyr Tyr His Tyr Phe
                245             250             255
Phe Thr Thr Leu Asp Leu Phe Ala Leu Asp Leu Glu Leu Tyr Arg Tyr
            260             265             270
Ser Gly Val Asn Met Thr Gly Phe Arg Leu Leu Asn Ile Asp Asn Pro
        275             280             285
His Val Ser Ser Ile Ile Glu Lys Trp Ser Met Glu Arg Leu Gln Ala
    290             295             300
Pro Pro Arg Pro Glu Thr Gly Leu Leu Asp Gly Met Met Thr Thr Glu
305             310             315                         320
Ala Ala Leu Met Tyr Asp Ala Val Tyr Met Val Ala Ile Ala Ser His
                325             330             335
Arg Ala Ser Gln Leu Thr Val Ser Ser Leu Gln Cys His Arg His Lys
            340             345             350
Pro Trp Arg Leu Gly Pro Arg Phe Met Asn Leu Ile Lys Glu Ala Arg
        355             360             365
Trp Asp Gly Leu Thr Gly Arg Ile Thr Phe Asn Lys Thr Asp Gly Leu
    370             375             380
Arg Lys Asp Phe Asp Leu Asp Ile Ile Ser Leu Lys Glu Glu Gly Thr
385             390             395                         400
Glu Lys Ala Ser Gly Glu Val Ser Lys His Leu Tyr Lys Val Trp Lys
                405             410             415
Lys Ile Gly Ile Trp Asn Ser Asn Ser Gly Leu Asn Met Thr Asp Gly
            420             425             430
Asn Arg Asp Arg Ser Asn Asn Ile Thr Asp Ser Leu Ala Asn Arg Thr
        435             440             445
Leu Ile Val Thr Thr Ile Leu Glu Glu Pro Tyr Val Met Tyr Arg Lys
    450             455             460
Ser Asp Lys Pro Leu Tyr Gly Asn Asp Arg Phe Glu Gly Tyr Cys Leu
465             470             475                         480
Asp Leu Leu Lys Glu Leu Ser Asn Ile Leu Gly Phe Leu Tyr Asp Val
                485             490             495
```

-continued

| | | | | | | | | | | | | | |
|---|---|---|---|---|---|---|---|---|---|---|---|---|---|
| Lys | Leu | Val | Pro 500 | Asp | Gly | Lys | Tyr 505 | Gly | Ala | Gln | Asn | Asp | Lys 510 | Gly | Glu |
| Trp | Asn | Gly 515 | Met | Val | Lys | Glu | Leu 520 | Ile | Asp | His | Arg | Ala 525 | Asp | Leu | Ala |
| Val | Ala 530 | Pro | Leu | Thr | Ile | Thr 535 | Tyr | Val | Arg | Glu | Lys 540 | Val | Ile | Asp | Phe |
| Ser 545 | Lys | Pro | Phe | Met | Thr 550 | Leu | Gly | Ile | Ser | Ile 555 | Leu | Tyr | Arg | Lys | Pro 560 |
| Asn | Gly | Thr | Asn | Pro 565 | Gly | Val | Phe | Ser | Phe 570 | Leu | Asn | Pro | Leu | Ser 575 | Pro |
| Asp | Ile | Trp | Met 580 | Tyr | Val | Leu | Leu | Ala 585 | Cys | Leu | Gly | Val | Ser 590 | Cys | Val |
| Leu | Phe | Val 595 | Ile | Ala | Arg | Phe | Thr 600 | Pro | Tyr | Glu | Trp | Tyr 605 | Asn | Pro | His |
| Pro | Cys 610 | Asn | Pro | Asp | Ser | Asp 615 | Val | Val | Glu | Asn | Asn 620 | Phe | Thr | Leu | Leu |
| Asn 625 | Ser | Phe | Trp | Phe | Gly 630 | Val | Gly | Ala | Leu | Met 635 | Gln | Gln | Gly | Ser | Glu 640 |
| Leu | Met | Pro | Lys | Ala 645 | Leu | Ser | Thr | Arg | Ile 650 | Val | Gly | Gly | Ile | Trp 655 | Trp |
| Phe | Phe | Thr | Leu 660 | Ile | Ile | Ile | Ser | Ser 665 | Tyr | Thr | Ala | Asn | Leu 670 | Ala | Ala |
| Phe | Leu | Thr 675 | Val | Glu | Arg | Met | Glu 680 | Ser | Pro | Ile | Asp | Ser 685 | Ala | Asp | Asp |
| Leu | Ala 690 | Lys | Gln | Thr | Lys | Ile 695 | Glu | Tyr | Gly | Ala | Val 700 | Arg | Asp | Gly | Ser |
| Thr 705 | Met | Thr | Phe | Phe | Lys 710 | Lys | Ser | Lys | Ile | Ser 715 | Thr | Tyr | Glu | Lys | Met 720 |
| Trp | Ala | Phe | Met | Ser 725 | Ser | Arg | Gln | Gln | Ser 730 | Ala | Leu | Val | Lys | Asn 735 | Ser |
| Asp | Glu | Gly | Ile 740 | Gln | Arg | Val | Leu | Thr 745 | Thr | Asp | Tyr | Ala | Leu 750 | Leu | Met |
| Glu | Ser | Thr 755 | Ser | Ile | Glu | Tyr | Val 760 | Thr | Gln | Arg | Asn | Cys 765 | Asn | Leu | Thr |
| Gln | Ile 770 | Gly | Gly | Leu | Ile | Asp 775 | Ser | Lys | Gly | Tyr | Gly 780 | Val | Gly | Thr | Pro |
| Ile 785 | Gly | Ser | Pro | Tyr | Arg 790 | Asp | Lys | Ile | Thr | Ile 795 | Ala | Ile | Leu | Gln | Leu 800 |
| Gln | Glu | Glu | Gly | Lys 805 | Leu | His | Met | Met | Lys 810 | Glu | Lys | Trp | Trp | Arg 815 | Gly |
| Asn | Gly | Cys | Pro 820 | Glu | Glu | Asp | Ser | Lys 825 | Glu | Ala | Ser | Ala | Leu 830 | Gly | Val |
| Glu | Asn | Ile 835 | Gly | Gly | Ile | Phe | Ile 840 | Val | Leu | Ala | Ala | Gly 845 | Leu | Val | Leu |
| Ser | Val 850 | Phe | Val | Ala | Ile | Gly 855 | Glu | Phe | Leu | Tyr | Lys 860 | Ser | Arg | Lys | Asn |
| Asn 865 | Asp | Val | Glu | Gln | Cys 870 | Leu | Ser | Phe | Asn | Ala 875 | Ile | Met | Glu | Glu | Leu 880 |
| Gly | Ile | Ser | Leu | Lys 885 | Asn | Gln | Lys | Lys | Leu 890 | Lys | Lys | Ser | Arg 895 | Thr |
| Lys | Gly | Lys | Ser 900 | Ser | Phe | Thr | Ser | Ile 905 | Leu | Thr | Cys | His | Gln 910 | Arg | Arg |
| Thr | Gln | Arg 915 | Lys | Glu | Thr | Val | Ala 920 | | | | | | | | |

(2) INFORMATION FOR SEQ ID NO:11:

(i) SEQUENCE CHARACTERISTICS:
        (A) LENGTH: 4608 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: GluR6

(ix) FEATURE:
        (A) NAME/KEY: CDS
        (B) LOCATION: 307..2961

(xi) SEQUENCE DESCRIPTION: SEQ ID NO:11:

```
GAATTCGGGC TCGCAAGGGC TTCGCAGGCT GGACATTGTG CTTGCTGGAT TTTTCCCGGA      60

TGCTCCCGGA CTAACATGGA TGTCCCACCA TCCCTTGCAG TGGAAGCTTG CTCCTTGGCG     120

CAGTGAGAGT GAAGAACATG CAGCGACTGC TAATGGGTTT GGGAAGCGGA GACTCCTTCC     180

TCTTTCTGTG ACCATGCCGT GATTGTGTCT GCGGCCACTA CTCCACGCAT CTTCCTTCTC     240

GTCCAAGCCC GGAGCCTAAC GCTAGATCGG GGAAGTGGGT GCCGCGCGCG CAGGCACGGA     300

AACATC ATG AAG ATT ATT TCC CCA GTT TTA AGT AAT CTA GTC TTC AGT        348
       Met Lys Ile Ile Ser Pro Val Leu Ser Asn Leu Val Phe Ser
        1               5                   10

CGC TCC ATT AAA GTC CTG CTC TGC TTA TTG TGG ATC GGA TAT TCG CAA       396
Arg Ser Ile Lys Val Leu Leu Cys Leu Leu Trp Ile Gly Tyr Ser Gln
 15              20                  25                  30

GGA ACC ACA CAT GTG TTA AGA TTC GGT GGT ATA TTT GAA TAT GTG GAA       444
Gly Thr Thr His Val Leu Arg Phe Gly Gly Ile Phe Glu Tyr Val Glu
             35                  40                  45

TCT GGC CCC ATG GGA GCA GAA GAA CTT GCA TTC AGA TTT GCT GTG AAT       492
Ser Gly Pro Met Gly Ala Glu Glu Leu Ala Phe Arg Phe Ala Val Asn
             50                  55                  60

ACC ATC AAC AGA AAC AGG ACT TTG CTG CCC AAC ACC ACT TTA ACT TAT       540
Thr Ile Asn Arg Asn Arg Thr Leu Leu Pro Asn Thr Thr Leu Thr Tyr
         65                  70                  75

GAT ACT CAG AAG ATC AAT CTC TAT GAC AGT TTT GAA GCA TCT AAG AAA       588
Asp Thr Gln Lys Ile Asn Leu Tyr Asp Ser Phe Glu Ala Ser Lys Lys
     80                  85                  90

GCT TGT GAT CAG CTG TCT CTT GGG GTG GCT GCT ATC TTC GGT CCT TCA       636
Ala Cys Asp Gln Leu Ser Leu Gly Val Ala Ala Ile Phe Gly Pro Ser
 95                 100                 105                 110

CAC AGT TCA TCA GCC AAT GCT GTG CAG TCC ATC TGC AAT GCT CTG GGG       684
His Ser Ser Ser Ala Asn Ala Val Gln Ser Ile Cys Asn Ala Leu Gly
                115                 120                 125

GTT CCC CAC ATA CAG ACC CGC TGG AAG CAC CAG GTG TCA GAC AAC AAG       732
Val Pro His Ile Gln Thr Arg Trp Lys His Gln Val Ser Asp Asn Lys
            130                 135                 140

GAT TCC TTC TAC GTC AGT CTC TAC CCA GAC TTC TCT TCC CTG AGC CGC       780
Asp Ser Phe Tyr Val Ser Leu Tyr Pro Asp Phe Ser Ser Leu Ser Arg
        145                 150                 155

GCC ATC TTG GAT TTG GTG CAG TTT TTT AAG TGG AAA ACT GTC ACA GTT       828
Ala Ile Leu Asp Leu Val Gln Phe Phe Lys Trp Lys Thr Val Thr Val
        160                 165                 170

GTG TAT GAC GAC AGC ACT GGT CTC ATT CGC TTG CAA GAG CTC ATC AAA       876
Val Tyr Asp Asp Ser Thr Gly Leu Ile Arg Leu Gln Glu Leu Ile Lys
175                 180                 185                 190

GCT CCA TCG AGG TAC AAT CTT CGA CTT AAA ATT CGT CAG CTG CCA GCT       924
Ala Pro Ser Arg Tyr Asn Leu Arg Leu Lys Ile Arg Gln Leu Pro Ala
                195                 200                 205

GAT ACC AAA GAT GCA AAA CCT TTG CTG AAG GAG ATG AAA AGA GGC AAG       972
```

```
Asp Thr Lys Asp Ala Lys Pro Leu Leu Lys Glu Met Lys Arg Gly Lys
        210             215             220

GAG TTC CAC GTG ATC TTC GAC TGC AGC CAT GAG ATG GCA GCA GGC ATT    1020
Glu Phe His Val Ile Phe Asp Cys Ser His Glu Met Ala Ala Gly Ile
        225             230             235

TTA AAA CAG GCA TTA GCT ATG GGA ATG ATG ACA GAA TAC TAT CAC TAT    1068
Leu Lys Gln Ala Leu Ala Met Gly Met Met Thr Glu Tyr Tyr His Tyr
        240             245             250

ATA TTT ACA ACT CTG GAC CTC TTT GCT CTT GAC GTG GAG CCC TAC AGA    1116
Ile Phe Thr Thr Leu Asp Leu Phe Ala Leu Asp Val Glu Pro Tyr Arg
255             260             265             270

TAC AGT GGC GTA AAT ATG ACA GGG TTC AGG ATA CTA AAT ACA GAG AAT    1164
Tyr Ser Gly Val Asn Met Thr Gly Phe Arg Ile Leu Asn Thr Glu Asn
                275             280             285

ACC CAA GTC TCC TCC ATC ATC GAA AAG TGG TCT ATG GAA CGG TTA CAG    1212
Thr Gln Val Ser Ser Ile Ile Glu Lys Trp Ser Met Glu Arg Leu Gln
            290             295             300

GCG CCT CCA AAA CCT GAC TCA GGT TTG CTG GAT GGA TTT ATG ACG ACT    1260
Ala Pro Pro Lys Pro Asp Ser Gly Leu Leu Asp Gly Phe Met Thr Thr
        305             310             315

GAT GCT GCT CTG ATG TAT GAT GCA GTG CAC GTT GTG TCT GTG GCT GTC    1308
Asp Ala Ala Leu Met Tyr Asp Ala Val His Val Val Ser Val Ala Val
        320             325             330

CAA CAG TTT CCC CAG ATG ACA GTC AGC TCC TTG CAA TGC AAT CGA CAC    1356
Gln Gln Phe Pro Gln Met Thr Val Ser Ser Leu Gln Cys Asn Arg His
335             340             345             350

AAA CCC TGG CGC TTT GGG ACC CGC TTC ATG AGT CTA ATT AAA GAG GCT    1404
Lys Pro Trp Arg Phe Gly Thr Arg Phe Met Ser Leu Ile Lys Glu Ala
            355             360             365

CAC TGG GAA GGT CTC ACA GGC AGA ATA ACA TTT AAC AAA ACC AAT GGA    1452
His Trp Glu Gly Leu Thr Gly Arg Ile Thr Phe Asn Lys Thr Asn Gly
            370             375             380

TTA CGG ACA GAT TTT GAT TTG GAT GTG ATC AGT CTC AAG GAA GAA GGT    1500
Leu Arg Thr Asp Phe Asp Leu Asp Val Ile Ser Leu Lys Glu Glu Gly
        385             390             395

CTG GAG AAG ATT GGA ACT TGG GAT CCA GCC AGT GGC CTG AAT ATG ACA    1548
Leu Glu Lys Ile Gly Thr Trp Asp Pro Ala Ser Gly Leu Asn Met Thr
    400             405             410

GAA AGT CAG AAA GGA AAG CCA GCA AAT ATC ACA GAC TCA TTG TCT AAT    1596
Glu Ser Gln Lys Gly Lys Pro Ala Asn Ile Thr Asp Ser Leu Ser Asn
415             420             425             430

CGT TCT TTG ATT GTT ACC ACC ATT TTG GAA GAA CCG TAT GTT CTG TTT    1644
Arg Ser Leu Ile Val Thr Thr Ile Leu Glu Glu Pro Tyr Val Leu Phe
            435             440             445

AAG AAG TCT GAC AAA CCA CTC TAT GGG AAT GAT CGA TTT GAA GGC TAC    1692
Lys Lys Ser Asp Lys Pro Leu Tyr Gly Asn Asp Arg Phe Glu Gly Tyr
        450             455             460

TGT ATT GAT CTC CTA CGA GAG TTA TCT ACA ATC CTT GGC TTT ACA TAT    1740
Cys Ile Asp Leu Leu Arg Glu Leu Ser Thr Ile Leu Gly Phe Thr Tyr
        465             470             475

GAG ATT AGG CTT GTG GAG GAT GGG AAA TAT GGA GCC CAG GAT GAT GTG    1788
Glu Ile Arg Leu Val Glu Asp Gly Lys Tyr Gly Ala Gln Asp Asp Val
        480             485             490

AAC GGA CAA TGG AAT GGA ATG GTT CGT GAA CTA ATC GAT CAT AAA GCT    1836
Asn Gly Gln Trp Asn Gly Met Val Arg Glu Leu Ile Asp His Lys Ala
495             500             505             510

GAC CTT GCA GTT GCT CCA CTG GCT ATA ACC TAT GTT CGT GAG AAG GTC    1884
Asp Leu Ala Val Ala Pro Leu Ala Ile Thr Tyr Val Arg Glu Lys Val
            515             520             525

ATC GAC TTT TCA AAG CCG TTT ATG ACA CTT GGA ATA AGT ATT TTG TAC    1932
Ile Asp Phe Ser Lys Pro Phe Met Thr Leu Gly Ile Ser Ile Leu Tyr
        530             535             540
```

| | | | | | | | | | | | | | | | | |
|---|---|---|---|---|---|---|---|---|---|---|---|---|---|---|---|---|
| CGC | AAG | CCC | AAT | GGT | ACA | AAC | CCA | GGC | GTC | TTC | TCC | TTC | CTG | AAT | CCT | 1980 |
| Arg | Lys | Pro 545 | Asn | Gly | Thr | Asn | Pro 550 | Gly | Val | Phe | Ser 555 | Phe | Leu | Asn | Pro | |
| CTC | TCC | CCT | GAT | ATC | TGG | ATG | TAT | GTT | CTG | CTG | GCT | TGC | TTG | GGT | GTC | 2028 |
| Leu | Ser 560 | Pro | Asp | Ile | Trp | Met 565 | Tyr | Val | Leu | Leu | Ala 570 | Cys | Leu | Gly | Val | |
| AGT | TGT | GTG | CTC | TTT | GTC | ATA | GCC | AGG | TTT | AGT | CCC | TAT | GAG | TGG | TAT | 2076 |
| Ser 575 | Cys | Val | Leu | Phe | Val 580 | Ile | Ala | Arg | Phe | Ser 585 | Pro | Tyr | Glu | Trp | Tyr 590 | |
| AAC | CCA | CAC | CCT | TGC | AAC | CCT | GAC | TCA | GAC | GTG | GTG | GAA | AAC | AAT | TTT | 2124 |
| Asn | Pro | His | Pro | Cys 595 | Asn | Pro | Asp | Ser | Asp 600 | Val | Val | Glu | Asn | Asn 605 | Phe | |
| ACC | TTG | CTA | AAT | AGT | TTC | TGG | TTT | GGA | GTT | GGA | GCT | CTC | ATG | CGG | CAA | 2172 |
| Thr | Leu | Leu | Asn 610 | Ser | Phe | Trp | Phe | Gly 615 | Val | Gly | Ala | Leu | Met 620 | Arg | Gln | |
| GGT | TCT | GAG | CTC | ATG | CCC | AAA | GCA | CTC | TCC | ACC | AGG | ATA | GTG | GGA | GGC | 2220 |
| Gly | Ser | Glu 625 | Leu | Met | Pro | Lys | Ala 630 | Leu | Ser | Thr | Arg | Ile 635 | Val | Gly | Gly | |
| ATT | TGG | TGG | TTT | TTC | ACA | CTT | ATC | ATC | ATT | TCT | TCG | TAT | ACC | GCT | AAC | 2268 |
| Ile | Trp | Trp 640 | Phe | Phe | Thr | Leu | Ile 645 | Ile | Ile | Ser | Ser | Tyr 650 | Thr | Ala | Asn | |
| CTA | GCC | GCC | TTT | CTG | ACT | GTG | GAA | CGC | ATG | GAG | TCG | CCC | ATT | GAC | TCT | 2316 |
| Leu 655 | Ala | Ala | Phe | Leu | Thr 660 | Val | Glu | Arg | Met | Glu 665 | Ser | Pro | Ile | Asp | Ser 670 | |
| GCT | GAC | GAT | TTA | GCT | AAG | CAA | ACC | AAG | ATA | GAG | TAT | GGA | GCA | GTG | GAG | 2364 |
| Ala | Asp | Asp | Leu | Ala 675 | Lys | Gln | Thr | Lys | Ile 680 | Glu | Tyr | Gly | Ala | Val 685 | Glu | |
| GAC | GGC | GCA | ACC | ATG | ACG | TTT | TTT | AAG | AAA | TCA | AAA | ATT | TCA | ACG | TAT | 2412 |
| Asp | Gly | Ala | Thr 690 | Met | Thr | Phe | Phe | Lys 695 | Lys | Ser | Lys | Ile | Ser 700 | Thr | Tyr | |
| GAT | AAA | ATG | TGG | GCG | TTT | ATG | AGC | AGC | AGG | AGA | CAG | TCT | GTG | CTT | GTC | 2460 |
| Asp | Lys | Met 705 | Trp | Ala | Phe | Met | Ser 710 | Ser | Arg | Arg | Gln | Ser 715 | Val | Leu | Val | |
| AAA | AGC | AAT | GAG | GAA | GGG | ATC | CAA | CGA | GTC | CTC | ACC | TCG | GAT | TAT | GCT | 2508 |
| Lys | Ser | Asn 720 | Glu | Glu | Gly | Ile | Gln 725 | Arg | Val | Leu | Thr 730 | Ser | Asp | Tyr | Ala | |
| TTC | TTA | ATG | GAG | TCA | ACA | ACC | ATC | GAG | TTT | GTT | ACA | CAG | CGG | AAC | TGT | 2556 |
| Phe 735 | Leu | Met | Glu | Ser | Thr 740 | Thr | Ile | Glu | Phe | Val 745 | Thr | Gln | Arg | Asn | Cys 750 | |
| AAC | CTC | ACG | CAG | ATT | GGC | GGC | CTT | ATA | GAC | TCC | AAA | GGC | TAT | GGC | GTT | 2604 |
| Asn | Leu | Thr | Gln | Ile 755 | Gly | Gly | Leu | Ile | Asp 760 | Ser | Lys | Gly | Tyr | Gly 765 | Val | |
| GGC | ACT | CCT | ATG | GGC | TCT | CCA | TAT | CGA | GAC | AAA | ATC | ACC | ATA | GCA | ATT | 2652 |
| Gly | Thr | Pro | Met 770 | Gly | Ser | Pro | Tyr | Arg 775 | Asp | Lys | Ile | Thr | Ile 780 | Ala | Ile | |
| CTT | CAG | CTG | CAG | GAG | GAA | GGC | AAG | CTG | CAC | ATG | ATG | AAG | GAG | AAA | TGG | 2700 |
| Leu | Gln | Leu 785 | Gln | Glu | Glu | Gly | Lys 790 | Leu | His | Met | Met | Lys 795 | Glu | Lys | Trp | |
| TGG | CGG | GGC | AAT | GGC | TGC | CCA | GAG | GAG | GAG | AGC | AAA | GAG | GCC | AGT | GCT | 2748 |
| Trp | Arg 800 | Gly | Asn | Gly | Cys | Pro 805 | Glu | Glu | Glu | Ser | Lys 810 | Glu | Ala | Ser | Ala | |
| CTG | GGG | GTG | CAG | AAT | ATT | GGT | GGT | ATC | TTC | ATT | GTC | CTG | GCA | GCC | GGC | 2796 |
| Leu 815 | Gly | Val | Gln | Asn | Ile 820 | Gly | Gly | Ile | Phe | Ile 825 | Val | Leu | Ala | Ala | Gly 830 | |
| TTG | GTG | CTC | TCA | GTT | TTT | GTG | GCA | GTG | GGA | GAG | TTT | TTA | TAC | AAA | TCC | 2844 |
| Leu | Val | Leu | Ser | Val 835 | Phe | Val | Ala | Val | Gly 840 | Glu | Phe | Leu | Tyr | Lys 845 | Ser | |
| AAA | AAA | AAC | GCT | CAA | TTG | GAA | AAG | AGG | TCC | TTC | TGT | AGC | GCT | ATG | GTG | 2892 |
| Lys | Lys | Asn | Ala 850 | Gln | Leu | Glu | Lys | Arg 855 | Ser | Phe | Cys | Ser | Ala 860 | Met | Val | |
| GAA | GAG | CTG | AGA | ATG | TCC | CTG | AAG | TGC | CAG | CGT | CGG | CTC | AAA | CAT | AAG | 2940 |

```
Glu Glu Leu Arg Met Ser Leu Lys Cys Gln Arg Arg Leu Lys His Lys
        865             870             875

CCA CAG CCC CAG TTA TTG TGAAAACAGA AGAAGTTATC AACATGCACA          2988
Pro Gln Pro Gln Leu Leu
        880             885

CATTTAACGA CAGAAGGTTG CCAGGTAAAG AAACCATGGC ATGAAGCTGG GAGGCCAATC  3048

ACCCAAGCAC AAACTGTCGT CTTTTTTTTT TTTTTTTCCA AACAATTTAG CGAGAATGTT  3108

TCCTGTGGAA ATATGCAACC TGTGCAAAAT AAAATGAGTT ACCTCATGCC GCTGTGTCTA  3168

TGAACTAGAG ACTCTGTGAT CTAAGCAGTT TCAGTGATCA GACTTGATTT ACAAGCACCG  3228

TGGATCAACC AAGTTACACG GGGTTACACT GTTTATCATA GGTTCCTCCC TTCCTTTGAG  3288

TGAATGTTAC ATGCAAATGT TGTGGCTGGT TTCAAATGCA GTCCAGGGAG AAACTGCTGG  3348

TTCCTTCTGA AGCTCAGCTG TCGTCAGGAG ATGGAATGCC GGTGCCCAAA AGGGTAACCA  3408

ATAAAAATGC CATAAAAATT TTAAAAAAAT GCGTGAGATC GGCAAAAATT ATAGTGTTAC  3468

AAGAAACAGT ACAGTCCCAT GGTCACCAAC ACAATAGAGG TGATAATGTT ACTAGCCCCC  3528

AATACTCAGT AAAATCGTCA TCTGAATAGA TAATATGTGT TCATAGAATG TGAAAAAAAA  3588

TGTAATGCGA GACACACCAG TATCAATAGA AGTGGAACTG AAGGCAGAAC ATCATCAGTT  3648

ACTTTCTTT TTCAATAGTC TGTGTCATGG ATTGTGATAT AGATGGCAAT TATCAAGCCA   3708

ATAATTTTTT TTCTGAAAAT ACCTATGGCA AATATTTTAA TAGGCAACTT GCTCCCACAA  3768

ATCCCTACTC TAACCTCCCC CAGAAATATA AAAGGAACCA TTGGTTTAGA GATTGGTATG  3828

TAAGAGATGA TGTTTTGCAA GCCTTGTCGT GCATTGTAAA AGGGCTCAGT GTTACTGGTT  3888

ACAGGGAAGA CTGAAGCTTT CACCCTGACA TTCTGAAATG TCAACCGAAA CTCTCCTTCC  3948

TCCTGTAAAG GACCTTGATG GGGCAGATTC CATTGATCAA AGAATGGGGA CTTGTCACCT  4008

ATACAATGGT ACGTGACAGA ACTTTGAGGT GGACTGCATT TAATAATAGT CACAATGTTA  4068

AAAGAACAAA ATTCTTGAGC AGTTTTTTTT TTTGTTTTG TTTTGTTTTC AAAAAATGTT   4128

CAGGTTTATT TGTGGAAATG CAAGATTTCT ATAAATAGT TTTTGTATGG AAATTTTTGT   4188

AATACTTTTT ATCAACAAAA TAAGAACACA TGTTTCTGTC AGGGGTGTGA GGTCAAGCAT  4248

GAACGGTAGT GCGTGTGCAC CACCAACGTT TGGTGAAACT ATTTTATCA AGAAAAAGGA   4308

ATCATAGAAG AGAAATATTT TCAAGTTAGA TACTATAAAA GCTAGGTGCA CTACCACCAC  4368

GGCTTGTCGC GCCACACCCC TGAGTCCACA AGGTGGATAA CATATTGTAA TGAACAGTTG  4428

TGTGTAAAAT GGCAAAAGAC ACAGACCTCT TGACAACATT GTGAAAACAG TTGAGTGCAC  4488

ACAGTTTGCT GTTTGAATCC AATGCACAAA AATTTTACAA AAATCCATTA AAATTATGTC  4548

CGTTTTAAAA CCTGCAGCCC GGGGGATCCA CTAGTTCTAG AGCCGGTGCC CAATTCGCCC  4608
```

( 2 ) INFORMATION FOR SEQ ID NO:12:

( i ) SEQUENCE CHARACTERISTICS:
        ( A ) LENGTH: 884 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Met Lys Ile Ile Ser Pro Val Leu Ser Asn Leu Val Phe Ser Arg Ser
 1               5                  10                  15

Ile Lys Val Leu Leu Cys Leu Leu Trp Ile Gly Tyr Ser Gln Gly Thr
            20                  25                  30

Thr His Val Leu Arg Phe Gly Gly Ile Phe Glu Tyr Val Glu Ser Gly
        35                  40                  45
```

| | | | | | | | | | | | | | | |
|---|---|---|---|---|---|---|---|---|---|---|---|---|---|---|
|Pro|Met|Gly|Ala|Glu|Glu|Leu|Ala|Phe|Arg|Phe|Ala|Val|Asn|Thr|Ile|
| |50| | | | |55| | | |60| | | | |
|Asn|Arg|Asn|Arg|Thr|Leu|Leu|Pro|Asn|Thr|Thr|Leu|Thr|Tyr|Asp|Thr|
|65| | | | |70| | | |75| | | | | |80|
|Gln|Lys|Ile|Asn|Leu|Tyr|Asp|Ser|Phe|Glu|Ala|Ser|Lys|Lys|Ala|Cys|
| | | | |85| | | |90| | | | |95| | |
|Asp|Gln|Leu|Ser|Leu|Gly|Val|Ala|Ala|Ile|Phe|Gly|Pro|Ser|His|Ser|
| | | |100| | | |105| | | |110| | | | |
|Ser|Ser|Ala|Asn|Ala|Val|Gln|Ser|Ile|Cys|Asn|Ala|Leu|Gly|Val|Pro|
| | |115| | | |120| | | |125| | | | | |
|His|Ile|Gln|Thr|Arg|Trp|Lys|His|Gln|Val|Ser|Asp|Asn|Lys|Asp|Ser|
| |130| | | |135| | | |140| | | | | | |
|Phe|Tyr|Val|Ser|Leu|Tyr|Pro|Asp|Phe|Ser|Ser|Leu|Ser|Arg|Ala|Ile|
|145| | | |150| | | |155| | | | | | |160|
|Leu|Asp|Leu|Val|Gln|Phe|Phe|Lys|Trp|Lys|Thr|Val|Thr|Val|Val|Tyr|
| | | | |165| | | |170| | | | |175| | |
|Asp|Asp|Ser|Thr|Gly|Leu|Ile|Arg|Leu|Gln|Glu|Leu|Ile|Lys|Ala|Pro|
| | | |180| | | |185| | | |190| | | | |
|Ser|Arg|Tyr|Asn|Leu|Arg|Leu|Lys|Ile|Arg|Gln|Leu|Pro|Ala|Asp|Thr|
| | |195| | | |200| | | |205| | | | | |
|Lys|Asp|Ala|Lys|Pro|Leu|Leu|Lys|Glu|Met|Lys|Arg|Gly|Lys|Glu|Phe|
| |210| | | |215| | | |220| | | | | | |
|His|Val|Ile|Phe|Asp|Cys|Ser|His|Glu|Met|Ala|Ala|Gly|Ile|Leu|Lys|
|225| | | |230| | | |235| | | | | | |240|
|Gln|Ala|Leu|Ala|Met|Gly|Met|Met|Thr|Glu|Tyr|Tyr|His|Tyr|Ile|Phe|
| | | |245| | | |250| | | |255| | | | |
|Thr|Thr|Leu|Asp|Leu|Phe|Ala|Leu|Asp|Val|Glu|Pro|Tyr|Arg|Tyr|Ser|
| | |260| | | |265| | | |270| | | | | |
|Gly|Val|Asn|Met|Thr|Gly|Phe|Arg|Ile|Leu|Asn|Thr|Glu|Asn|Thr|Gln|
| |275| | | |280| | | |285| | | | | | |
|Val|Ser|Ser|Ile|Ile|Glu|Lys|Trp|Ser|Met|Glu|Arg|Leu|Gln|Ala|Pro|
|290| | | |295| | | |300| | | | | | | |
|Pro|Lys|Pro|Asp|Ser|Gly|Leu|Leu|Asp|Gly|Phe|Met|Thr|Thr|Asp|Ala|
|305| | | |310| | | |315| | | | | | |320|
|Ala|Leu|Met|Tyr|Asp|Ala|Val|His|Val|Val|Ser|Val|Ala|Val|Gln|Gln|
| | | |325| | | |330| | | |335| | | | |
|Phe|Pro|Gln|Met|Thr|Val|Ser|Ser|Leu|Gln|Cys|Asn|Arg|His|Lys|Pro|
| | |340| | | |345| | | |350| | | | | |
|Trp|Arg|Phe|Gly|Thr|Arg|Phe|Met|Ser|Leu|Ile|Lys|Glu|Ala|His|Trp|
| |355| | | |360| | | |365| | | | | | |
|Glu|Gly|Leu|Thr|Gly|Arg|Ile|Thr|Phe|Asn|Lys|Thr|Asn|Gly|Leu|Arg|
|370| | | |375| | | |380| | | | | | | |
|Thr|Asp|Phe|Asp|Leu|Asp|Val|Ile|Ser|Leu|Lys|Glu|Glu|Gly|Leu|Glu|
|385| | | |390| | | |395| | | | | | |400|
|Lys|Ile|Gly|Thr|Trp|Asp|Pro|Ala|Ser|Gly|Leu|Asn|Met|Thr|Glu|Ser|
| | | |405| | | |410| | | |415| | | | |
|Gln|Lys|Gly|Lys|Pro|Ala|Asn|Ile|Thr|Asp|Ser|Leu|Ser|Asn|Arg|Ser|
| | |420| | | |425| | | |430| | | | | |
|Leu|Ile|Val|Thr|Thr|Ile|Leu|Glu|Glu|Pro|Tyr|Val|Leu|Phe|Lys|Lys|
| | |435| | | |440| | | |445| | | | | |
|Ser|Asp|Lys|Pro|Leu|Tyr|Gly|Asn|Asp|Arg|Phe|Glu|Gly|Tyr|Cys|Ile|
| |450| | | |455| | | |460| | | | | | |
|Asp|Leu|Leu|Arg|Glu|Leu|Ser|Thr|Ile|Leu|Gly|Phe|Thr|Tyr|Glu|Ile|
|465| | | |470| | | |475| | | | | | |480|
|Arg|Leu|Val|Glu|Asp|Gly|Lys|Tyr|Gly|Ala|Gln|Asp|Asp|Val|Asn|Gly|

|     |     |     |     |     |     |     |     |     |     |     |     |     |     |     |
|-----|-----|-----|-----|-----|-----|-----|-----|-----|-----|-----|-----|-----|-----|-----|
|     |     |     |     | 485 |     |     |     |     | 490 |     |     |     |     | 495 |
| Gln | Trp | Asn | Gly | Met | Val | Arg | Glu | Leu | Ile | Asp | His | Lys | Ala | Asp | Leu |
|     |     |     | 500 |     |     |     |     |     | 505 |     |     |     | 510 |     |     |
| Ala | Val | Ala | Pro | Leu | Ala | Ile | Thr | Tyr | Val | Arg | Glu | Lys | Val | Ile | Asp |
|     |     | 515 |     |     |     |     | 520 |     |     |     |     | 525 |     |     |     |
| Phe | Ser | Lys | Pro | Phe | Met | Thr | Leu | Gly | Ile | Ser | Ile | Leu | Tyr | Arg | Lys |
|     | 530 |     |     |     |     | 535 |     |     |     |     | 540 |     |     |     |     |
| Pro | Asn | Gly | Thr | Asn | Pro | Gly | Val | Phe | Ser | Phe | Leu | Asn | Pro | Leu | Ser |
| 545 |     |     |     |     | 550 |     |     |     |     | 555 |     |     |     |     | 560 |
| Pro | Asp | Ile | Trp | Met | Tyr | Val | Leu | Leu | Ala | Cys | Leu | Gly | Val | Ser | Cys |
|     |     |     |     | 565 |     |     |     |     | 570 |     |     |     |     | 575 |     |
| Val | Leu | Phe | Val | Ile | Ala | Arg | Phe | Ser | Pro | Tyr | Glu | Trp | Tyr | Asn | Pro |
|     |     |     | 580 |     |     |     |     | 585 |     |     |     |     | 590 |     |     |
| His | Pro | Cys | Asn | Pro | Asp | Ser | Asp | Val | Val | Glu | Asn | Asn | Phe | Thr | Leu |
|     |     | 595 |     |     |     |     | 600 |     |     |     |     | 605 |     |     |     |
| Leu | Asn | Ser | Phe | Trp | Phe | Gly | Val | Gly | Ala | Leu | Met | Arg | Gln | Gly | Ser |
|     | 610 |     |     |     |     | 615 |     |     |     |     | 620 |     |     |     |     |
| Glu | Leu | Met | Pro | Lys | Ala | Leu | Ser | Thr | Arg | Ile | Val | Gly | Gly | Ile | Trp |
| 625 |     |     |     |     | 630 |     |     |     |     | 635 |     |     |     |     | 640 |
| Trp | Phe | Phe | Thr | Leu | Ile | Ile | Ile | Ser | Ser | Tyr | Thr | Ala | Asn | Leu | Ala |
|     |     |     |     | 645 |     |     |     |     | 650 |     |     |     |     | 655 |     |
| Ala | Phe | Leu | Thr | Val | Glu | Arg | Met | Glu | Ser | Pro | Ile | Asp | Ser | Ala | Asp |
|     |     |     | 660 |     |     |     |     | 665 |     |     |     |     | 670 |     |     |
| Asp | Leu | Ala | Lys | Gln | Thr | Lys | Ile | Glu | Tyr | Gly | Ala | Val | Glu | Asp | Gly |
|     |     | 675 |     |     |     |     | 680 |     |     |     |     | 685 |     |     |     |
| Ala | Thr | Met | Thr | Phe | Phe | Lys | Lys | Ser | Lys | Ile | Ser | Thr | Tyr | Asp | Lys |
|     | 690 |     |     |     |     | 695 |     |     |     |     | 700 |     |     |     |     |
| Met | Trp | Ala | Phe | Met | Ser | Ser | Arg | Arg | Gln | Ser | Val | Leu | Val | Lys | Ser |
| 705 |     |     |     |     | 710 |     |     |     |     | 715 |     |     |     |     | 720 |
| Asn | Glu | Glu | Gly | Ile | Gln | Arg | Val | Leu | Thr | Ser | Asp | Tyr | Ala | Phe | Leu |
|     |     |     |     | 725 |     |     |     |     | 730 |     |     |     |     | 735 |     |
| Met | Glu | Ser | Thr | Thr | Ile | Glu | Phe | Val | Thr | Gln | Arg | Asn | Cys | Asn | Leu |
|     |     |     | 740 |     |     |     |     | 745 |     |     |     |     | 750 |     |     |
| Thr | Gln | Ile | Gly | Gly | Leu | Ile | Asp | Ser | Lys | Gly | Tyr | Gly | Val | Gly | Thr |
|     |     | 755 |     |     |     |     | 760 |     |     |     |     | 765 |     |     |     |
| Pro | Met | Gly | Ser | Pro | Tyr | Arg | Asp | Lys | Ile | Thr | Ile | Ala | Ile | Leu | Gln |
| 770 |     |     |     |     | 775 |     |     |     |     | 780 |     |     |     |     |     |
| Leu | Gln | Glu | Glu | Gly | Lys | Leu | His | Met | Met | Lys | Glu | Lys | Trp | Trp | Arg |
| 785 |     |     |     |     | 790 |     |     |     |     | 795 |     |     |     |     | 800 |
| Gly | Asn | Gly | Cys | Pro | Glu | Glu | Glu | Ser | Lys | Glu | Ala | Ser | Ala | Leu | Gly |
|     |     |     |     | 805 |     |     |     |     | 810 |     |     |     |     | 815 |     |
| Val | Gln | Asn | Ile | Gly | Gly | Ile | Phe | Ile | Val | Leu | Ala | Ala | Gly | Leu | Val |
|     |     |     | 820 |     |     |     |     | 825 |     |     |     |     | 830 |     |     |
| Leu | Ser | Val | Phe | Val | Ala | Val | Gly | Glu | Phe | Leu | Tyr | Lys | Ser | Lys | Lys |
|     |     | 835 |     |     |     |     | 840 |     |     |     |     | 845 |     |     |     |
| Asn | Ala | Gln | Leu | Glu | Lys | Arg | Ser | Phe | Cys | Ser | Ala | Met | Val | Glu | Glu |
|     | 850 |     |     |     |     | 855 |     |     |     |     | 860 |     |     |     |     |
| Leu | Arg | Met | Ser | Leu | Lys | Cys | Gln | Arg | Arg | Leu | Lys | His | Lys | Pro | Gln |
| 865 |     |     |     |     | 870 |     |     |     |     | 875 |     |     |     |     | 880 |
| Pro | Gln | Leu | Leu |     |     |     |     |     |     |     |     |     |     |     |     |

( 2 ) INFORMATION FOR SEQ ID NO:13:

( i ) SEQUENCE CHARACTERISTICS:
        ( A ) LENGTH: 3344 base pairs
        ( B ) TYPE: nucleic acid ( C ) STRANDEDNESS: single
( D ) TOPOLOGY: linear ( i i ) MOLECULE TYPE: cDNA ( v i ) ORIGINAL SOURCE:
    ( G ) CELL TYPE:
    ( H ) CELL LINE:

( v i i ) IMMEDIATE SOURCE:
    ( A ) LIBRARY:
    ( B ) CLONE: GluR7

( i x ) FEATURE:
    ( A ) NAME/KEY: CDS
    ( B ) LOCATION: 1..2766

( x i ) SEQUENCE DESCRIPTION: SEQ ID NO:13:

| | | | | | | | | | | | | | | | | |
|---|---|---|---|---|---|---|---|---|---|---|---|---|---|---|---|---|
| GGG | GCC | GTG | GCG | GGC | TCC | CTG | GGG | CGC | CTC | CGG | AGT | CTG | GTT | TGG | GAA | 48 |
| Gly | Ala | Val | Ala | Gly | Ser | Leu | Gly | Arg | Leu | Arg | Ser | Leu | Val | Trp | Glu | |
| 1 | | | | 5 | | | | | 10 | | | | | 15 | | |
| TAC | TGG | GCC | GGG | TTC | CTC | GTG | TGC | GCC | TTC | TGG | ATC | CCA | GAC | TCG | CGC | 96 |
| Tyr | Trp | Ala | Gly | Phe | Leu | Val | Cys | Ala | Phe | Trp | Ile | Pro | Asp | Ser | Arg | |
| | | | 20 | | | | | 25 | | | | | 30 | | | |
| GGG | ATG | CCC | CAC | GTC | ATC | CGG | ATC | GGC | GGA | ATC | TTT | GAG | TAC | GCG | GAC | 144 |
| Gly | Met | Pro | His | Val | Ile | Arg | Ile | Gly | Gly | Ile | Phe | Glu | Tyr | Ala | Asp | |
| | | 35 | | | | | 40 | | | | | 45 | | | | |
| GGC | CCC | AAC | GCC | CAG | GTC | ATG | AAC | GCT | GAG | GAG | CAC | GCC | TTT | CGG | TTT | 192 |
| Gly | Pro | Asn | Ala | Gln | Val | Met | Asn | Ala | Glu | Glu | His | Ala | Phe | Arg | Phe | |
| | 50 | | | | | 55 | | | | | 60 | | | | | |
| TCT | GCC | AAT | ATC | ATC | AAC | AGG | AAC | AGA | ACT | CTG | CTG | CCC | AAC | ACG | ACC | 240 |
| Ser | Ala | Asn | Ile | Ile | Asn | Arg | Asn | Arg | Thr | Leu | Leu | Pro | Asn | Thr | Thr | |
| 65 | | | | | 70 | | | | | 75 | | | | | 80 | |
| CTG | ACC | TAC | GAC | ATT | CAG | AGG | ATT | CAC | TTC | CAT | GAC | AGT | TTT | GAG | GCC | 288 |
| Leu | Thr | Tyr | Asp | Ile | Gln | Arg | Ile | His | Phe | His | Asp | Ser | Phe | Glu | Ala | |
| | | | | 85 | | | | | 90 | | | | | 95 | | |
| ACC | AAG | AAG | GCC | TGT | GAC | CAG | TTG | GCG | CTC | GGT | GTG | GTA | GCC | ATC | TTT | 336 |
| Thr | Lys | Lys | Ala | Cys | Asp | Gln | Leu | Ala | Leu | Gly | Val | Val | Ala | Ile | Phe | |
| | | | 100 | | | | | 105 | | | | | 110 | | | |
| GGG | CCA | TCC | CAG | GGC | TCC | TGC | ATC | AAT | GCC | GTC | CAG | TCC | ATC | TGC | AAT | 384 |
| Gly | Pro | Ser | Gln | Gly | Ser | Cys | Ile | Asn | Ala | Val | Gln | Ser | Ile | Cys | Asn | |
| | | 115 | | | | | 120 | | | | | 125 | | | | |
| GCC | TTG | GAG | GTT | CCT | CAC | ATC | CAA | CTG | CGC | TGG | AAG | CAC | CAC | CCC | CTG | 432 |
| Ala | Leu | Glu | Val | Pro | His | Ile | Gln | Leu | Arg | Trp | Lys | His | His | Pro | Leu | |
| | 130 | | | | | 135 | | | | | 140 | | | | | |
| GAC | AAC | AAG | GAC | ACC | TTC | TAC | GTG | AAC | CTC | TAC | CCC | GAC | TAC | GCC | TCT | 480 |
| Asp | Asn | Lys | Asp | Thr | Phe | Tyr | Val | Asn | Leu | Tyr | Pro | Asp | Tyr | Ala | Ser | |
| 145 | | | | | 150 | | | | | 155 | | | | | 160 | |
| CTC | AGC | CAC | GCC | ATC | CTC | GAC | TTG | GTC | CAG | TCC | CTC | AAG | TGG | CGG | TCA | 528 |
| Leu | Ser | His | Ala | Ile | Leu | Asp | Leu | Val | Gln | Ser | Leu | Lys | Trp | Arg | Ser | |
| | | | | 165 | | | | | 170 | | | | | 175 | | |
| GCC | ACC | GTA | GTC | TAT | GAT | GAC | AGT | ACA | GGT | CTC | ATC | CGG | CTG | CAG | GAG | 576 |
| Ala | Thr | Val | Val | Tyr | Asp | Asp | Ser | Thr | Gly | Leu | Ile | Arg | Leu | Gln | Glu | |
| | | | 180 | | | | | 185 | | | | | 190 | | | |
| CTC | ATC | ATG | GCT | CCA | TCT | AGG | TAC | AAC | ATC | CGC | CTG | AAG | ATT | CGC | CAG | 624 |
| Leu | Ile | Met | Ala | Pro | Ser | Arg | Tyr | Asn | Ile | Arg | Leu | Lys | Ile | Arg | Gln | |
| | | 195 | | | | | 200 | | | | | 205 | | | | |
| CTC | CCC | ATC | GAC | TCC | GAT | GAC | TCA | CGC | CCC | TTG | CTC | AAA | GAG | ATG | AAG | 672 |
| Leu | Pro | Ile | Asp | Ser | Asp | Asp | Ser | Arg | Pro | Leu | Leu | Lys | Glu | Met | Lys | |
| | 210 | | | | | 215 | | | | | 220 | | | | | |
| CGG | GGC | CGG | GAG | TTC | CGT | ATC | ATC | TTT | GAC | TGC | AGT | CAC | ACC | ATG | GCA | 720 |
| Arg | Gly | Arg | Glu | Phe | Arg | Ile | Ile | Phe | Asp | Cys | Ser | His | Thr | Met | Ala | |
| 225 | | | | | 230 | | | | | 235 | | | | | 240 | |
| GCC | CAG | ATC | CTC | AAG | CAG | GCC | ATG | GCC | ATG | GGC | ATG | ATG | ACG | GAA | TAC | 768 |
| Ala | Gln | Ile | Leu | Lys | Gln | Ala | Met | Ala | Met | Gly | Met | Met | Thr | Glu | Tyr | |
| | | | | 245 | | | | | 250 | | | | | 255 | | |

| | | | | | | | | | | | | | | | | |
|---|---|---|---|---|---|---|---|---|---|---|---|---|---|---|---|---|
| TAC | CAC | TTC | ATC | TTC | ACC | ACT | CTG | GAT | CTC | TAT | GCG | CTA | GAC | CTG | GAA | 816 |
| Tyr | His | Phe | Ile | Phe | Thr | Thr | Leu | Asp | Leu | Tyr | Ala | Leu | Asp | Leu | Glu | |
| | | | 260 | | | | 265 | | | | | | 270 | | | |
| CCC | TAC | CGC | TAC | TCG | GGA | GTG | AAC | CTG | ACT | GGG | TTC | CGC | ATA | CTC | AAC | 864 |
| Pro | Tyr | Arg | Tyr | Ser | Gly | Val | Asn | Leu | Thr | Gly | Phe | Arg | Ile | Leu | Asn | |
| | | 275 | | | | | 280 | | | | | 285 | | | | |
| GTG | GAC | AAC | CCC | CAT | GTC | TCA | GCC | ATT | GTG | GAG | AAG | TGG | TCC | ATG | GAG | 912 |
| Val | Asp | Asn | Pro | His | Val | Ser | Ala | Ile | Val | Glu | Lys | Trp | Ser | Met | Glu | |
| | 290 | | | | | 295 | | | | | 300 | | | | | |
| CGG | CTA | CAG | GCA | GCT | CCC | CGG | GCA | GAG | TCA | GGC | CTG | CTG | GAT | GGA | GTG | 960 |
| Arg | Leu | Gln | Ala | Ala | Pro | Arg | Ala | Glu | Ser | Gly | Leu | Leu | Asp | Gly | Val | |
| 305 | | | | | 310 | | | | | 315 | | | | | 320 | |
| ATG | ATG | ACC | GAT | GCA | GCC | CTG | CTC | TAC | GAT | GCG | GTC | CAC | ATT | GTG | TCT | 1008 |
| Met | Met | Thr | Asp | Ala | Ala | Leu | Leu | Tyr | Asp | Ala | Val | His | Ile | Val | Ser | |
| | | | | 325 | | | | | 330 | | | | | 335 | | |
| GTG | TGC | TAC | CAG | CGA | GCG | CCG | CAG | ATG | ACT | GTG | AAC | TCC | CTA | CAG | TGC | 1056 |
| Val | Cys | Tyr | Gln | Arg | Ala | Pro | Gln | Met | Thr | Val | Asn | Ser | Leu | Gln | Cys | |
| | | | 340 | | | | | 345 | | | | | 350 | | | |
| CAT | CGG | CAC | AAG | GCC | TGG | CGC | TTC | GGT | GGC | CGC | TTC | ATG | AAC | TTC | ATC | 1104 |
| His | Arg | His | Lys | Ala | Trp | Arg | Phe | Gly | Gly | Arg | Phe | Met | Asn | Phe | Ile | |
| | | 355 | | | | | 360 | | | | | 365 | | | | |
| AAG | GAG | GCT | CAA | TGG | GAA | GGA | TTA | ACT | GGA | CGG | ATT | GTT | TTC | AAC | AAA | 1152 |
| Lys | Glu | Ala | Gln | Trp | Glu | Gly | Leu | Thr | Gly | Arg | Ile | Val | Phe | Asn | Lys | |
| | 370 | | | | | 375 | | | | | 380 | | | | | |
| ACC | AGT | GGC | TTG | CGG | ACT | GAT | TTT | GAT | CTG | GAC | ATC | ATC | AGC | CTC | AAG | 1200 |
| Thr | Ser | Gly | Leu | Arg | Thr | Asp | Phe | Asp | Leu | Asp | Ile | Ile | Ser | Leu | Lys | |
| 385 | | | | | 390 | | | | | 395 | | | | | 400 | |
| GAA | GAT | GGC | CTC | GAG | AAG | GTC | GGG | GTG | TGG | AGT | CCA | GCT | GAC | GGT | CTC | 1248 |
| Glu | Asp | Gly | Leu | Glu | Lys | Val | Gly | Val | Trp | Ser | Pro | Ala | Asp | Gly | Leu | |
| | | | | 405 | | | | | 410 | | | | | 415 | | |
| AAT | ATC | ACT | GAG | GTT | GCC | AAA | GGC | CGA | GGT | CCT | AAT | GTC | ACC | GAC | TCT | 1296 |
| Asn | Ile | Thr | Glu | Val | Ala | Lys | Gly | Arg | Gly | Pro | Asn | Val | Thr | Asp | Ser | |
| | | | 420 | | | | | 425 | | | | | 430 | | | |
| CTG | ACC | AAC | AGG | TCA | CTC | ATC | GTC | ACC | ACT | CTG | CTG | GAG | GAG | CCT | TTT | 1344 |
| Leu | Thr | Asn | Arg | Ser | Leu | Ile | Val | Thr | Thr | Leu | Leu | Glu | Glu | Pro | Phe | |
| | | | 435 | | | | | 440 | | | | | 445 | | | |
| GTC | ATG | TTC | CGC | AAG | TCT | GAT | AGG | ACC | CTT | TAC | GGC | AAT | GAC | CGG | TTC | 1392 |
| Val | Met | Phe | Arg | Lys | Ser | Asp | Arg | Thr | Leu | Tyr | Gly | Asn | Asp | Arg | Phe | |
| | 450 | | | | | 455 | | | | | 460 | | | | | |
| GAG | GGC | TAC | TGC | ATC | GAC | TTG | CTC | AAG | GAG | CTG | GCG | CAC | ATC | CTG | GGC | 1440 |
| Glu | Gly | Tyr | Cys | Ile | Asp | Leu | Leu | Lys | Glu | Leu | Ala | His | Ile | Leu | Gly | |
| 465 | | | | | 470 | | | | | 475 | | | | | 480 | |
| TTC | TCC | TAC | GAG | ATC | CGG | CTG | GTG | GAA | GAC | GGC | AAG | TAC | GGG | GCA | CAG | 1488 |
| Phe | Ser | Tyr | Glu | Ile | Arg | Leu | Val | Glu | Asp | Gly | Lys | Tyr | Gly | Ala | Gln | |
| | | | | 485 | | | | | 490 | | | | | 495 | | |
| GAC | GAC | AAG | GGC | CAG | TGG | AAC | GGC | ATG | GTC | AAG | GAA | CTC | ATT | GAC | CAC | 1536 |
| Asp | Asp | Lys | Gly | Gln | Trp | Asn | Gly | Met | Val | Lys | Glu | Leu | Ile | Asp | His | |
| | | | 500 | | | | | 505 | | | | | 510 | | | |
| AAA | GCA | GAT | CTG | GCT | GTG | GCT | CCC | CTG | ACC | ATC | ACC | CAT | GTC | CGA | GAG | 1584 |
| Lys | Ala | Asp | Leu | Ala | Val | Ala | Pro | Leu | Thr | Ile | Thr | His | Val | Arg | Glu | |
| | | 515 | | | | | 520 | | | | | 525 | | | | |
| AAG | GCC | ATT | GAC | TTC | TCT | AAG | CCT | TTT | ATG | ACC | CTC | GGA | GTG | AGC | ATC | 1632 |
| Lys | Ala | Ile | Asp | Phe | Ser | Lys | Pro | Phe | Met | Thr | Leu | Gly | Val | Ser | Ile | |
| | | 530 | | | | | 535 | | | | | 540 | | | | |
| TTA | TAT | CGA | AAA | CCC | AAT | GGC | ACC | AAC | CCC | AGT | GTC | TTC | TCC | TTC | CTC | 1680 |
| Leu | Tyr | Arg | Lys | Pro | Asn | Gly | Thr | Asn | Pro | Ser | Val | Phe | Ser | Phe | Leu | |
| 545 | | | | | 550 | | | | | 555 | | | | | 560 | |
| AAC | CCC | CTG | TCC | CCA | GAC | ATC | TGG | ATG | TAC | GTG | CTA | CTC | GCC | TAC | CTG | 1728 |
| Asn | Pro | Leu | Ser | Pro | Asp | Ile | Trp | Met | Tyr | Val | Leu | Leu | Ala | Tyr | Leu | |
| | | | | 565 | | | | | 570 | | | | | 575 | | |
| GGT | GTC | AGC | TGT | GTC | CTC | TTC | GTC | ATT | GCC | AGA | TTC | AGC | CCT | TAT | GAA | 1776 |

|  |  |  |  |  |  |  |  |  |  |  |  |  |  |  |  |
|---|---|---|---|---|---|---|---|---|---|---|---|---|---|---|---|
| Gly | Val | Ser | Cys<br>580 | Val | Leu | Phe | Val | Ile<br>585 | Ala | Arg | Phe | Ser | Pro<br>590 | Tyr | Glu |

| TGG | TAT | GAT | GCC | CAC | CCC | TGC | AAC | CCC | GGC | TCT | GAG | GTG | GTG | GAG | AAT | 1824 |
|---|---|---|---|---|---|---|---|---|---|---|---|---|---|---|---|---|
| Trp | Tyr | Asp<br>595 | Ala | His | Pro | Cys<br>600 | Asn | Pro | Gly | Ser | Glu<br>605 | Val | Val | Glu | Asn | |

| AAC | TTC | ACG | CTG | CTC | AAC | AGC | TTC | TGG | TTT | GGA | ATG | GGC | TCC | CTG | ATG | 1872 |
|---|---|---|---|---|---|---|---|---|---|---|---|---|---|---|---|---|
| Asn | Phe<br>610 | Thr | Leu | Leu | Asn | Ser<br>615 | Phe | Trp | Phe | Gly | Met<br>620 | Gly | Ser | Leu | Met | |

| CAA | CAA | GGA | TCT | GAA | CTG | ATG | CCC | AAA | GCT | CTG | TCT | ACC | CGC | ATC | ATT | 1920 |
|---|---|---|---|---|---|---|---|---|---|---|---|---|---|---|---|---|
| Gln | Gln<br>625 | Gly | Ser | Glu | Leu | Met<br>630 | Pro | Lys | Ala | Leu | Ser<br>635 | Thr | Arg | Ile | Ile<br>640 | |

| GGC | GGC | ATC | TGG | TGG | TTC | TTC | ACC | CTT | ATT | ATC | ATC | TCC | TCC | TAC | ACG | 1968 |
|---|---|---|---|---|---|---|---|---|---|---|---|---|---|---|---|---|
| Gly | Gly | Ile | Trp | Trp<br>645 | Phe | Phe | Thr | Leu | Ile<br>650 | Ile | Ile | Ser | Ser | Tyr<br>655 | Thr | |

| GCC | AAC | CTG | GCT | GCC | TTC | CTG | ACC | GTG | GAG | CGC | ATG | GAG | TCA | CCC | ATC | 2016 |
|---|---|---|---|---|---|---|---|---|---|---|---|---|---|---|---|---|
| Ala | Asn | Leu | Ala<br>660 | Ala | Phe | Leu | Thr | Val<br>665 | Glu | Arg | Met | Glu | Ser<br>670 | Pro | Ile | |

| GAC | TCT | GCC | GAT | GAC | CTG | GCC | AAG | CAG | ACC | AAA | ATA | GAG | TAC | GGT | GCT | 2064 |
|---|---|---|---|---|---|---|---|---|---|---|---|---|---|---|---|---|
| Asp | Ser | Ala<br>675 | Asp | Asp | Leu | Ala | Lys<br>680 | Gln | Thr | Lys | Ile | Glu<br>685 | Tyr | Gly | Ala | |

| GTC | AAG | GAT | GGG | GCC | ACC | ATG | ACC | TTC | TTC | AAG | AAA | TCC | AAG | ATC | TCC | 2112 |
|---|---|---|---|---|---|---|---|---|---|---|---|---|---|---|---|---|
| Val | Lys<br>690 | Asp | Gly | Ala | Thr | Met<br>695 | Thr | Phe | Phe | Lys | Lys<br>700 | Ser | Lys | Ile | Ser | |

| ACC | TTT | GAG | AAG | ATG | TGG | GCC | TTC | ATG | AGC | AGC | AAG | CCC | TCG | GCT | CTG | 2160 |
|---|---|---|---|---|---|---|---|---|---|---|---|---|---|---|---|---|
| Thr<br>705 | Phe | Glu | Lys | Met | Trp<br>710 | Ala | Phe | Met | Ser | Ser<br>715 | Lys | Pro | Ser | Ala | Leu<br>720 | |

| GTG | AAG | AAC | AAT | GAG | GAG | GGC | ATC | CAG | CGG | ACA | CTC | ACA | GCT | GAC | TAC | 2208 |
|---|---|---|---|---|---|---|---|---|---|---|---|---|---|---|---|---|
| Val | Lys | Asn | Asn | Glu<br>725 | Glu | Gly | Ile | Gln | Arg<br>730 | Thr | Leu | Thr | Ala | Asp<br>735 | Tyr | |

| GCT | CTG | CTC | ATG | GAG | TCC | ACG | ACC | ATA | GAG | TAC | ATC | ACA | CAA | AGG | AAC | 2256 |
|---|---|---|---|---|---|---|---|---|---|---|---|---|---|---|---|---|
| Ala | Leu | Leu | Met<br>740 | Glu | Ser | Thr | Thr | Ile<br>745 | Glu | Tyr | Ile | Thr | Gln<br>750 | Arg | Asn | |

| TGC | AAT | CTC | ACC | CAG | ATC | GGC | GGC | CTC | ATC | GAT | TCC | AAG | GGC | TAC | GGC | 2304 |
|---|---|---|---|---|---|---|---|---|---|---|---|---|---|---|---|---|
| Cys | Asn | Leu | Thr<br>755 | Gln | Ile | Gly | Gly | Leu<br>760 | Ile | Asp | Ser | Lys | Gly<br>765 | Tyr | Gly | |

| ATC | GGC | ACG | CCC | ATG | GGC | TCC | CCC | TAC | AGG | GAC | AAA | ATC | ACC | ATC | GCC | 2352 |
|---|---|---|---|---|---|---|---|---|---|---|---|---|---|---|---|---|
| Ile | Gly | Thr<br>770 | Pro | Met | Gly | Ser | Pro<br>775 | Tyr | Arg | Asp | Lys | Ile<br>780 | Thr | Ile | Ala | |

| ATT | CTG | CAG | CTG | CAG | GAG | GAG | GAC | AAG | CTG | CAC | ATC | ATG | AAG | GAG | AAG | 2400 |
|---|---|---|---|---|---|---|---|---|---|---|---|---|---|---|---|---|
| Ile | Leu<br>785 | Gln | Leu | Gln | Glu | Glu<br>790 | Asp | Lys | Leu | His | Ile<br>795 | Met | Lys | Glu | Lys<br>800 | |

| TGG | TGG | CGA | GGC | AGC | GGG | TGC | CCC | GAG | GAG | GAG | AAC | AAG | GAG | GCC | AGC | 2448 |
|---|---|---|---|---|---|---|---|---|---|---|---|---|---|---|---|---|
| Trp | Trp | Arg | Gly | Ser<br>805 | Gly | Cys | Pro | Glu | Glu<br>810 | Glu | Asn | Lys | Glu | Ala<br>815 | Ser | |

| GCA | CTG | GGC | ATC | CAG | AAG | ATT | GGC | GGC | ATC | TTC | ATC | GTC | CTG | GCT | GCC | 2496 |
|---|---|---|---|---|---|---|---|---|---|---|---|---|---|---|---|---|
| Ala | Leu | Gly | Ile<br>820 | Gln | Lys | Ile | Gly | Gly<br>825 | Ile | Phe | Ile | Val | Leu<br>830 | Ala | Ala | |

| GGC | TTA | GTC | CTG | TCC | GTG | TTG | GTG | GCA | GTG | GGC | GAG | TTT | ATA | TAC | AAA | 2544 |
|---|---|---|---|---|---|---|---|---|---|---|---|---|---|---|---|---|
| Gly | Leu | Val<br>835 | Leu | Ser | Val | Leu | Val<br>840 | Ala | Val | Gly | Glu | Phe<br>845 | Ile | Tyr | Lys | |

| CTC | CGC | AAG | ACA | GCG | GAA | CGG | GAG | CAG | CGC | TCT | TTC | TGC | AGC | ACA | GTG | 2592 |
|---|---|---|---|---|---|---|---|---|---|---|---|---|---|---|---|---|
| Leu | Arg<br>850 | Lys | Thr | Ala | Glu | Arg<br>855 | Glu | Gln | Arg | Ser | Phe<br>860 | Cys | Ser | Thr | Val | |

| GCC | GAC | GAG | ATC | CGC | TTC | TCC | CTC | ACC | TGC | CAG | CGG | CGT | CTC | AAG | CAC | 2640 |
|---|---|---|---|---|---|---|---|---|---|---|---|---|---|---|---|---|
| Ala<br>865 | Asp | Glu | Ile | Arg | Phe<br>870 | Ser | Leu | Thr | Cys | Gln<br>875 | Arg | Arg | Leu | Lys | His<br>880 | |

| AAG | CCA | CAG | CCT | CCT | ATG | ATG | GTC | AAG | ACA | GAT | GCG | GTT | ATC | AAC | ATG | 2688 |
|---|---|---|---|---|---|---|---|---|---|---|---|---|---|---|---|---|
| Lys | Pro | Gln | Pro | Pro<br>885 | Met | Met | Val | Lys | Thr<br>890 | Asp | Ala | Val | Ile | Asn<br>895 | Met | |

| CAC | ACC | TTT | AAT | GAC | CGA | AGG | CTT | CCA | GGC | AAG | GAC | AGC | ATG | AGC | TGC | 2736 |
|---|---|---|---|---|---|---|---|---|---|---|---|---|---|---|---|---|
| His | Thr | Phe | Asn<br>900 | Asp | Arg | Arg | Leu | Pro<br>905 | Gly | Lys | Asp | Ser | Met<br>910 | Ser | Cys | |

```
AGC  ACC  TCG  CTA  GCC  CCT  GTC  TTC  CCT  TAGACTTGGG  TCCAGCGGGG                    2783
Ser  Thr  Ser  Leu  Ala  Pro  Val  Phe  Pro
              915                      920

ACTTCAGGCC  CGGTCCACGC  AGAGGAAGGC  AAAGGAGACC  CGAAAGGACA  TCCTCATCTC                 2843

ATGCTGGCCT  TGGGGATGGA  GCTGCTGCCC  GCATCCGGCT  GTGAACCATC  AGCTCTTACC                 2903

TACCGGGGAA  ACCCATGGGC  CCTCAGCAGC  TGCTTGGGCT  TCATCTCCTC  TTGTCTTTTT                 2963

TGTGGCTTTC  TGAAGCTGTG  AAGGCCAGCG  GAAGCACACG  CCTCTCAGGC  TGCACTCACC                 3023

GACCATCTCC  ATAGCCAGCT  ACTTCGGCCA  GGGCTCTGCA  GAGGCCTCGG  AACACCAGAG                 3083

ATAGCTCTTA  CACCTCCCTC  CCTCCCCTCA  AGTCCAGGCC  TTCTAGCACG  CACCCATGAG                 3143

AGCAGAGACT  CCAGCTCAGA  ACGCCTTGAG  GGTGTTCTGA  GGAGGCCACC  AGTGGGAGCC                 3203

CCAAGGCAGC  CATCCATACC  TGGACAGAAG  CAAAGCTTCA  GCCCTTAAGG  GCTATTCACC                 3263

TGGGTCTGCC  CTCCCCAACG  TGGCTTCGCC  CTCGTGCCGA  ATTCGATATC  AAGCTTATCG                 3323

ATACCGTCGA  CCTCGAGGGG  G                                                              3344
```

( 2 ) INFORMATION FOR SEQ ID NO:14:

( i ) SEQUENCE CHARACTERISTICS:
        ( A ) LENGTH: 921 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Gly  Ala  Val  Ala  Gly  Ser  Leu  Gly  Arg  Leu  Arg  Ser  Leu  Val  Trp  Glu
  1              5                        10                       15

Tyr  Trp  Ala  Gly  Phe  Leu  Val  Cys  Ala  Phe  Trp  Ile  Pro  Asp  Ser  Arg
              20                       25                       30

Gly  Met  Pro  His  Val  Ile  Arg  Ile  Gly  Gly  Ile  Phe  Glu  Tyr  Ala  Asp
              35                       40                       45

Gly  Pro  Asn  Ala  Gln  Val  Met  Asn  Ala  Glu  Glu  His  Ala  Phe  Arg  Phe
         50                       55                       60

Ser  Ala  Asn  Ile  Ile  Asn  Arg  Asn  Arg  Thr  Leu  Leu  Pro  Asn  Thr  Thr
 65                       70                       75                       80

Leu  Thr  Tyr  Asp  Ile  Gln  Arg  Ile  His  Phe  His  Asp  Ser  Phe  Glu  Ala
                   85                       90                       95

Thr  Lys  Lys  Ala  Cys  Asp  Gln  Leu  Ala  Leu  Gly  Val  Val  Ala  Ile  Phe
              100                      105                      110

Gly  Pro  Ser  Gln  Gly  Ser  Cys  Ile  Asn  Ala  Val  Gln  Ser  Ile  Cys  Asn
              115                      120                      125

Ala  Leu  Glu  Val  Pro  His  Ile  Gln  Leu  Arg  Trp  Lys  His  His  Pro  Leu
         130                      135                      140

Asp  Asn  Lys  Asp  Thr  Phe  Tyr  Val  Asn  Leu  Tyr  Pro  Asp  Tyr  Ala  Ser
145                       150                      155                      160

Leu  Ser  His  Ala  Ile  Leu  Asp  Leu  Val  Gln  Ser  Leu  Lys  Trp  Arg  Ser
                   165                      170                      175

Ala  Thr  Val  Val  Tyr  Asp  Asp  Ser  Thr  Gly  Leu  Ile  Arg  Leu  Gln  Glu
              180                      185                      190

Leu  Ile  Met  Ala  Pro  Ser  Arg  Tyr  Asn  Ile  Arg  Leu  Lys  Ile  Arg  Gln
              195                      200                      205

Leu  Pro  Ile  Asp  Ser  Asp  Asp  Ser  Arg  Pro  Leu  Leu  Lys  Glu  Met  Lys
         210                      215                      220

Arg  Gly  Arg  Glu  Phe  Arg  Ile  Ile  Phe  Asp  Cys  Ser  His  Thr  Met  Ala
225                       230                      235                      240
```

| | | | | | | | | | | | | | | |
|---|---|---|---|---|---|---|---|---|---|---|---|---|---|---|
| Ala | Gln | Ile | Leu | Lys 245 | Gln | Ala | Met | Ala 250 | Met | Gly | Met | Met | Thr 255 | Glu | Tyr |
| Tyr | His | Phe | Ile 260 | Phe | Thr | Thr | Leu | Asp 265 | Leu | Tyr | Ala | Leu 270 | Asp | Leu | Glu |
| Pro | Tyr | Arg 275 | Tyr | Ser | Gly | Val | Asn 280 | Leu | Thr | Gly | Phe 285 | Arg | Ile | Leu | Asn |
| Val | Asp 290 | Asn | Pro | His | Val | Ser 295 | Ala | Ile | Val | Glu 300 | Lys | Trp | Ser | Met | Glu |
| Arg 305 | Leu | Gln | Ala | Ala | Pro 310 | Arg | Ala | Glu | Ser 315 | Gly | Leu | Leu | Asp | Gly | Val 320 |
| Met | Met | Thr | Asp 325 | Ala | Ala | Leu | Leu | Tyr | Asp 330 | Ala | Val | His | Ile 335 | Val | Ser |
| Val | Cys | Tyr | Gln 340 | Arg | Ala | Pro | Gln | Met 345 | Thr | Val | Asn | Ser 350 | Leu | Gln | Cys |
| His | Arg | His 355 | Lys | Ala | Trp | Arg | Phe 360 | Gly | Gly | Arg | Phe | Met 365 | Asn | Phe | Ile |
| Lys | Glu 370 | Ala | Gln | Trp | Glu | Gly 375 | Leu | Thr | Gly | Arg | Ile 380 | Val | Phe | Asn | Lys |
| Thr 385 | Ser | Gly | Leu | Arg | Thr 390 | Asp | Phe | Asp | Leu | Asp 395 | Ile | Ile | Ser | Leu | Lys 400 |
| Glu | Asp | Gly | Leu | Glu 405 | Lys | Val | Gly | Val | Trp 410 | Ser | Pro | Ala | Asp 415 | Gly | Leu |
| Asn | Ile | Thr | Glu 420 | Val | Ala | Lys | Gly | Arg 425 | Gly | Pro | Asn | Val | Thr 430 | Asp | Ser |
| Leu | Thr | Asn 435 | Arg | Ser | Leu | Ile | Val 440 | Thr | Thr | Leu | Leu | Glu 445 | Glu | Pro | Phe |
| Val | Met | Phe 450 | Arg | Lys | Ser | Asp | Arg 455 | Thr | Leu | Tyr | Gly 460 | Asn | Asp | Arg | Phe |
| Glu 465 | Gly | Tyr | Cys | Ile | Asp 470 | Leu | Leu | Lys | Glu | Leu 475 | Ala | His | Ile | Leu | Gly 480 |
| Phe | Ser | Tyr | Glu | Ile 485 | Arg | Leu | Val | Glu | Asp 490 | Gly | Lys | Tyr | Gly | Ala 495 | Gln |
| Asp | Asp | Lys | Gly 500 | Gln | Trp | Asn | Gly | Met 505 | Val | Lys | Glu | Leu | Ile 510 | Asp | His |
| Lys | Ala | Asp 515 | Leu | Ala | Val | Ala | Pro 520 | Leu | Thr | Ile | Thr | His 525 | Val | Arg | Glu |
| Lys | Ala 530 | Ile | Asp | Phe | Ser | Lys 535 | Pro | Phe | Met | Thr | Leu 540 | Gly | Val | Ser | Ile |
| Leu 545 | Tyr | Arg | Lys | Pro | Asn 550 | Gly | Thr | Asn | Pro | Ser 555 | Val | Phe | Ser | Phe | Leu 560 |
| Asn | Pro | Leu | Ser | Pro 565 | Asp | Ile | Trp | Met | Tyr 570 | Val | Leu | Leu | Ala 575 | Tyr | Leu |
| Gly | Val | Ser | Cys 580 | Val | Leu | Phe | Val | Ile 585 | Ala | Arg | Phe | Ser 590 | Pro | Tyr | Glu |
| Trp | Tyr | Asp 595 | Ala | His | Pro | Cys | Asn 600 | Pro | Gly | Ser | Glu | Val 605 | Val | Glu | Asn |
| Asn | Phe 610 | Thr | Leu | Leu | Asn | Ser 615 | Phe | Trp | Phe | Gly | Met 620 | Gly | Ser | Leu | Met |
| Gln 625 | Gln | Gly | Ser | Glu | Leu 630 | Met | Pro | Lys | Ala | Leu 635 | Ser | Thr | Arg | Ile | Ile 640 |
| Gly | Gly | Ile | Trp | Trp 645 | Phe | Phe | Thr | Leu | Ile 650 | Ile | Ile | Ser | Ser | Tyr 655 | Thr |
| Ala | Asn | Leu | Ala 660 | Ala | Phe | Leu | Thr | Val 665 | Glu | Arg | Met | Glu 670 | Ser | Pro | Ile |
| Asp | Ser | Ala | Asp | Asp | Leu | Ala | Lys | Gln | Thr | Lys | Ile | Glu | Tyr | Gly | Ala |

|  | 675 |  |  |  |  | 680 |  |  |  |  | 685 |  |  |  |
|---|---|---|---|---|---|---|---|---|---|---|---|---|---|---|
| Val | Lys<br>690 | Asp | Gly | Ala | Thr | Met<br>695 | Thr | Phe | Phe | Lys | Lys<br>700 | Ser | Lys | Ile | Ser |
| Thr<br>705 | Phe | Glu | Lys | Met | Trp<br>710 | Ala | Phe | Met | Ser | Ser<br>715 | Lys | Pro | Ser | Ala | Leu<br>720 |
| Val | Lys | Asn | Asn | Glu<br>725 | Glu | Gly | Ile | Gln | Arg<br>730 | Thr | Leu | Thr | Ala | Asp<br>735 | Tyr |
| Ala | Leu | Leu | Met<br>740 | Glu | Ser | Thr | Thr | Ile<br>745 | Glu | Tyr | Ile | Thr | Gln<br>750 | Arg | Asn |
| Cys | Asn | Leu<br>755 | Thr | Gln | Ile | Gly | Gly<br>760 | Leu | Ile | Asp | Ser | Lys<br>765 | Gly | Tyr | Gly |
| Ile | Gly<br>770 | Thr | Pro | Met | Gly<br>775 | Ser | Pro | Tyr | Arg | Asp<br>780 | Lys | Ile | Thr | Ile | Ala |
| Ile<br>785 | Leu | Gln | Leu | Gln | Glu<br>790 | Glu | Asp | Lys | Leu | His<br>795 | Ile | Met | Lys | Glu | Lys<br>800 |
| Trp | Trp | Arg | Gly | Ser<br>805 | Gly | Cys | Pro | Glu | Glu<br>810 | Glu | Asn | Lys | Glu | Ala<br>815 | Ser |
| Ala | Leu | Gly | Ile<br>820 | Gln | Lys | Ile | Gly | Gly<br>825 | Ile | Phe | Ile | Val | Leu<br>830 | Ala | Ala |
| Gly | Leu | Val<br>835 | Leu | Ser | Val | Leu | Val<br>840 | Ala | Val | Gly | Glu | Phe<br>845 | Ile | Tyr | Lys |
| Leu | Arg<br>850 | Lys | Thr | Ala | Glu | Arg<br>855 | Glu | Gln | Arg | Ser | Phe<br>860 | Cys | Ser | Thr | Val |
| Ala<br>865 | Asp | Glu | Ile | Arg | Phe<br>870 | Ser | Leu | Thr | Cys | Gln<br>875 | Arg | Arg | Leu | Lys | His<br>880 |
| Lys | Pro | Gln | Pro | Pro<br>885 | Met | Met | Val | Lys | Thr<br>890 | Asp | Ala | Val | Ile | Asn<br>895 | Met |
| His | Thr | Phe | Asn<br>900 | Asp | Arg | Arg | Leu | Pro<br>905 | Gly | Lys | Asp | Ser | Met<br>910 | Ser | Cys |
| Ser | Thr | Ser<br>915 | Leu | Ala | Pro | Val | Phe<br>920 | Pro |  |  |  |  |  |  |  |

What is claimed is:

1. Substantially pure DNA capable of hybridizing with at least one polynucleotide selected from GluR1 (Sequence ID No. 1), GluR2 (Sequence ID No. 3), GluR3 (Sequence ID No. 5), GluR4 (Sequence ID No. 7), GluR5 (Sequence ID No. 9), GluR6 (Sequence ID No. 11), or GluR7 (Sequence ID No. 13) under low stringency hybridization conditions, said DNA encoding protein characterized as having electrophysiological and pharmacological properties of at least one glutamate receptor subtype selected from the N-methyl-D-aspartate (NMDA) subtype, the α-amino-3-hydroxy-5-methyl-isoxasole-4-propionic acid (AMPA) subtype, the kainate (KA) subtype, or the 2-amino-4-phosphonobutyrate (APB) subtype.

2. Isolated mRNA complementary to the DNA of claim 1.

3. Oocytes expressing the mRNA of claim 2.

4. A nucleic acid probe comprising an ion channel encoding portion of the DNA of claim 1.

5. A method for identifying DNA encoding glutamate receptor protein, said method comprising:
   contacting DNA with a probe according to claim 4, wherein said contacting is carried out under hybridization conditions, and
   identifying DNA(s) which display(s) a substantial degree of hybridization to said probe.

6. DNA according to claim 1 encoding a protein having substantially the same amino acid sequence as GluR1, GluR2, GluR3, GluR4, GluR5, GluR6, or GluR7.

7. A nucleic acid probe comprising an ion channel encoding portion of the DNA of claim 6.

8. Isolated mRNA complementary to the DNA of claim 6.

9. Oocytes expressing the mRNA of claim 8.

10. DNA according to claim 1 wherein said DNA has substantially the same sequence as GluR1 (Sequence ID No. 1), GluR2 (Sequence ID No. 3), GluR3 (Sequence ID No. 5), GluR4 (Sequence ID No. 7), GluR5 (Sequence ID No. 9), GluR6 (Sequence ID No. 11), or GluR7 (Sequence ID No. 13).

11. A nucleic acid probe comprising an ion channel encoding portion of the DNA of claim 10.

12. Isolated mRNA complementary to the DNA of claim 10.

13. Oocytes expressing the mRNA or claim 12.

14. DNA according to claim 1 wherein said glutamate receptor subtype(s) are of the KA and/or AMPA subtype.

* * * * *